United States Patent
Cao et al.

(10) Patent No.: US 8,426,194 B2
(45) Date of Patent: Apr. 23, 2013

(54) METHODS AND AGENTS FOR SCREENING FOR COMPOUNDS CAPABLE OF MODULATING VEGF EXPRESSION

(75) Inventors: Liangxian Cao, Parlin, NJ (US); Christopher Robert Trotta, Somerset, NJ (US)

(73) Assignee: PTC Therapeutics, Inc., South Plainfield, NJ (US)

( * ) Notice: Subject to any disclaimer, the term of this patent is extended or adjusted under 35 U.S.C. 154(b) by 1667 days.

(21) Appl. No.: 10/851,074

(22) Filed: May 24, 2004

(65) Prior Publication Data

US 2004/0214223 A1  Oct. 28, 2004

Related U.S. Application Data

(63) Continuation-in-part of application No. PCT/US2004/001643, filed on Jan. 21, 2004.

(60) Provisional application No. 60/441,637, filed on Jan. 21, 2003.

(51) Int. Cl.
*C12Q 1/68* (2006.01)
*C07H 21/04* (2006.01)

(52) U.S. Cl.
USPC ........ 435/320.1; 435/325; 435/69.1; 435/6.1; 506/13

(58) Field of Classification Search .................. None
See application file for complete search history.

(56) References Cited

U.S. PATENT DOCUMENTS

| | | | |
|---|---|---|---|
| 3,346,381 A | 10/1967 | Grieg | |
| 5,439,797 A | 8/1995 | Tsien et al. | |
| 5,444,149 A | 8/1995 | Keene et al. | |
| 5,587,300 A | 12/1996 | Malter | |
| 5,691,145 A | 11/1997 | Pitner et al. | |
| 5,698,427 A | 12/1997 | Keene et al. | |
| 5,700,660 A | 12/1997 | Leonard et al. | |
| 5,731,343 A | 3/1998 | Feng et al. | |
| 5,776,738 A | 7/1998 | Dell'Orco, Sr. et al. | |
| 5,843,770 A | 12/1998 | Ill et al. | |
| 5,849,520 A | 12/1998 | Leonard et al. | |
| 5,859,227 A | 1/1999 | Giordano et al. | |
| 5,908,779 A | 6/1999 | Carmichael et al. | |
| 5,928,888 A | 7/1999 | Whitney | |
| 5,990,298 A | 11/1999 | Carmichael et al. | |

(Continued)

FOREIGN PATENT DOCUMENTS

| | | |
|---|---|---|
| EP | 1176196 | 1/2002 |
| EP | 1 604 011 | 12/2005 |

(Continued)

OTHER PUBLICATIONS

Forsythe et al. (Molecular and Cellular Biology, 1996, vol. 16, No. 9, p. 4604-4613).*
Akiri et al. (Oncogene 1998, vol. 17, p. 227-236).*
Rapella et al. (Int. J. Cancer, 2002, vol. 99, p. 658-664).*
Iida et al. (Life Sciences, 2002, vol. 71, p. 1607-1614).*
Benjamin et al. (PNAS, 1997, vol. 94, p. 8761-8766).*
Cohen et al. (Journal of Biological Chemistry, 1996, 271(2), p. 736-741).*

(Continued)

*Primary Examiner* — Stephanie K Mummert
(74) *Attorney, Agent, or Firm* — Jones Day

(57) ABSTRACT

The invention relates to the fields of screening assays and compounds and methods for altering protein expression and levels of protein. In particular, the invention includes assays to screen for agents capable of modulating expression of VEGF and agents capable of modulating VEGF expression.

23 Claims, 8 Drawing Sheets

U.S. PATENT DOCUMENTS

| | | | |
|---|---|---|---|
| 6,004,749 | A | 12/1999 | Giordano et al. |
| 6,057,437 | A * | 5/2000 | Kamiya et al. ............... 536/24.5 |
| 6,107,029 | A | 8/2000 | Giordano |
| 6,159,709 | A | 12/2000 | Korneluk et al. |
| 6,171,821 | B1 | 1/2001 | Korneluk et al. |
| 6,203,982 | B1 | 3/2001 | Nunokawa et al. |
| 6,214,563 | B1 | 4/2001 | Negulescu et al. |
| 6,221,587 | B1 | 4/2001 | Ecker et al. |
| 6,221,612 | B1 | 4/2001 | Knapp et al. |
| 6,232,070 | B1 | 5/2001 | Shuman |
| 6,265,167 | B1 | 7/2001 | Carmichael et al. |
| 6,265,546 | B1 | 7/2001 | Cohen et al. |
| 6,284,882 | B1 | 9/2001 | Wu-Wong et al. |
| 6,303,295 | B1 | 10/2001 | Taylor et al. |
| 6,331,170 | B1 | 12/2001 | Ordway |
| 6,331,396 | B1 | 12/2001 | Silverman et al. |
| 6,399,373 | B1 | 6/2002 | Bougueleret |
| 6,448,007 | B1 | 9/2002 | Giordano et al. |
| 6,455,280 | B1 | 9/2002 | Edwards et al. |
| 6,465,176 | B1 | 10/2002 | Giordano et al. |
| 6,476,208 | B1 | 11/2002 | Cohen et al. |
| 6,528,060 | B1 | 3/2003 | Nicolette |
| 6,617,493 | B1 | 9/2003 | Fader |
| 6,627,797 | B1 | 9/2003 | Duvick et al. |
| 6,630,589 | B1 | 10/2003 | Giordano et al. |
| 6,635,671 | B1 | 10/2003 | Kastelic et al. |
| 6,638,522 | B1 | 10/2003 | Mulye |
| 6,645,747 | B1 | 11/2003 | Hallahan et al. |
| 6,653,132 | B1 * | 11/2003 | Keshet et al. ................. 435/375 |
| 6,667,152 | B2 | 12/2003 | Miles et al. |
| 6,872,850 | B2 | 3/2005 | Giordano et al. |
| 7,078,171 | B2 | 7/2006 | Giordano et al. |
| 7,371,726 | B2 | 5/2008 | Junker et al. |
| 7,601,840 | B2 | 10/2009 | Moon et al. |
| 7,767,689 | B2 | 8/2010 | Moon et al. |
| 2002/0006661 | A1 | 1/2002 | Green et al. |
| 2002/0132257 | A1 | 9/2002 | Giordano et al. |
| 2003/0135870 | A1 | 7/2003 | Cheikh et al. |
| 2003/0199453 | A1 | 10/2003 | Giordano et al. |
| 2004/0063120 | A1 | 4/2004 | Beer et al. |
| 2004/0091866 | A1 | 5/2004 | Giordano et al. |
| 2004/0138282 | A1 | 7/2004 | Greig et al. |
| 2004/0152117 | A1 | 8/2004 | Giordano et al. |
| 2004/0231007 | A1 | 11/2004 | Kastelic et al. |
| 2005/0048549 | A1 | 3/2005 | Cao et al. |
| 2007/0072186 | A1 | 3/2007 | Mehta et al. |
| 2007/0111203 | A1 | 5/2007 | Cao et al. |
| 2007/0254878 | A1 | 11/2007 | Cao et al. |
| 2008/0064683 | A1 | 3/2008 | Cao et al. |
| 2009/0068654 | A1 | 3/2009 | Kastelic et al. |

FOREIGN PATENT DOCUMENTS

| | | |
|---|---|---|
| EP | 1 761 638 | 3/2007 |
| GB | 9828707.1 | 12/1998 |
| GB | 9828709.7 | 12/1998 |
| WO | WO 93/20212 | 10/1993 |
| WO | WO 95/33831 | 12/1995 |
| WO | WO 97/25860 | 7/1997 |
| WO | WO 98/39484 | 9/1998 |
| WO | WO 00/04051 | 1/2000 |
| WO | WO 00/39314 | 7/2000 |
| WO | WO 00/46247 | 8/2000 |
| WO | WO 01/84155 | 8/2001 |
| WO | WO 02/48150 | 6/2002 |
| WO | WO 02/077609 | 10/2002 |
| WO | WO 02/083953 | 10/2002 |
| WO | WO 03/087815 A2 | 10/2003 |
| WO | WO 2004/065561 | 8/2004 |
| WO | WO 2005/049868 | 6/2005 |
| WO | WO2005095615 | 10/2005 |
| WO | WO 2005/118857 | 12/2005 |
| WO | WO 2006/022712 | 3/2006 |

OTHER PUBLICATIONS

Zhang et al. (Cancer Research, 2000, vol. 60, p. 3655-3661).*

Claffey et al. (Mol Biol Cell, 1998, vol. 9, 469-481).*

Akiri et al., "Regulation of Vascular Endothelial Growth Factor (VEGF) Expression is Mediated by Internal Initiation of Translation and Alternative Initiation of Transcription", Oncogene, 17:227-236 (1998).

Bornes et al., "Control of the Vascular Endothelial Growth Factor Internal Ribosome Entry Site (IRES) Activity and Translation Initiation by Alternatively Spliced Coding Sequences", The Journal of Biological Chemistry, 279(18):18717-18726 (2004).

Claffey et al., "Identification of a Human VPF/VEGF 3' Untranslated Region Mediating Hypoxia-Induced mRNA Stability", Molecular Biology of the Cell, 9:469-481 (1998).

Dreyfuss et al., "Messenger-RNA-Binding Proteins and the Messages They Carry", Nature Reviews Molecular Cell Biology, 3:195-205 (2002).

Huez et al., "Two Independent Internal Ribosome Entry Sites are Involved in Translation Initiation of Vascular Endothelial Growth Factor mRNA", Molecular and Cellular Biology, 18(11):6178-6190 (1998).

Kedersha et al., "Stress Granules: Sites of mRNA Triage that Regulate mRNA Stability and Translatability", Biochemical Society Transactions, 30(6):963-969 (2002).

Kozak, M., "Influences of mRNA Secondary Structure on Initiation by Eukaryotic Ribosomes", Proc. Natl. Acad. Sci. USA, 83:2850-2854 (1986).

Lai et al., "Evidence that Tristetraprolin Binds to AU-Rich Elements and Promotes the Deadenylation and Destabilization of Tumor Necrosis Factor Alpha mRNA", Molecular and Cellular Biology, 19(6):4311-4323 (1999).

Miller et al., "The Vascular Endothelial Growth Factor mRNA Contains an Internal Ribosome Entry Site", FEBS Letters, 434:417-420 (1998).

Stein et al., "Translation of Vascular Endothelial Growth Factor mRNA by Internal Ribosome Entry: Implications for Translation under Hypoxia", Molecular and Cellular Biology, 18(6):3112-3119 (1998).

Stoecklin et al., "A Constitutive Decay Element Promotes Tumor Necrosis Factor Alpha mRNA Degradation via an AU-Rich Element-Independent Pathway", Molecular and Cellular Biology, 23(10):3506-3515 (2003).

Trotta et al., "BCR/ABL Activates mdm2 mRNA Translation via the La Antigen", Cancer Cell, 3:145-160 (2003 ).

DeJong, Eric S., et al., "RNA and RNA-Protein Complexes as Targets for Therapeutic Intervention", Current Topics in Medicinal Chemistry 2002, vol. 2, No. 3, pp. 289-302.

Ge et al., "Regulation of Promoter Activity of the APP Gene by Cytokines and Growth Factors", Ann. N.Y. Acad. Sci 973:463-467 (2002).

de Wet et al., "Firefly Luciferase Gene: Structure and Expression in Mammalian Cells", Molecular and Cellular Biology 7(2):725-737 (1987).

Grens et al., "The 5' and 3'-Untranslated Regions of Ornithine Decarboxylase mRNA Affect the Translational Efficiency", "The Journal of Biological Chemistry", 265(20):11810-11816 (1990).

International Search Report dated Nov. 6, 2007 issued in PCT/US04/20751.

Tischer et al., "The Human Gene for Vascular Endothelial Growth Factor", The Journal of Biological Chamistry, 266(18):11947-11954 (1991).

U.S. Appl. No. 11/079,420, Young-Choon Moon et al., filed Mar. 15, 2005.

U.S. Appl. No. 11/107,783, Young-Choon Moon et al., filed Apr. 18, 2005.

U.S. Appl. No. 11/735,069, Liangxian Cao et al., Apr. 13, 2007.

U.S. Appl. No. 11/765,871, Liangxian Cao et al., Jun. 20, 2007.

U.S. Appl. No. 60/977,612.

International Search Report, dated Jun. 2, 2005, in the PCT Application No. PCT/US04/038496.

International Preliminary Report on Patentability, dated Jul. 17, 2008, in the PCT Application No. PCT/US04/038496.

Written Opinion of the International Searching Authority, dated May 17, 2006, in the PCT Application No. PCT/US04/038496.

Response to Non-Final Rejection filed Jul. 17, 2009 in U.S. Appl. No. 10/543,033.

Restriction/Election Requirement, dated Jan. 26, 2009, in U.S. Appl. No. 10/579,500.

Response to Restriction/Election Requirement, dated Jun. 26, 2009, in U.S. Appl. No. 10/579,500.
Restriction/Election Requirement, dated Aug. 6, 2009, in U.S. Appl. No. 10/579,500.
Response to Restriction/Election Requirement, dated Sep. 4, 2009, in U.S. Appl. No. 10/579,500.
Request for Continued Examination and Amendment, dated Jun. 16, 2009 in U.S. Appl. No. 10/895,393.
Restriction Requirement mailed Sep. 3, 2009 in U.S. Appl. No. 10/895,393.
Asano et al., 1997, "The translation initiation factor eIf3-p48 subunit is encoded by int-6, a site of frequent integration by the mouse mammary tumor virus genome." J. Biol. Chem. 272(38):23477-80.
Child et al., 1999, "Cell type-dependent and -independent control of HER-2/neu translation" Int Journal of Biochem & Cell Biol 31:201-213.
Hoover et al., 1997, "Pim-1 protein expression regulated by its 5'-untranslated region and translation initiation factor eIF-4E", Cell Growth Differ., 8:1371-1380.
Horvath et al., "Multiple elements in the 5' untranslated region down-regulate c-sis messenger RNA translation", Cell Growth & Diff., 6: 1103-1110.
Kowalski and Mager, 1998, "A human endogenous retrovirus suppresses translation of an associated fusion transcript, PLA2L", J. Virol., 72(7):6164-8.
Lal et al., 2004, "Concurrent Versus Individual Binding of HuR and AUF1 to Common Labile Target, mRNA's" EMBO J. 23:3092-3102.
Li et al., 2001, "Targeting HER-2/neu-overexpressing breast cancer cells by an antisense iron responsive element-directed gene expression." Cancer Letters 174(2):151-58.
Mehta et al, 2006, "Derepression of the Her-2 uORF is mediated by a novel post-transcriptional control mechanism in cancer cells." Genes & Dev, 20:939-953.
Millard et al., 2000, "A U-Rich Element in the 5' Untranslated Region if necessary for the Translation of p27 mRNA" Molec & Cell. Biol. 20(16):5947-5959.
Morris et al., 2000, "Upstream Open Reading Frames as Regulators of mRNA translation," Molec & Cell, Biol. 20(23):8635-8642.
Pesole et al., 2001, "Structural and Functional Features of Eukaryotic mRNA Untranslated Regions," Gene 276:73-81.
Pontrelli et al., 2004, "Translational control of apolipoprotein B mRNA: regulation via cis elements in the 5' and 3' untranslated regions", Biochemistry, 43(21):6734-44.
Sachs & Geballe, 2006, "Downstream control of upstream open reading frames," Genes & Dev. 20:915-921.
Response to Restriction/Election Requirement, dated Dec. 2, 2009 in U.S. Appl. No. 10/895,393.
Non-Final Rejection, dated Feb. 18, 2010 in U.S. Appl. No. 10/895,393.
Response to Non-Final Office Action, dated Aug. 17, 2010 in U.S. Appl. No. 10/895,393.
Non-Final Rejection, dated Jan. 5, 2010, in U.S. Appl. No. 10/579,500.
Notice of Abandonment, dated Aug. 31, 2010, in U.S. Appl. No. 10/579,500.
Final Rejection, dated Jan. 13, 2010, in U.S. Appl. No. 10/543,033.
Response, dated Jul. 13, 2010, in U.S. Appl. No. 10/543,033.
Communication from the Examining Division, dated Jan. 29, 2010, issued in EP 04704085.2 (EP 1604011).
International Search Report, dated Jul. 3, 2005, in the PCT Application No. PCT/US04/038496.
Non-Final Rejection, dated Feb. 4, 2011 in U.S. Appl. No. 10/543,033.
Non-Final, Rejection, dated Feb. 15, 2011 in U.S. Appl. No. 10/895,393.
Adams et al., 1998, "Localized infusion of IGF-I results in skeletal muscle hypertrophy in rats." J Appl Physiol, 84:1716-1722.
Barton et al., 2002, "Muscle-specific expression of insulin-like growth factor I counters muscle decline in mdx mice", J. Cell Biol., 157:137-148.
Barton-Davis, 1998, "Viral mediated expression of insulin-like growth factor I blocks the aging-related loss of skeletal muscle function", PNAS, 95:15603-15607.
Bogdanovich et al., 2004, "Therapeutics for Duchenne muscular dystrophy: current approaches and future directions", J Mol Med., 82(2):102-15.
Burkin and Kaufman, 1999, "The α7β1 integrin in muscle development and disease", Cell Tissue Res., 296:183-190.
Chakkalakal et al., 2005, "Molecular, cellular, and pharmacological therapies for Duchenne/Becker muscular dystrophies", FASEB J., 19(8):880-91.
Coleman et al., 1995, "Myogenic Vector Expression of Insulin-like Growth Factor I Stimulates Muscle Cell Differentiation and Myofiber Hypertrophy in Transgenic Mice", J. Biol. Chem., 270:12109-12116.
Davies and Nowak, 2006, "Molecular Mechanisms of Muscular Dystrophies: Old and New Players", Nature, 7:762-773 (Supplementary Information Included).
Engvall et al., 2003, "The new frontier in muscular dystrophy research: booster genes", FASEB J., 17: 1579-1584.
Gramolini et al., 2001, "Distinct regions in the 3' untranslated region are responsible for targeting and stabilizing utrophin transcripts in skeletal muscle cells", J Cell Biol, 154:1173-1183.
Gramolini, 2001, "Increased expression of utrophin in a slow vs. a fast muscle involves posttranscriptional events", Am J Physiol Cell Physiol., 281(4):C1300-9.
Kambadur et al., 1997,"Mutations in myostatin (GDF8) in double-muscled Belgian Blue and Piedmontese cattle", Genome Res., 7(9):910-6.
Karin et al., 2006, "Role for IKK2 in muscle: waste not, want not", J Clin Invest., 116: 2866-2868.
Krag et al., 2004, "Heregulin ameliorates the dystrophic phenotype in mdx mice", PNAS, 101: 13856-13860.
Nowak and Davies, 2004, "Duchenne Muscular Dystrophy and dystrophin: pathogenesis and opportunities for treatment", EMBO Reports, 5:872-876.
Ohlendieck and Campbell, 1991, "Dystrophin-associated proteins are greatly reduced in skeletal muscle from mdx mice", J Cell Biol, 115:1685-1694.
Patel et al, 2005, "Molecular mechanisms involving IGF-1 and myostatin to induce muscle hypertrophy as a therapeutic strategy for Duchenne Muscular Dystrophy", Acta Myol., 24(3):230-41.
Tobin et al., 2005, "Myostatin, a negative regulator of muscle mass: implications for muscle degenerative diseases", Curr Opin Pharmacol., 5(3):328-32.
Vachon et al.,1997, "Integrins (alpha7beta1) in muscle function and survival. Disrupted expression in merosin-deficient congenital muscular dystrophy", J Clin Invest., 100(7):1870-81.
Veyrune et al., 1996, "A localisation signal in the 3' untranslated region of c-myc mRNA targets c-myc mRNA and beta-globin reporter sequences to the perinuclear cytoplasm and cytoskeletal-bound polysomes", J Cell Sci, 109:1185-1194.
Avila et al., 2007 "Trichostatin A increases SMN expression and survival in a mouse model of spinal muscular atrophy", J Clin Invest. ;117(3):659-71.
Bertini et al., 2005, "134th ENMC International Workshop: Outcome Measures and Treatment of Spinal Muscular Atrophy, Feb. 11-13, 2005, Naarden, The Netherlands", Neuromuscul Disord. 15(11):802-16.
Boda et al., 2004, "Survival motor neuron SMN1 and SMN2 gene promoters: identical sequences and differential expression in neurons and non-neuronal cells", Eur J Hum Genet,: 12(9):729-37.
Brahe et al., 2005, "Phenylbutyrate increases SMN gene expression in spinal muscular atrophy patients", Eur J Hum Genet.; 13(2):256-9.
Echaniz-Laguna et al., 1999, "The promoters of the survival motor neuron gene (SMN) and its copy (SMNc) share common regulatory elements", Am J Hum Genet; 64(5):1365-70.
Germain-Desprez et al., 2001, "The SMN genes are subject to transcriptional regulation during cellular differentiation", Gene, 279:109-117.
Iannaconne et al., 2002 "Outcome Measures for Pediatric Spinal Muscular Atrophy", Arch Neurol. 59:1445-1450.
Iannaconne et al., 2003, "Reliability of 4 Outcome Measures in Pediatric Spinal Muscular Atrophy", Arch Neurol; 60:1130-1136.

Jareckl et al., 2005 "Diverse small-molecule modulators of SMN expression found by high-throughput compound screening: early leads towards a therapeutic for spinal muscular atrophy", Hum Mol Genet.; 14(14):2003-18.

Kolb et al., 2006, "A novel cell immunoassay to measure survival of motor neurons protein in blood cells", BMC Neurology, 6:6.

Lunn et al., 2004, "Indoprofen upregulates the survival motor neuron protein through a cyclooxygenase-independent mechanism", Chem Biol.; 11(11):1489-93.

Merlini et al., 2003, "Role of gabapentin in spinal muscular atrophy: results of a multicenter, randomized Italian study", J Child Neurol.; 18(8):537-41.

Monani et al., 1999, Promoter analysis of the human centromeric and telomeric survival motor neuron genes (SMNC and SMNT), Biochim Biophys Acta; 1445(3):330-6.

Sumner., 2006, "Therapeutics development for spinal muscular atrophy", NeuroRx.; 3(2):235-45.

Wan, 2005, "The survival of motor neurons protein determines the capacity for snRNP assembly: biochemical deficiency in spinal muscular atrophy", Molec & Cell Biol, 25(13): 5543-5551.

Wolstencroft et al., 2005, "A non-sequence-specific requirement for SMN protein activity: the role of aminoglycosides in inducing elevated SMN protein levels", Hum Mol Genet, 14(9):1199-1210.

Zhang et al., 2001, "An in vivo reporter system for measuring increased inclusion of exon 7 in SMN2 mRNA: potential therapy of SMA", Gene Ther., (20):1532-1538.

Gubitz et al., 2004 "The SMN complex", Exp Cell Res.; 296:51-6.

Paushkin et al.., 2002 "The SMN complex, an assemblyosome of ribonucleoproteins" Curr Opin Cell Biol., 14:305-12.

Sumner et al., 2006, "SMN mRNA and protein levels in peripheral blood: biomarkers for SMA clinical trials", Neurology, 66:1067-1073.

Yong et al., 2004, "Why do cells need an assembly machine for RNA-protein complexes?" Trends Cell Biol.; 15(5):226-32.

Adams et al., 1991, "Fluorescence ratio imaging of cyclic AMP in single cells" Nature 349:694-697.

Afouda et al., 1999, "Localized X1d3 mRNA activation in Xenopus embryos by cytoplasmic polyadenylation" Mech Dev 88(1):15-31.

Aharon & Schneider, 1993. "Selective destabilization of short-lived mRNAs with the granulocyte-macrophage colony-stimulating factor AU-rich 3' noncoding region is mediated by a cotranslational mechanism" Mol. Cell. Biol. 13: 1971-1980.

Akashi et al., 1994. "Number and location of AUUUA motifs: Role in regulating transiently expressed RNAs." Blood 83:3182-3187 Am Soc. of Hemat.

Amara et al., 1999, "TGF-beta(1), regulation of Alzheimer amyloid precursor protein mRNA expression in a normal human astrocyte cell line: mRNA stabilization." Brain Res. Mol. Brain Res. 71(1):42-49.

Auwerx, 1991, "The human leukemia cell line, THP-1: A multifaceted model for the study of monocyte-macrophage differentiation." Experientia 47:22-31 Birkhauser Verlag Basel.

Banholzer et al., 1997, "Rapamycin destabilizes interleukin-3 mRNA in autocrine tumor cells by a mechanism requiring an intact 3' untranslated region." Molecular and Cellular Biology 17: 3254-3260.

Bardoni & Mandel, 2002, "Advances in understanding of fragile X pathogenesis and FMRP function, and in identification of X linked mental retardation genes." Curr. Opin. Genet. Dev. 12(3):284-293.

Barkoff et al., 2000, "Translational control of cyclin B1 mRNA during meiotic maturation: coordinated repression and cytoplasmic polyadenylation" Dev Biol. 220(1):97-109.

Bashaw & Baker, 1995, "The msl-2 dosage compensation gene of *Drosophila* encodes a putative DNA-binding protein whose expression is sex specifically regulated by Sex-lethal." Develop. 121(10):3245-3258.

Beelman & Parker, 1994, "Differential effects of translational inhibition in cis and in trans on the decay of the unstable yeast MFA2 mRNA." J. Biol. Chem, 269:9687-9692.

Bergsten & Gavis, 1999, "Role for mRNA localization in translational activation but not spatial restriction of nanos RNA." Develop. 126(4):659-669.

Beutler et al., 1988, "Assay of ribonuclease that preferentially hydrolyses mRNAs containing cytokine-derived UA-rich instability sequences." Biochem. Biophys Res. Commun. 152:973-980.

Bhattacharyya et al., 2007, "Mining the GEMS—a novel platform technology targeting post-transcriptional control mechanisms", Drug Discovery Today 12:553-560.

Bock et al., 1992, "Selection of single-stranded DNA molecules that bind and inhibit human thrombin." Nature 355:564-566.

Brenchley, 1998, "Antagonizing the expression of VEGF in pathological angiogenesis," Exp. Opin Ther. Patents 8(12): 1695-1706.

Brennan & Steitz, 2001, "HuR and mRNA stability." Cell. Mol. Life. Sci. 58:266-277.

Carballo et al., 1998, "Feedback inhibition of macrophage tumor necrosis factor-alpha production by tristetraprolin." Science 281:1001-1005.

Castagnetti et al., 2000. "Control of oskar mRNA translation during by Bruno in a novel cell-free system from *Drosophila* ovaries." Develop. 127(5):1063-1068.

Charlesworth et al., 2000, "The temporal control of Wee1 mRNA translation during *Xenopus oocyte* maturation is regulated by cytoplasmic polyadenylation elements within the 3'-untranslated region." Dev. Biol. 227(2): 706-719.

Chen et al., 1994, "Selective degradation of early-response-gene mRNAs: Functional analyses of sequence features of the AU-rich elements." Mol. Cell. Biol. 14: 8471-8482.

Chen et al., 1994, "Interplay of two functionally and structurally distinct domains of the c-fos AU-rich element specifies its mRNA-destabilizing function." Mol. Cell. Biol. 14:416-426.

Chen et al., 1995, "AU-rich elements: characterization and importance in mRNA degradation" Trends Biochem. Sci. 20:465-470.

Chen et al., 1995, "mRNA decay mediated by two distinct AU-rich elements from c-fos and granulocyte-macrophage colony-stimulating factor transcripts: different deadenylation kinetics and uncoupling from translation." Mol. Cell. Biol. 15:5777-5788.

Chen et al., 2001, "AU binding proteins recruit the exosome to degrade ARE-containing mRNAs" Cell 107:451-464.

Cho et al., 2002, "Emerging techniques for the discovery and validation of therapeutic targets for skeletal diseases" Expert Opin. Ther. Targets 6(6):679-689.

Clark et al., 2000, "Synthesis of the posterior determinant Nanos is spatially restricted by a novel cotranslational regulatory mechanism." Curr. Biol. 10(20):1311-1314.

Clark et al., 2002, "A common translational control mechanism functions in axial patterning and neuroendocrine signaling in *Drosophila*." Develop. 129(14): 3325-3334.

Cohen et al., 1996, "CN1-1493 inhibits monocyte/macrophage tumor necrosis factor by suppression of translation efficiency." Proc. Natl. Acad. Sci. USA 93:3967-3971.

Crawford et al., 1997, "The role of 3' poly (A) tail metabolism in tumor necrosis factor-α regulation." J. Biol. Chem. 272:21120-21127. The Am Soc of Biochem. And Molec. Biol.

Crosio et al., 2000, "La protein has a positive effect on the translation of TOP mRNAs in vivo." Nucl. Acids. Res. 28(15):2927-34.

Crucs et al., 2000, "Overlapping but distinct RNA elements control repression and activation of nanos translation." Mol. Cell. 5(3):457-467.

Curatola et al., 1995, "Rapid degradation of AU-rich element (ARE) mRNAs is activated by ribosome transit and blocked by secondary structure at any position 5' to the ARE." Mol. Cell. Biol. 15:6331.

Dahanukar & Wharton, 1996, "The Nanos gradient in *Drosophila* embryos is generated by translational regulation." Genes Dev 20:2610-2620.

Danner et al., 1998, "Agonist regulation of human beta$_2$-adrenergic receptor mRNA stability occurs via a specific AU-rich element," J. Biol. Chem. 273(6):3223-3229.

De Jong et al., 2002, "RNA and RNA-protein complexes as targets for therapeutic intervention", Curr. Topics Medicinal Chem. 2:289-302.

Dias et al., 1994, "Chemical probe for glycosidic conformation in telomeric DNAs" J. Am. Chem. Soc. 116:4479-4480.

Diener & Moore, 1998. "Solution structure of a substrate for the archael pre-tRNA splicing endonucleases: The bulge-helix-bulge motif." Mol. Cell. 1:883-894.

Dominski & Marzluff, 1999, "Formation of the 3' end of histone mRNA." Gene 239(1):1-14.

Eibl et al., 1999, "In vivo analysis of plastid psbA, rbcL and rpl32 UTR elements by chloroplast transformation: tobacco plastid gene expression is controlled by modulation of transcript levels and translation efficiency", Plant J. 19:333-345.
Fan et al., 1998, "Overexpression of HuR, a nuclear-cytoplasmic shuttling protein, increases the in vivo stability of ARE-containing mRNAS." EMBO J 17:3448-3460.
Fortes et al., 2003, "Inhibiting expression of specific genes in mammalian cells with 5' end-mutated U1 small nuclear RNAs targeted to terminal exons of pre-mRNA", Proc. Natl. Acad. Sci. USA 100:8264-8269.
Fruscoloni et al., 2001, "Cleavage of non-tRNA substrates by eukaryal tRNA splicing endonucleases." EMBO Rep 2(3):217-221.
Gan et al., 1998, "Functional characterization of the internal ribosome entry site of eIF4G mRNA" J. Biol. Chem. 273:5006-5012.
Gavis et al., 1996, "A conserved 90 nucleotide element mediates translational repression of nanos RNA. Development. Sep. 1996:122( 9):2791-800." Develop. 122(9):2791-2800.
Ge et al., 2002, "Regulation of promoter activity of the APP gene by cytokines and growth factors: implications in Alzheimer's disease", Ann. N.Y. Acad. Sci. 973:463-467.
Gebauer et al., 1998, "The *Drosophila* splicing regulator sex-lethal directly inhibits translation of male-specific-lethal 2 mRNA" RNA 4(2):142-150.
Genbank Accession No. NM_0017 ev 25, dated Oct. 22, 2006.
Genbank Accession No. NM_0029 ev 25, dated Aug. 20, 2006.
Genbank Accession No. NM_006536, dated Sep. 17, 2006.
Genbank Accession No. AF022375, dated Oct. 7, 1998.
Genbank Accession No. AJI31730, dated Apr. 15, 2005.
Genbank Accession No. MI1567, dated Oct. 30, 1994.
Genbank Accession No. MI4745, dated Apr. 27, 1993.
Genbank Accession No. MI4758, dated Dec. 3, 1999.
Genbank Accession No. M33680, dated Aug. 3, 1993.
Genbank Accession No. M54968, dated Feb. 4, 1997.
Genbank Accession No. M90100, dated Dec. 31, 1994.
Genbank Accession No. NM_0002 30, dated Mar. 5, 2006.
Genbank Accession No. NM_0017 28, dated Feb. 26, 2006.
Genbank Accession No. NM_0027 74, dated Feb. 12, 2006.
Genbank Accession No. NM_0052 51, dated Feb. 12, 2006.
Genbank Accession No. NM_0807 06, dated Mar. 2, 2006.
Genbank Accession No. NM_0001 62, dated Jan. 15, 2006.
Genbank Accession No. NM_0002 08. dated Feb. 24, 2006.
Genbank Accession No. NM_0002 47, dated Feb. 27, 2006.
Genbank Accession No. NM_0003 21, dated Mar. 5, 2006.
Genbank Accession No. NM_0004 18, dated Feb. 12, 2006.
Genbank Accession No. NM_0005 27, dated Jan. 15, 2006.
Genbank Accession No. NM_0005 72, dated Mar. 5, 2006.
Genbank Accession No. NM_0005 89, dated Mar. 5, 2006.
Genbank Accession No. NM_0006 65, dated Feb. 28, 2006.
Genbank Accession No. NM_000600, dated Mar. 5, 2006.
Genbank Accession No. NM_0007 58, dated Feb. 12, 2006.
Genbank Accession No. NM_0007 84, dated Nov. 27, 2005.
Genbank Accession No. NM_0007 91, dated Nov. 6, 2005.
Genbank Accession No. NM_0007 99, dated Jan. 29, 2006.
Genbank Accession No. NM_0008 99, dated Nov. 27, 2005.
Genbank Accession No. NM_0008 ev 75, dated Apr. 10, 2009.
Genbank Accession No. NM_0009 48, dated Feb. 26, 2006.
Genbank Accession No. NM_0011 45, dated Mar. 5, 2006.
Genbank Accession No. NM_001 168, dated Mar. 5, 2006.
Genbank Accession No. NM_0012 40, dated Feb. 26, 2006.
Genbank Accession No. NM_0015 65, dated Jan. 29, 2006.
Genbank Accession No. NM_0015 67, dated Jan. 29, 2006.
Genbank Accession No. NM_001917, dated Jan. 29, 2006.
Genbank Accession No. NM_002006, dated Oct. 1, 2006.
Genbank Accession No. NM_002087, dated Oct. 18, 2005.
Genbank Accession No. NM_0021 11, dated Feb. 19, 2006.
Genbank Accession No. NM_0021 51, dated Jan. 8, 2006.
Genbank Accession No. NM_002231, dated Nov. 27, 2005.
Genbank Accession No. NM_002392, dated Mar. 5, 2006.
Genbank Accession No. NM_0026 ev 32, dated Aug. 20, 2006
Genbank Accession No. NM_0029 63, dated Feb. 26, 2006.
Genbank Accession No. NM_0029 86, dated Nov. 6, 2005.
Genbank Accession No. NM_0029 ev 64, dated Oct. 22, 2006.
Genbank Accession No. NM_0032 55, dated Mar. 4, 2006.
Genbank Accession No. NM_0032 56. dated Mar. 4, 2006.
Genbank Accession No. NM_0033 55, dated Jan. 29, 2006.
Genbank Accession No. NM_0036 42, dated Sep. 24, 2005.
Genbank Accession No. NM_0038 ev 83, dated Oct. 29, 2006.
Genbank Accession No. NM_004364, dated Jan. 29, 2006.
Genbank Accession No. NM_004395, dated Oct. 16, 2005.
Genbank Accession No. NM_0047 95, dated Feb. 26, 2006.
Genbank Accession No. NM_0047 97, dated Mar. 5, 2006.
Genbank Accession No. NM_0052 52, dated Jan. 29, 2006.
Genbank Accession No. NM_0054 ev I7, dated Apr. 19, 2009.
Genbank Accession No. NM_0059 31, dated Oct. 16, 2005.
Genbank Accession No. NM_007310, dated Jan. 29, 2006.
Genbank Accession No. NM_000794, dated Sep. 17, 2006.
Genbank Accession No. NM_000134, dated Oct. 15, 2006.
Genbank Accession No. NM_0187 ev 27, dated Mar. 1, 2009.
Genbank Accession No. NM_0204 15, dated Jan. 29, 2006.
Genbank Accession No. NM_0326 11, dated Mar. 4, 2006.
Genbank Accession No. NM_053056, dated Feb. 26, 2006.
Genbank Accession No. NM_0784 67, dated Mar. 5, 2006.
Genbank Accession No. NM_0807 04, dated Mar. 2, 2006.
Genbank Accession No. NM_0807 05 , dated Mar. 2, 2006.
Genbank Accession No. NM_080881, dated Oct. 17, 2005.
Genbank Accession No. NM_138712, dated Mar. 5, 2006.
Genbank Accession No. NM_1389 92, dated Feb. 12, 2006.
Genbank Accession No. NM_1393 ev 17, dated Oct. 29, 2006.
Genbank Accession No. S48568, dated Apr. 17, 2002.
Genbank Accession No. U22431, dated Jun. 28, 1995.
Genbank Accession No. U25676, dated Jul. 20, 1995.
Genbank Accession No. X16302, dated Apr. 18, 2005.
Genbank Accession No. XM_589987, dated Sep. 30, 2005.
Genbank Accession No. XM_001831, dated May 8, 2002.
Genbank Accession No: XM_003061, dated May 8, 2002.
Genbank Accession No: XM_003751, dated Oct. 16, 2001.
Genbank Accession No: XM_015547, dated Aug. 1, 2002.
Genbank Accession No: X01394, dated Mar. 21, 1995.
Genbank Accession No: X00588.1, dated Mar. 30, 1995.
Gil et al., 1996, "Multiple regions of the *Arabidopsis* SAUR-AC1 gene control transcript abundance: the 3' untranslated region functions as an mRNA instability determinant." EMBO J 15:1678-1686.
Goodwin et al., 1993, "Translational regulation of tra-2 by its 3' untranslated region controls sexual identity in *C. elegans*." Cell 75:329-339.
Goodwin et al., 1997, "A genetic pathway for regulation of tra-2 translation" Develop. 124:749-758.
Green et al., 2002, "Crystallization and characterization of Smaug: a novel RNA-binding motif." Biochem. Biophys. Res. Commun. 297(5):1085-1088.
Guhaniyogi & Brewer, 2001, "Regulation of mRNA stability in mammalian cells." Gene 265(1-2):11-23.
Haag & Kimble, 2000, "Regulatory elements required for development of *Caenorhabditis elegans* hermaphrodites are conserved in the tra-2 homologue of *C. remanei*, a male/female sister species" Genetics 155(1):105-116.
Heaton et al., 1998, "Cyclic nucleotide regulation of type-I plasminogen activator-inhibitor mRNA stability in rat hepatoma cells. Identification of cis-acting sequences." J Biol. Chem. 273:14261-14268.
Huang et al., 1990, "Intervening sequences increase efficiency of RNA 3' processing and accumulation of cytoplasmic RNA", Nucl. Acids Res. 18:937-947.
Hubert et al., 1996, "RNAs mediating cotranslational insertion of selenocysteine in eukaryotic selenoproteins" Biochimie 78(7):590-596.
Hyder et al., 2000, "Identification of functional estrogen response elements in the gene coding for the potent angiogenic factor vascular endothelial growth factor," Cancer Res 60:3183-3190.
Ikemura, 1985, "Codon usage and tRNA content in unicellular and multicellular organisms." Mol. Biol. Evol., 2(1):13-34.
Ikemura and Okeki, 1983, "Codon usage and transfer RNA contents: organism-specific codon-choice patterns in reference to the isoacceptor contents." Cold Spring Harbor Symp. Quant. Biol. 47:1087-1097.

Ismail et al., 2000, "Split-intron retroviral vectors: enhanced expression with improved safety", J. Virol. 74:2365-2371.

Jan et al., 1997, "Conservation of the *C.elegans* tra-2 3'UTR translational control." EMBO J 16(20):6301-6313.

Jan et al., 1999, "The STAR protein, GLD-1, is a translational regulator of sexual identity in *Caenorhabditis elegans*." EMBO J. 18:258-269.

Kakegawa et al., 2002, "Rapamycin induces binding activity to the terminal oligopyrimidine tract of ribosomal protein mRNA in rats." Arch Biochem Biophys 402(1):77-83.

Kastelic et al., 1996, "Induction of rapid IL-I beta mRNA degradation in THP-1 cells mediated through the AU-rich region in the 3'UTR by a radicicol analogue." Cytokine 8: 751-761.

Keene & Tenenbaum, 2002, "Eukaryotic mRNPs may represent post-transcriptional operons" Mol. Cell. 9:1161-1167.

Kelly et al., 1996, "Reconciliation of the X-ray and NMR structures of the thrombin-binding aptamer d(GGTTGGTGTGGTTGG)." J. Mol. Biol. 256:417-422.

Kemeny et al., 1998, "The tetravalent guanylhydrazone CNI-1493 blocks the toxic effects of interleukin-2 without diminishing antitumor efficacy." Proc. Natl. Acad. Sci. USA 95: 4561-4566.

Kim et al., 2002, "The human elongation factor 1 alpha (EF-I alpha) first intron highly enhances expression of foreign genes from the murine cytomegalovirus promoter." J. Biotechnol. 93(2):183-187.

Kimble, 1988, "fog-2, a germ-line-specific sex determination gene required for hermaphrodite spermatogenesis in *Caenorhabditis elegans*." Genetics, 119:43-61.

Klausner et al., 1993, "Regulating the fate of mRNA: The control of cellular iron metabolism" Cell 72:19-28.

Kleman-Leyer et al., 1997, "Properties of *H. volcanii* tRNA intron endonuclease reveal a relationship between the archaeal and eucaryal tRNA intron processing systems." Cell., 89:839-847.

Kobayashi et al., 1998, "Characterization of the 3' untranslated region of mouse DNA topoisomerase IIα mRNA," Gene 215:329-337.

Koeller et al., 1991, "Translation and the stability of mRNAs encoding the transferrin receptor and c-fos." Proc. Natl. Acad. Sci. 88:7778.

Lagnado et al., 1994, "AUUUA is not sufficient to promote Poly(A) shortening and degradation of an mRNA: the functional sequence within the AU-rich elements may be UUAUUUA(U/A) (U/A)" Mol. Cell. Biol. 14: 7984-7995.

Le & Maizel, 1989, "A method for assessing the statistical significance of RNA folding" J. Theor Biol. 138:495-510.

Lemm et al., 2002, "Regulation of c-myc mRNA decay by translational pausing in a coding region instability determinant", Mol. Cell. Biol. 22:3959-3969.

Levy et al., 1995, "Sequence and functional characterization of the terminal exon of the human insulin receptor gene." Biochem Biophys Acta 1263:253-257.

Levy et al., 1996, "Post-transcriptional regulation of vascular endothelial growth factor by hypoxia." J. Biol. Chem. 271:2746-2753.

Levy et al., 1998, "Hypoxic stabilization of vascular endothelial growth factor mRNA by the RNA-binding protein HuR." J Biol. Chem. 273(11):6417-6423.

Lewis et al., 1998, "Mapping of a minimal AU-rich sequence required for lipopolysaccharide-induced binding of a 55-kDa protein on tumor necrosis factor-α mRNA." J Biol. Chem. 273:13781-13786.

Li & Abelson, 2000, "Crystal structure of a dimeric archaeal splicing endonuclease." J. Mol. Biol. 302:639-648.

Li et al., 1998, "Crystal structure and evolution of a transfer RNA splicing enzyme" Science 280(536I):279-284.

Lykke-Andersen. J. & Garrett, R.A.., 1997, "RNA-protein interactions of an archaeal homotetrameric splicing endoribonuclease with an exceptional evolutionary history." EMBO J 16(20):6290-6300.

Macaya et al., 1993. "Thrombin-binding DNA aptamer forms a unimolecular quadruplex structure in solution." Proc. Natl. Acad. Sci. 90:3745-3749.

Muhlrad et al., 1995, "Turnover mechanisms of the stable yeast PGKI mRNA." Mol. Cell. Biol. 15(4):2145-2156.

Mukherjee et al., 2002, "The mammalian exosome mediates the efficient degradation of mRNAs that contain AU-rich elements." EMBO J. 21:165-174.

Nanbru et al., 1995, "Alternative translation of the proto-oncogene c-myc by an internal ribosome entry site." J. Biol. Chem. 272:32061-32066.

Nanbu et al., 1994, "Multiple instability-regulating sites in the 3' untranslated region of the urokinase-type plasminogen activator mRNA." Mol. Cell. Biol. 14:4920-4928.

Nishimori et al., 2004, "Involvement of the 3'-untranslated region of cyclooxygenase-2 gene in its post-transcriptional regulation through the glucocorticoid receptor", Life Sciences 74:2505-2513.

Oh et al., 1992, "Homeotic gene Antennapedia mRNA contains 5'-noncoding sequences that confer translational initiation by internal ribosome binding." Genes Dev 6:1643-1653.

Ostareck-Lederer et al., 2002, "c-Src-mediated phosphorylation of hnRNP K drives translational activation of specifically silenced mRNAs" Mol. Cell. Biol. 22(13):4535-4543.

Paynton & Bachvarova, 1994, "Polyadenylation and deadenylation of maternal mRNAs during oocyte growth and maturation in the mouse" Mol. Reprod. Dev 37(2): 172-180.

Pelletier & Soneberg, 1988, "Internal initiation of translation of eukaryotic mRNA directed by a sequence derived from poliovirus RNA" Nature 334:320-325.

Peterlin et al., 1993, "Tat Trans-Activator." In: Human Retroviruses; Cullen, Ed.; Oxford University Press: New York, pp. 75-100.

Piecyk et al., 2000, "TIA-1 is a translational silencer that selectively regulates the expression of TNF-alpha" EMBO J. 19:4154.

Qin & Pyle, 1999, "Site-specific labeling of RNA with fluorophores and other structural probes." Methods 18 (1):60-70.

Rajagopalan & Malter, 2000, "Growth factor-mediated stabilization of amyloid precursor protein mRNA is mediated by a conserved 29-nucleotide sequence in the 3'-untranslated region." J. Neurochem. 74(1):52-59.

Raught et al. 2000, "Regulation of ribosomal recruitment in eukaryotes" in: "Translational Control of Gene Expression." Sonenberg, Hershey and Mathews. eds. Cold Spring Harbor Laboratory Press. Ch. 6. pp. 245-293.

Reinmann et al., 2002, "Suppression of 15-lipoxygenase synthesis by hnRNP EI is dependent on repetitive nature of LOX mRNA 3'-UTR control element DICE." J. Mol. Biol 315(5):965-974.

Reyes & Abelson 1988, "Substrate recognition and splice site determination in yeast tRNA splicing." Cell 55:719-730.

Rogers et al., 2002, "An iron-responsive element type II in the 5'-untranslated region of the Alzheimer's amyloid precursor protein transcript." J. Biol. Chem. 277(47):45518-45528.

Sachs, 1993, "Messenger RNA degradation in eukaryotes." Cell 74:413-421.

Sambrook et al., 1989, "Standard protocol for calcium phosphate-mediated transfection of adherent cells." Molec. Cloning 16.33-16.37.

Sarkar & Hopper., 1998, "tRNA nuclear export in *Saccharomyces cerevisiae*: In situ hybridization analysis." Mol. Cell. Biol 9:3041-3055.

Savant-Bhonsale et al., 1992, "Evidence for instability of mRNAs containing AUUUA motifs mediated through translation-dependent assembly of a > 20S degradation complex" Genes Dev. 6:1927-1939.

Saxena et al., 1992, "Angiogenin is a cytotoxic, tRNA-specific ribonuclease in the RNase A superfamily." J. Biol. Chem. 267(30):21982-21986.

Schlatter & Fussenegger, 2003, "Novel CNBP—and La-based translation control systems for mammalian cells." Biotechnol Bioeng. 81(1):1-12.

Schultze et al., 1994, "Three-dimensional solution structure of the thrombin-binding DNA aptamer d(GGTTGGTGTGGTTGG)." J. Mol. Biol. 235:1532-1547.

Shaw & Kamen. 1986, "A conserved AU sequence from the 3' untranslated region of GM-CSF mRNA mediates selective mRNA degradation." Cell 46:659-667.

Shyu et al., 1991, "Two distinct destabilizing elements in the c-fos message trigger deadenylation as a first step in rapid mRNA decay." Genes Dev 5:221-231.

Stebbins-Boaz et al., 1996, "CPEB controls the cytoplasmic polyadenylation of cyclin, Cdk2 and c-mos mRNAs and is necessary for oocyte maturation in *Xenopus*." EMBO J. 15(10):2582-2592.

Stoecklin et al., 1994, "Functional Hierarchy of AUUUA Motifs in Mediating Rapid Interleukin-3 mRNA decay." J Biol. Chem. 269:28591-28597.
Stolle et al., 1988, "Cellular Factor affecting the stability of β-globin mRNA." Gene 62:65-74.
Stoneley, 1998, "C-Myc 5' untranslated region contains an internal ribosome entry segment" Oncogene 16:423-428.
Sullivan et al., 1996, "Mutational analysis of the DST element in tobacco cells and transgenic plants: Identification of residues critical for mRNA instability," RNA 2:308-315.
Tay et al., 2000, "The control of cyclin BI mRNA translation during mouse oocyte maturation." Dev. Biol. 221(1):1-9.
Thiele et al., 1999. "Expression of leukocyte-type 12-lipoxygenase and reticulocyte-type 15-lipoxygenase in rabbits" Adv Exp Med Biol. 447:45-61.
Tholanikunnel & Malborn, 1997, "A 20-nucleotide (A + U)-rich element of beta2-adrenergic receptor (beta2AR) mRNA mediates binding to beta2AR-binding protein and is obligate for agonist-induced destabilization of receptor mRNA." J. Biol. Chem. 272:11471.
Thompson et al., 2000, "Rapid deadenylation and Poly(A)-dependent translational repression mediated by the *Caenorhabditis elegans* tra-2 3' untranslated region in *Xenopus* embryos." Mol. Cell. Biol. 20(6):2129-2137.
Trifillis et al., 1999, "Finding the right RNA: identification of cellular mRNA substrates for RNA-binding proteins." RNA 5:1071-1082.
Trotta et al.. 1997, "The yeast tRNA splicing endonuclease: a tetrameric enzyme with two active site subunits homologous to the archaeal tRNA endonucleases." Cell 89:849-858.
Trotta., 1999, "The Composition, Function and Evolution of the tRNA Splicing Endonuclease." Thesis. California Institute of Technology, pp. 1-147.
Vagner et al., 1995, "Alternative translation of human fibroblast growth factor 2 mRNA occurs by internal entry of ribosomes." Mol. Cell. Biol. 15:35-44.
Vagner et al., 2001, "Irresistible IRES. Attracting the translation machinery to internal ribosome entry sites." EMBO Reports 2:893.
Volarevic et al., 2000, "Proliferation, but not growth blocked by conditional deletion of 40S ribosomal protein S6." Science 288:2045-2047.
Wang et al., 1993, "A DNA aptamer which binds to and inhibits thrombin exhibits a new structural motif for DNA." Biochem. 32(8):1899-1904.
Wang et al., 2003, "Human SP-A 3'-UTR variants mediate differential gene expression in basal levels and in response to dexamethasone", Am. J. Physiol. Lung Cell. Mol. Physiol. 284:L738-L748.
Wells et al., 1998, "Circularization of mRNA by eukaryotic translation initiation factors." Mol. Cell. 2:135-140.
Westmark & Malter, 2001, "Extracellular-regulated kinase controls beta-amyloid precursor protein mRNA decay" Brain Res Mol. Brain. Res 90(2):193-201.
Wilkund et al., 2002. "Inhibition of translation by UAUUUAU and UAUUUUUAU motifs of the AU-rich RNA instability element in the HPV-1 late 3' untranslated region." J. Biol. Chem. 277:40462.
Winstall et al., 1995, "Rapid mRNA degradation mediated by the c-fos 3' AU-rich element and that mediated by the granulocyte-macrophage colony-stimulating factor 3' AU-rich element occur through similar polysome-associated mechanisms" Mol. Cell. Biol. 15:3796-3804.
Worthington et al., 2002, "RNA binding properties of the AU-rich element-binding recombinant Nup475/TISII/tristetraprolin protein." J. Biol. Chem. 277: 48558-48564.
Xu et al., 1997, "Modulation of the fate of cytoplasmic mRNA by AU-rich elements: key sequence features controlling mRNA deadenylation and decay." Mol. Cell. Biol. 17:4611-4621.
Ye et al., 1997, "Ultrabithorax and Antennapedia 5' untranslated regions promote developmentally regulated internal translation initiation" Mol. Cell. Biol. 17:1714-1721.
Zaidi & Malter, 1995,"Nucleolin and heterogeneous nuclear ribonucleoprotein C proteins specifically interact with the 3'-untranslated region of amyloid protein precursor mRNA." J. Biol. Chem. 271( 29):17292-17298.

Zhang et al., 1996. "An enhanced green fluorescent protein allows sensitive detection of gene transfer in mammalian cells." BBRC 227:707-711.
Zhang et al., 1995, "Identification and characterization of a sequence motif involved in nonsense-mediated mRNA decay" Mol. Cell. Biol. 15:2231-2244.
Zhang et al., 1997, "Gene expression profiles in normal and cancer cells." Science 276:1268-1272.
Zhu et al., 2001, "Binding of the La autoantigen to the 5' untranslated region of a chimeric human translation elongation factor IA reporter mRNA inhibits translation in vitro." Biochim. Biophys Acta 1521(1-3):19-29.
Zubiaga et al., 1995, "The nonamer UUAUUUAUU is the key AU-rich sequence motif that mediates mRNA degradation," Mol. Cell. Biol. 15(4):2219-2230.
Written Opinion of the International Searching Authority dated Jul. 14, 2008 in the PCT Application No. PCT/US04/01643 filed Jan. 21, 2004.
International Search Report dated Jul. 14, 2008 in the PCT Application No. PCT/US04/01643 filed Jan. 21, 2004.
International Search Report dated Jul. 13, 2005 in the PCT Application No. PCT/US04/26309 filed Aug. 16, 2004.
International Preliminary Report on Patentability, dated Jan. 23, 2007 in the PCT Application No. PCT/USO4/26309 filed Aug. 16, 2004.
Written Opinion of the International Searching Authority dated Jul. 13, 2005 in the PCT Application No. PCT/USO4/26309 filed Aug. 16, 2004.
International Preliminary Report on Patentability, dated Nov. 19, 2007 in the PCT Application No. PCT/US04/020751 filed Jun. 28, 2004.
Written Opinion of the International Searching Authority dated Jul. 6, 2011 in the PCT Application No. PCT/US04/020751 filed Jun. 28, 2004.
Cao, "Develop New cancer drugs that control VEGF expression: VEGF is an endothelial cell specific mitogen." Grant application.
Cao, "Targeting VEGF 5'-and 3'-UTRs for tumor therapy: generation of stable cell lines for High Throughput screening."
Trotta, "Gene Expression" Revised Background Draft.
Supplemental Partial European Search Report, dated May 30, 2008, issued in EP 04781055.1 (EP 1786933).
Supplemental European Search Report, dated Nov. 19, 2008, issued in EP 04809465.0 (EP1761638.
Preliminary Amendment filed Oct. 23, 2006 in U.S. Appl. No. 10/543,033.
Restriction Requirement mailed May 16, 2008 in U.S. Appl. No. 10/543,033.
Response to Restriction Requirement filed Nov. 17, 2008 in U.S. Appl. No. 10/543,033.
Office Action mailed Feb. 20, 2009 in U.S. Appl. No. 10/543,033.
Restriction Requirement mailed Dec. 28, 2006 in U.S. Appl. No. 10/895,393.
Response to Restriction Requirement filed Apr. 25, 2007 in U.S. Appl. No. 10/895,393.
Response to Notice of Non-Compliant Amendment filed Jul. 9, 2007 in U.S. Appl. No. 10/895,393.
Office Action mailed Oct. 4, 2007 in U.S. Appl. No. 10/895,393.
Amendment tiled Apr. 3, 2008 in U.S. Appl. No. 10/895,393.
Final Office Action mailed Dec. 16, 2008 in U.S. Appl. No. 10/895,393.
Database WPI Week, 2002. "Screening drug improving insulin resistance without exacerbating diabetic retinopathy, by deteching expression of reporter gene fused to promoter region of human vascular endothelial growth factor gene in mammal cell." JP 2001 340080 A.
Yamazaki et al., 2003, "HIF-I dependent VEGF reporter gene assay by a stable transformant of CHO cells." Bio & Pharm Bulletin. 26(4): 417-420.

* cited by examiner

FIG. 1

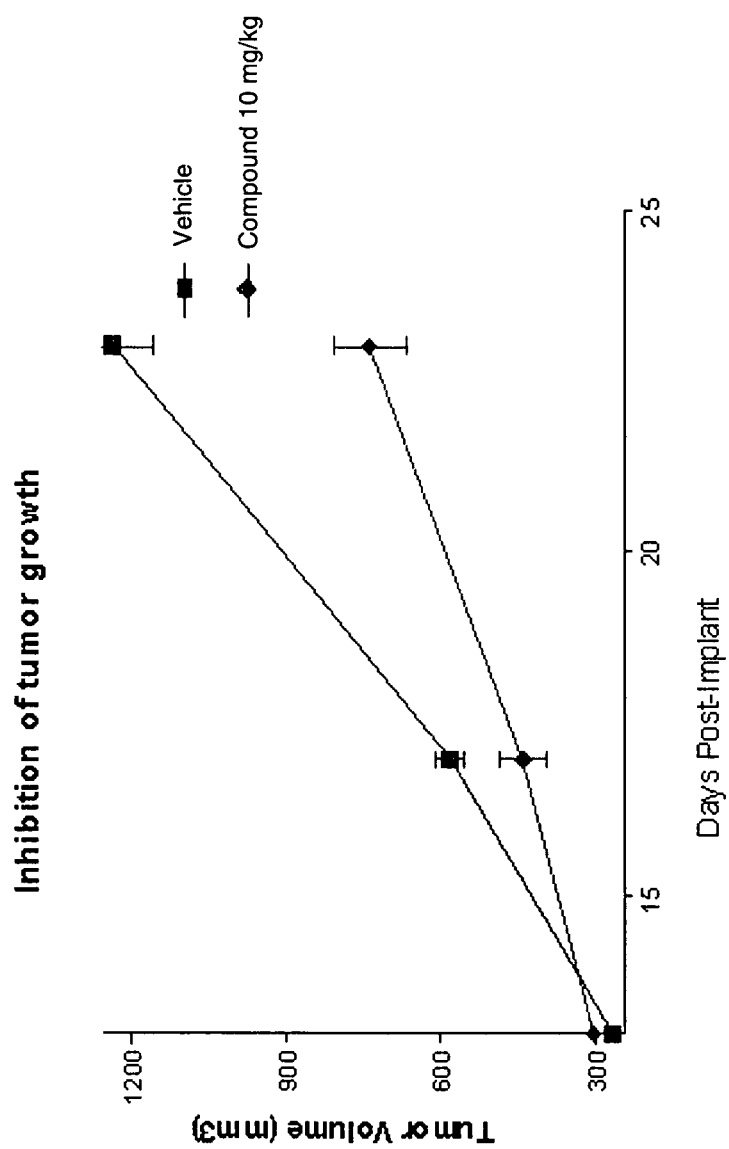

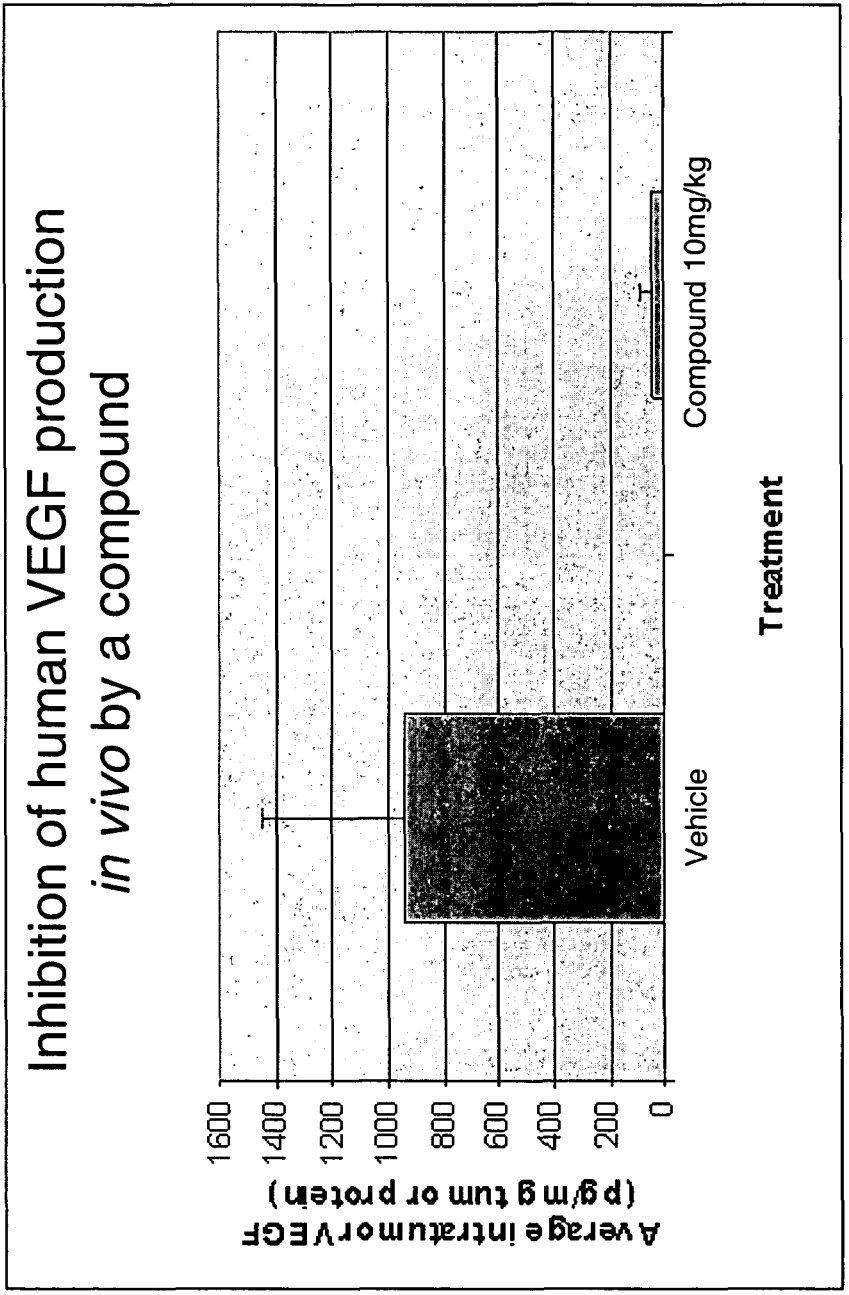

METHODS AND AGENTS FOR SCREENING FOR COMPOUNDS CAPABLE OF MODULATING VEGF EXPRESSION

CROSS-REFERENCE TO RELATED APPLICATIONS

This application is a continuation-in-part of International Application PCT/US04/01643, filed Jan. 21, 2004, entitled Methods for Identifying Compounds that Modulate Untranslated Region-Dependent Gene Expression and Methods of Using Same, under 35 U.S.C. §120. The International Application PCT/US04/01643, claims the benefit of and incorporates by reference U.S. Provisional Application No. 60/441,637, filed on Jan. 21, 2003. The entirety of these applications, including the sequence listing, is hereby incorporated by reference.

INCORPORATION OF SEQUENCE LISTING

A paper copy of the Sequence Listing and a computer readable form of the sequence listing on diskette, containing the file named "19025.014.seqlist.txt", which is 16,435 bytes in size (measured in MS-DOS), and which was recorded on May 24, 2004, are herein incorporated by reference.

BACKGROUND OF THE INVENTION

Aberrant angiogenesis plays a role in the pathogenesis of numerous diseases, including malignant, ischemic, inflammatory and immune disorders (reviewed in Matter, *Drug Discovery Today*, 6:1005-1024 (2001); Yancopoulos et al, *Nature*, 407:242-248 (2000); Carmeliet, *Nat. Med.*, 9(6):653-660 (2003); Ferrara, *Semin. Oncol.*, 29(6 Suppl 16):10-14 (2002)). Vascular Endothelial Growth Factor (VEGF), an angiogenesis regulator, plays a central role in angiogenesis. In particular, VEGF is an important factor in the pathogenesis of cancers, diabetic retinopathy (DR), and exudative macular degeneration (reviewed in Tandle et al., *Clin. Adv. in Hemat. and Oncol.*, 1(1):41-48 (2003); Ferrara et al., *Nat. Med.*, 5(12):1359-1364 (1999); Matter, supra; Carmeliet supra; Kerbel et al., *Nat. Rev. Cancer*, 2(10):727-739 (2002); Witmer et al., *Prog. Retin. Eye Res.*, 22(1):1-29 (2003); Clark et al., *Nat. Rev. Drug Discovery*, 2:448-459 (2003); Ferrara (2002), supra; Thomas, *J. Biol. Chem.*, 271:603-606 (1996); Gerber et al., *Development*, 126:1149-1159 (1999); which are hereby incorporated by reference), the last two of which are leading causes of blindness in the United States.

The expression of VEGF is regulated by a number of factors and agents including cytokines, growth factors, steroid hormones and chemicals, and mutations that modulate the activity of oncogenes such as ras or the tumor suppressor gene VHL (Maxwell et al., *Nature*, 399:271-275 (1999); Rak et al., *Cancer Res.*, 60:490-498 (2000)). In part, VEGF expression is regulated after transcription by sequences in both the 5'- and 3'-untranslated regions (UTRs) of its mRNA (Ikeda et al., *J. Biol. Chem.*, 270:19761-19766 (1995); Stein et al., *Mol. Cell. Biol.*, 18:3112-3119 (1998); Levy et al. *J. Biol. Chem.*, 271:2746-2753 (1996); Huez et al., *Mol. Cell. Biol.*, 18:6178-6190 (1998); Akiri et al., *Oncogene*, 17:227-236 (1998)). The VEGF 5' UTR is unusually long and GC rich, and it contains an internal ribosomal entry site (IRES) that is reported to mediate a unique, cap-independent mode of translation initiation. The VEGF 3' UTR harbors multiple AU-rich stability determinants that have been shown to be associated with VEGF mRNA turnover rates.

Initiation of translation of the VEGF mRNA is reported to be unique under hypoxic conditions in that it is mediated via an internal ribosome entry site (IRES) within the VEGF 5' UTR (Stein et al., supra; Levy et al., supra; Huez et al., supra; Akiri et al., supra). Under hypoxic conditions, cap-dependent translation is dramatically impaired and the translation of the VEGF mRNA occurs through its cap-independent IRES. Initiation of translation of most eukaryotic mRNA is cap-dependent. IRES-mediated translation initiation becomes predominant when components of the translation initiation complex become rate-limiting, e.g., during hypoxia (Mitchell et al., *Mol. Cell.*, 1(3):757-771 (2003)).

Several investigators have used in vitro and bicistronic strategies, often in conjunction with deletion mutants, to study regulation of VEGF. Prats and colleagues reported the occurrence of cap-independent translation of human VEGF by virtue of an IRES. From these studies, they postulated the presence of two IRESs, a first IRES (IRES A) located within 300 nucleotides of the initiation codon and a second IRES (IRES B) located in the upstream half of the 5'-UTR. Huez et al., supra. In Stein et al., supra., deletion mutants in dicistronic and monocistronic constructs were used to identify sequences of the VEGF 5' UTR required for maximal IRES activity. Keshet and colleagues reported an increase in IRES activity from a 163-nucleotide sequence derived from a VEGF 5' UTR, which is possibly an artifact from RT-PCR amplification, relative to the entire full-length VEGF 5' UTR. Stein et al., supra. Goodall and colleagues reported a deletion analysis of IRES residues toward the 3' end of the mouse VEGF 5' UTR, and speculated that, for optimal IRES activity, the upstream half of the VEGF 5' UTR is necessary. Miller et al., supra.

The present invention provides, for the first time, a negative regulator of post-transcriptional regulation (NeRP) located in the 5' UTR of VEGF. Removal of a NeRP from the VEGF 5' UTR results in increased translation of an operably linked gene dependent on the presence of a PTCRE of the present invention.

SUMMARY OF THE INVENTION

The present invention includes a nucleic acid construct comprising a nucleic acid sequence encoding a reporter polypeptide, where the nucleic acid sequence encoding a reporter polypeptide is operably linked to a NeRP, the NeRP is operably linked to a PTCRE, the PTCRE is not SEQ ID NO: 3, and expression of the reporter polypeptide is capable of being modulated relative to in an absence of the NeRP.

The present invention also includes a nucleic acid molecule comprising a nucleic acid sequence encoding a reporter polypeptide and a VEGF 5' UTR nucleic acid sequence in an absence of SEQ ID NO: 4.

The present invention also includes a nucleic acid molecule comprising a nucleic acid sequence encoding a reporter polypeptide operably linked to a VEGF 5' UTR in an absence of SEQ ID NO: 4.

The present invention also includes a nucleic acid molecule comprising a nucleic acid sequence encoding a reporter polypeptide, where the nucleic acid sequence encoding a reporter polypeptide is operably linked downstream of a UTR containing a NeRP, and the UTR is not operably upstream of SEQ ID NO: 3.

The present invention also includes a heterogeneous population of nucleic acid molecules, where the heterogeneous population comprises a reporter nucleic acid sequence, and the nucleic acid sequence encoding a reporter polypeptide is operably linked to a VEGF 5' UTR in an absence of NeRP1 (SEQ ID NO: 4).

The present invention also includes a substantially purified nucleic acid molecule comprising between 95% and 99% sequence identity with a nucleic acid molecule of SEQ ID NO: 3, a fragment thereof, or a complement of either.

The present invention also includes a substantially purified nucleic acid molecule consisting of SEQ ID NO: 3, a fragment thereof, or a complement of either.

The present invention also includes a substantially purified nucleic acid molecule consisting of a first nucleic acid sequence linked to a heterologous nucleic acid sequence encoding a polypeptide, where the first nucleic acid sequence is selected from the group consisting of SEQ ID NO: 3, a fragment thereof, and a complement of either.

The present invention also includes a substantially purified nucleic acid molecule comprising between 95% and 99% sequence identity with a nucleic acid molecule of SEQ ID NO: 4, a fragment thereof, or a complement of either.

The present invention also includes a substantially purified nucleic acid molecule of a nucleic acid sequence selected from a group consisting of SEQ ID NO: 4, a fragment thereof, and a complement of either.

The present invention also includes a substantially purified nucleic acid molecule consisting of a first nucleic acid sequence linked to a heterologous nucleic acid sequence encoding a polypeptide, where the first nucleic acid sequence is selected from the group consisting of SEQ ID NO: 4, a fragment thereof, and a complement of either.

The present invention also includes a method of making a nucleic acid construct to screen for a compound comprising: a) providing a main ORF downstream of a promoter in the nucleic acid construct; b) operably linking a VEGF 5' UTR in an absence of SEQ ID NO: 4 upstream of the main ORF; and c) operably linking a VEGF 3' UTR downstream of the main ORF.

The present invention also includes a method of screening in vivo for a compound that modulates UTR-dependent expression comprising: a) providing a cell having a nucleic acid molecule comprising a promoter upstream from a VEGF 5' UTR in an absence of SEQ ID NO: 4, where the VEGF 5' UTR in an absence of SEQ ID NO: 4 is upstream from a nucleic acid sequence encoding a reporter polypeptide, and the nucleic acid sequence encoding a reporter polypeptide is upstream from a VEGF 3' UTR; b) contacting the cell with a compound; c) producing a nucleic acid molecule that contains a nucleic acid sequence encoding a reporter polypeptide and does not contain SEQ ID NO: 4; and d) detecting the reporter polypeptide.

The present invention also includes a method of screening in vitro for a compound that modulates UTR-affected expression comprising: a) providing an in vitro translation system; b) contacting the in vitro translation system with a compound and a nucleic acid molecule comprising a VEGF 5' UTR in an absence of SEQ ID NO: 4, where the VEGF 5' UTR in an absence of SEQ ID NO: 4 is upstream from a nucleic acid sequence encoding a reporter polypeptide and the nucleic acid sequence encoding a reporter polypeptide is upstream from a VEGF 3' UTR; and c) detecting the reporter polypeptide in vitro.

The present invention also includes a method of expressing a nucleic acid molecule in a cell comprising: a) providing a nucleic acid molecule to a cell, where the nucleic acid molecule comprises a nucleic acid sequence encoding a reporter polypeptide flanked by VEGF UTRs in an absence of SEQ ID NO: 4; and b) detecting the reporter polypeptide.

The present invention also includes a method of screening for a compound that modulates protein expression through a main ORF-independent, UTR-affected mechanism comprising: a) growing a stable cell line having a reporter gene operably linked to a VEGF 5' UTR in an absence of SEQ ID NO: 4; b) comparing the stable cell line in a presence of a compound relative to the stable cell line in an absence of the compound; and c) selecting for the compound that modulates protein expression through a main ORF-independent, UTR-affected mechanism.

The present invention also includes a method of screening for a compound that modulates protein expression through a main ORF-independent, UTR-affected mechanism comprising: a) growing a stable cell line having a main ORF operably linked to a VEGF 5' UTR in an absence of SEQ ID NO: 4; b) comparing the stable cell line in the presence of a compound relative to the stable cell line in the absence of the compound; and c) selecting for the compound that modulates protein expression through a main ORF-independent, UTR-affected mechanism.

The present invention also includes a method of screening for a compound that modulates protein expression through a VEGF-independent, UTR-affected mechanism comprising: a) substituting in vivo a VEGF gene with a reporter gene, where a UTR consisting of SEQ ID NO: 3 is operably linked to the reporter gene, and the substitution occurs in a differentiated cell; b) growing the differentiated cell; and c) selecting for the compound that modulates protein expression of the reporter gene through a main ORF-independent, UTR-affected mechanism.

The present invention also includes a method of screening for a compound that modulates protein expression through a main ORF-independent, UTR-affected mechanism comprising: a) substituting in vivo a main ORF with a reporter gene, where a 5' UTR is operably linked to the reporter gene and consists of SEQ ID NO: 3, and the substitution occurs in a differentiated cell; b) growing the differentiated cell; and c) selecting for the compound that modulates protein expression of the reporter gene through a main ORF-independent, UTR-affected mechanism.

The present invention also includes a method of screening for a compound that modulates protein expression through a UTR-affected mechanism comprising: a) providing a stable cell line having a reporter gene operably linked to a VEGF 5' UTR in an absence of SEQ ID NO: 4, where the stable cell line mimics post-transcriptional regulation of a VEGF gene found in vivo in presence of the compound; b) maintaining the stable cell line; and c) selecting for the compound that modulates protein expression of the reporter gene through a UTR-affected mechanism.

The present invention also includes a method of screening for a compound that modulates protein expression through a UTR-affected mechanism comprising: a) providing a stable cell line having a main ORF encoding a reporter polypeptide operably linked to a VEGF 5' UTR in an absence of SEQ ID NO: 4, where the stable cell line mimics post-transcriptional regulation of a VEGF gene found in vivo in a presence of a compound; b) maintaining the stable cell line; and c) selecting for the compound that modulates protein expression of the main ORF through a UTR-affected mechanism.

The present invention also includes a method of screening for a compound that modulates protein expression through a UTR-affected mechanism mediating the effect of a NeRP comprising: a) growing a stable cell line having a reporter gene operably linked to a 5' VEGF UTR in an absence of a NeRP1 (SEQ ID NO: 4); b) comparing the stable cell line in a presence of a compound relative to in an absence of the compound, where the compound does not modulate UTR-dependent expression if the 5' VEGF UTR in an absence of a NeRP1 (SEQ ID NO: 4) is operably linked to a reporter gene; and c) selecting for the compound that modulates protein expression of the reporter gene through a UTR-affected mechanism mediating the effect of a NeRP.

The present invention also includes a method of screening for a compound that modulates protein expression through a UTR-affected mechanism mediating the effect of a NeRP comprising: a) growing a stable cell line having a main ORF encoding a reporter polypeptide operably linked to a 5' VEGF UTR in an absence of a NeRP1 (SEQ ID NO: 4); b) comparing the stable cell line in the presence of a compound relative to that in the absence of the compound, where the compound does not modulate UTR-dependent expression if the 5' VEGF UTR in an absence of a NeRP1 (SEQ ID NO: 4) is operably linked to a main ORF; and c) selecting for the compound that modulates protein expression of the main ORF through a UTR-affected mechanism mediating the effect of a NeRP.

The present invention also includes a method of screening for a compound that modulates protein expression through a UTR-affected mechanism mediating the effect of a NeRP comprising: a) growing a stable cell line having a reporter gene operably linked to a UTR having a NeRP1 (SEQ ID NO: 4); b) comparing the stable cell line in a presence of a compound relative to in an absence of the compound, where the compound modulates UTR-dependent expression if a NeRP1 (SEQ ID NO: 4) is operably linked to a reporter gene; and c) selecting for the compound that modulates protein expression of the reporter gene through a UTR-affected mechanism mediating the effect of a NeRP.

The present invention also includes a method of screening for a compound that modulates protein expression through a UTR-affected mechanism mediating the effect of a NeRP comprising: a) growing a stable cell line having a main ORF encoding a reporter polypeptide operably linked to a UTR having a NeRP1 (SEQ ID NO: 4); b) comparing the stable cell line in a presence of a compound relative to in an absence of the compound, where the compound modulates UTR-dependent expression if a NeRP1 (SEQ ID NO: 4) is operably linked to a main ORF encoding a reporter polypeptide; and c) selecting for the compound that modulates protein expression of the main ORF encoding a reporter polypeptide through a UTR-affected mechanism mediating the effect of the NeRP.

BRIEF DESCRIPTION OF THE DRAWINGS

Figure 1:
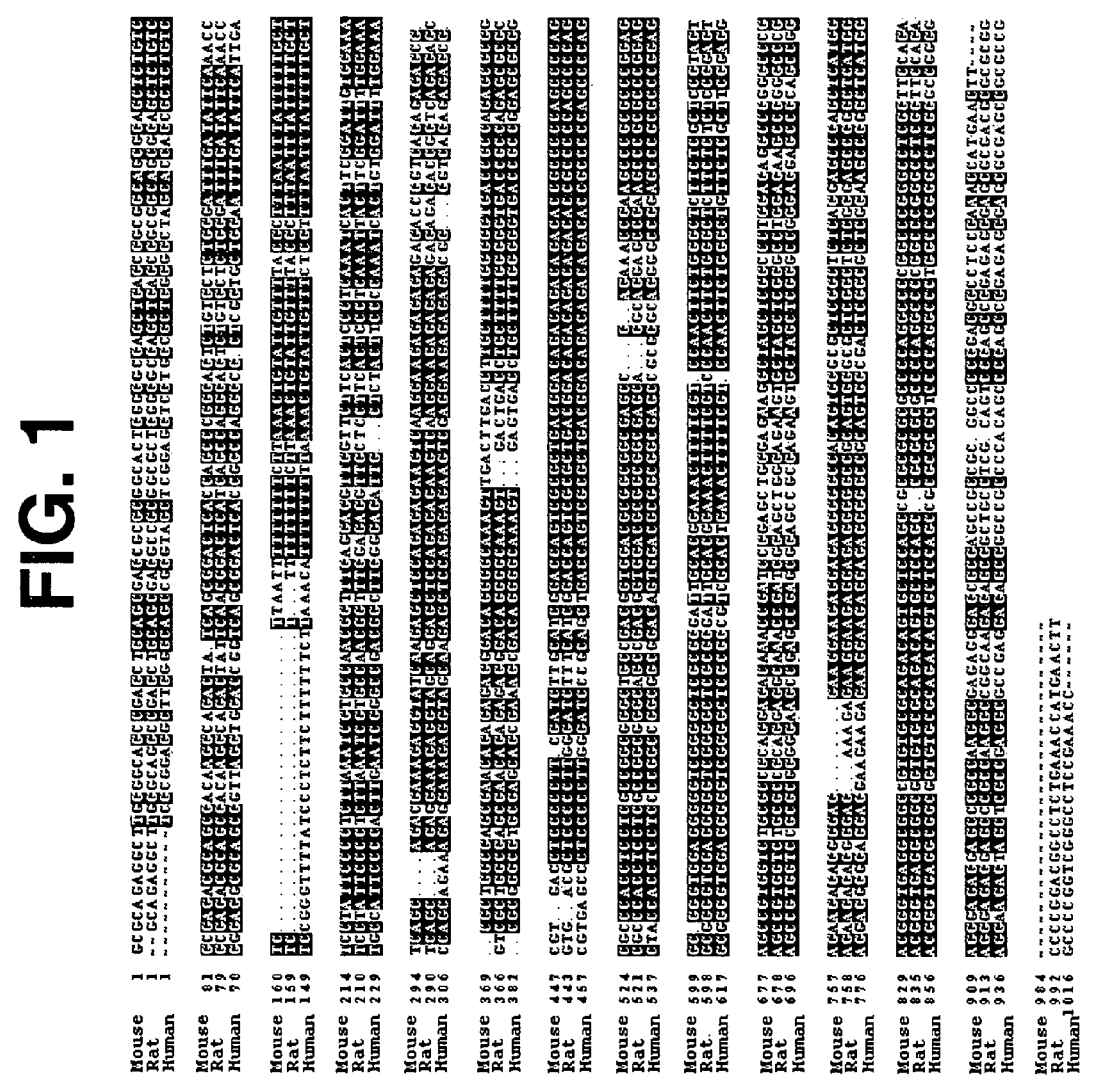

FIG. 1 sets forth a sequence alignment of VEGF 5' UTR for mouse, rat, and human.

FIG. 4A sets forth an example of effective inhibition of VEGF production in tumor tissue.

FIG. 4B sets forth the inhibition of human VEGF production in vivo by a compound.

DESCRIPTION OF THE NUCLEIC ACID SEQUENCES

Figure 2:
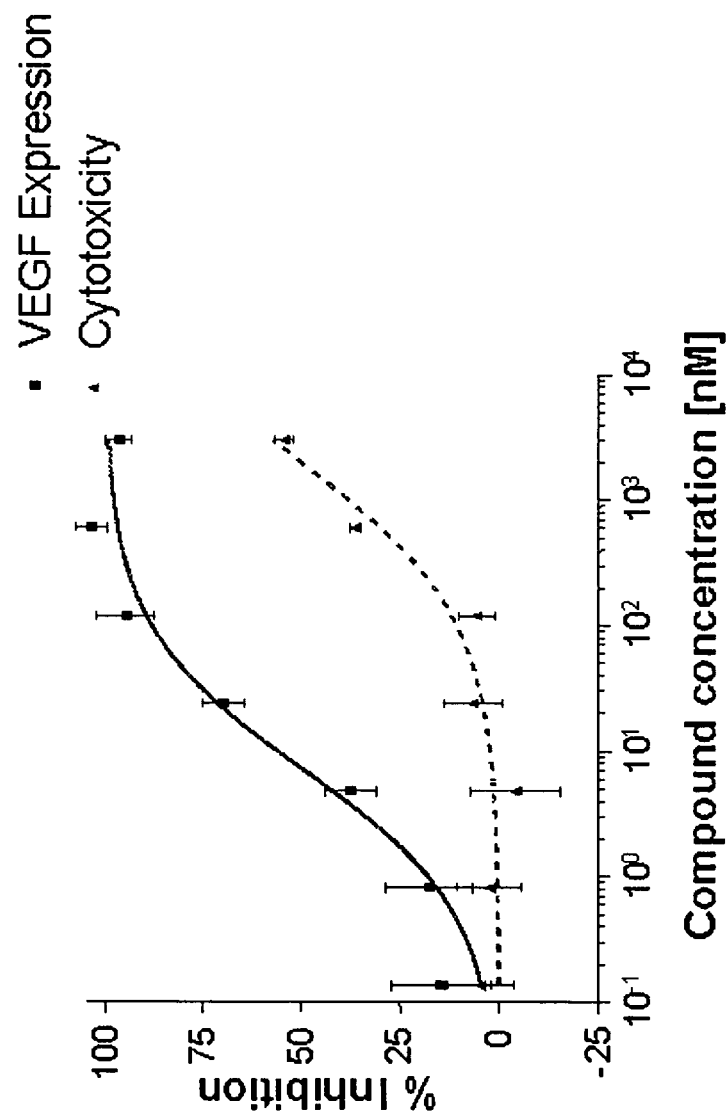
FIG. 2 sets forth an example of a compound that inhibits VEGF expression over a concentration range.

SEQ ID NO: 1 sets forth a full-length VEGF 5' UTR.
SEQ ID NO: 2 sets forth an open reading frame encoding VEGF.
SEQ ID NO: 3 sets forth a PTCRE1, a 702 nucleotide region of a VEGF 5' UTR.
SEQ ID NO: 4 sets forth a NeRP1, a 336 nucleotide region of a VEGF 5' UTR.
SEQ ID NO: 5 sets forth a PTCRE2, a 485 nucleotide region of a VEGF 5' UTR.
SEQ ID NO: 6 sets forth a PTCRE3, a 556 nucleotide region of a VEGF 5' UTR.
SEQ ID NO: 7 sets forth a PTCRE4, a 294 nucleotide region of a VEGF 5' UTR.
SEQ ID NO: 8 sets forth a PTCRE5, a 194 nucleotide region of a VEGF 5' UTR.
SEQ ID NO: 9 sets forth a NeRP2, a 476 nucleotide region of a VEGF 5' UTR.
SEQ ID NO: 10 sets forth a NeRP3, a 554 nucleotide region of a VEGF 5' UTR.
SEQ ID NO: 11 sets forth a NeRP4, a 51 nucleotide region of a VEGF 5' UTR.
SEQ ID NO: 12 sets forth a NeRP5, a 91 nucleotide region of a VEGF 5' UTR.
SEQ ID NO: 13 sets forth a NeRP6, a 335 nucleotide region of a VEGF 5' UTR.
SEQ ID NO: 14 sets forth a NeRP7, a 332 nucleotide region of a VEGF 5' UTR.
SEQ ID NO: 15 sets forth a NeRP8, a 331 nucleotide region of a VEGF 5' UTR.
SEQ ID NO: 16 sets forth a NeRP9, a 330 nucleotide region of a VEGF 5' UTR.
SEQ ID NO: 17 sets forth a NeRP10, a 329 nucleotide region of a VEGF 5' UTR.
SEQ ID NO: 18 sets forth a NeRP11, a 328 nucleotide region of a VEGF 5' UTR.
SEQ ID NO: 19 sets forth a NeRP12, a 327 nucleotide region of a VEGF 5' UTR.
SEQ ID NO: 20 sets forth a NeRP13, a 326 nucleotide region of a VEGF 5' UTR.
SEQ ID NO: 21 sets forth a NeRP14, a 316 nucleotide region of a VEGF 5' UTR.
SEQ ID NO: 22 sets forth a NeRP15, a 306 nucleotide region of a VEGF 5' UTR.
SEQ ID NO: 23 sets forth a NeRP16, a 296 nucleotide region of a VEGF 5' UTR.
SEQ ID NO: 24 sets forth a NeRP17, a 286 nucleotide region of a VEGF 5' UTR.

SEQ ID NO: 25 sets forth a NeRP18, a 276 nucleotide region of a VEGF 5' UTR.

SEQ ID NO: 26 sets forth a NeRP19, a 266 nucleotide region of a VEGF 5' UTR.

Definitions

As used herein, the term "construct" refers to an artificially manipulated nucleic acid molecule.

As used herein, the term "heterologous" refers to ingredients or constituents of dissimilar or diverse origin.

As used herein, the term "mammalian cancer cell" or "mammalian tumor cell" refers to a cell derived from a mammal that proliferates inappropriately.

As used herein, the term "main ORF-independent mechanism" refers to a cellular pathway or process, wherein at least one step relates to gene expression and is not dependent on the nucleic acid sequence of the main open reading frame.

As used herein, the term "reporter gene" refers to any gene whose expression can be measured.

As used herein, the term "RNA induced gene silencing, or RNA interference (RNAi)" refers to the mechanism of double-stranded RNA (dsRNA) introduced into a system to reduce protein expression of specific genetic sequence.

As used herein, the term "specifically bind" means that a compound binds to another compound in a manner different from a similar type of compounds, e.g. in terms of affinity, avidity, and the like. In a non-limiting example, more binding occurs in the presence of a competing reagent, such as casein. In another non-limiting example, antibodies that specifically bind a target protein should provide a detection signal at least 2-, 5-, 10-, or 20-fold higher relative to a detection signal provided with other molecules when used in Western blots or other immunochemical assays. In an alternative non-limiting example, a nucleic acid can specifically bind its complementary nucleic acid molecule. In another non-limiting example, a transcription factor can specifically bind a particular nucleic acid sequence.

As used herein, the term "secondary structure" means the alpha-helical, beta-sheet, random coil, beta turn structures and helical nucleic acid structures that occur in proteins, polypeptides, nucleic acids, compounds comprising modified nucleic acids, compounds comprising modified amino acids, and other types of compounds as a result of, at least, the compound's composition.

As used herein, the term "non-peptide therapeutic agent" and analogous terms include, but are not limited to organic or inorganic compounds (i.e., including heteroorganic and organometallic compounds but excluding proteins, polypeptides and nucleic acids).

As used herein, the term "UTR" refers to the untranslated region of a mRNA.

As used herein, the term "untranslated region-dependent expression" or "UTR-dependent expression" refers to the regulation of gene expression through UTRs at the level of mRNA expression, i.e., after transcription of the gene has begun until the protein or the RNA product(s) encoded by the gene has degraded or excreted.

As used herein, the term "vector" refers to a nucleic acid molecule used to introduce a nucleic acid sequence in a cell or organism. The entirety of the International Application PCT/US04/01643, filed Jan. 21, 2004, including the sequence listing, is hereby incorporated by reference.

DETAILED DESCRIPTION OF THE INVENTION

The present invention includes and utilizes the fact that an untranslated region (UTR) is capable of modulating expression of a gene and that such modulation of expression is capable of being altered or modulated by the addition of compounds. In a preferred embodiment, a UTR is a region of a RNA that is not translated into protein. In a more preferred embodiment, a UTR is a flanking region of the RNA transcript that is not translated into the targeted protein, and can include a 5' UTR that has a short, putative open reading frame. In a most preferred embodiment, the UTR is a 5' UTR, i.e., upstream of the coding region, or a 3' UTR, i.e., downstream of the coding region.

Moreover, the present invention includes and provides agents and methods useful in screening for a compound capable of modulating gene expression and also hybrid molecules.

Nucleic Acid Agents and Constructs

One skilled in the art may refer to general reference texts for detailed descriptions of known techniques discussed herein or equivalent techniques. These texts include Ausubel et al., *Current Protocols in Molecular Biology*, John Wiley and Sons, Inc. (1995); Sambrook et al., *Molecular Cloning, A Laboratory Manual* (2d ed.), Cold Spring Harbor Press, Cold Spring Harbor, N.Y. (1989); Birren et al., *Genome Analysis: A Laboratory Manual*, volumes 1 through 4, Cold Spring Harbor Press, Cold Spring Harbor, N.Y. (1997-1999). These texts can, of course, also be referred to in making or using an aspect of the invention.

UTRs

The present invention includes nucleic acid molecules with UTRs that comprise or consist of a post-transcriptional regulatory element (PTCRE) including SEQ ID NO: 3, a negative regulator of a PTCRE (NeRP) including SEQ ID NO: 4, and fragments and complements of all.

A PTCRE of the present invention can differ from any of the residues in SEQ ID NO: 3 in that the nucleic acid sequence has been deleted, substituted, or added in a manner that does not alter the function. In another aspect of the present invention, a PTCRE of the present invention consists or comprises SEQ ID NO: 5, and fragments and complements of all. In another aspect of the present invention, a PTCRE of the present invention consists or comprises SEQ ID NOs: 6-8, and fragments and complements of all.

A PTCRE of the present invention can differ from any of the residues in an untranslated region selected from the group consisting of a nucleic acid sequence consisting or comprising SEQ ID NO: 3 and SEQ ID NOs: 5-8 in that the nucleic acid sequence has been deleted, substituted, or added in a manner that does not alter the function.

A NeRP of the present invention can differ from any of the residues in SEQ ID NO: 4 in that the nucleic acid sequence has been deleted, substituted, or added in a manner that does not alter the function.

In another aspect of the present invention, a NeRP of the present invention consists or comprises SEQ ID NO: 9, and fragments and complements of all. In another aspect of the present invention, a NeRP of the present invention consists or comprises SEQ ID NOs: 10-12, and fragments and complements of all.

A NeRP of the present invention can differ from any of the residues in a UTR selected from the group consisting of a nucleic acid sequence consisting or comprising SEQ ID NO: 4 and SEQ ID NOs: 9-12 in that the nucleic acid sequence has been deleted, substituted, or added in a manner that does not alter the function. In one aspect, a NeRP is not a full-length sequence of a target UTR. In a preferred aspect, a NeRP is not a full-length VEGF 5' UTR.

In one embodiment, a NeRP can be a nucleic acid sequence with a single base deletion at any location of SEQ ID NO: 4. Therefore, a NeRP of the invention may be 335 bases. In another embodiment, a NeRP includes a nucleic acid sequence with two or more bases deleted from any location of SEQ ID NO: 4. In another embodiment, a NeRP includes 3, 4, 5, 6, 7, 8, 9 or 10 residue deletions at any location of SEQ ID NO: 4. In another embodiment, a NeRP includes the remaining nucleic acid sequence resulting from the deletion of 20, 30, 40, 50, 60, or 70 residues from any location of SEQ ID NO: 4. In light of the specification, a NeRP of the present invention may be produced by contiguous, noncontiguous, or a combination of contiguous deletions and noncontiguous deletions of SEQ ID NO: 4 in a manner that does not alter the function of the NeRP.

In a preferred embodiment, when a nucleic acid molecule, which includes a NeRP and a PTCRE, has been deleted, substituted, or added to in a manner that removes the negative regulation of a PTCRE, the secondary structure of the remaining nucleic acid molecule is altered in a manner comparable to the alteration in the secondary structure of a full-length VEGF 5' UTR when SEQ ID NO: 4 is deleted. In a more preferred embodiment, a NeRP of the present invention has a secondary structure comparable to the secondary structure of SEQ ID NO: 4.

In an embodiment of the present invention, the presence of a NeRP can be detected by the deletion, insertion or alteration of one or more pseudoknots from a larger nucleic acid molecule. In another embodiment, the deletion, insertion or alteration of a stem-loop structure from a larger nucleic acid molecule of the present invention results in a NeRP of the present invention. Programs such as mfold, (see the world wide web at bioweb.pasteur.fr/seqanal/interfaces/mfold-simple.html) genebee (see the world wide web at genebee.msu.su/) may be used to ascertain the secondary structure of SEQ ID NO: 4 and other nucleic acid molecules of the present invention. Other programs or methods well known to those of skill in the art can also be employed.

The present invention also includes a NeRP that has a tertiary structure comparable to the tertiary structure formed by SEQ ID NO: 4. Tertiary structure can be determined by, for example, crystallography and phylogenetic covariation (as reviewed in Martin I, et al., *Biochim Biophys Acta*. 2003 Jul. 11; 1614(1):97-103; Heinemann U., et al., *Biol Chem*. 1996 July-August; 377(7-8):447-54).

The present invention provides nucleic acid molecules that hybridize to the above-described nucleic acid molecules. In a preferred aspect, the nucleic acid molecule hybridizes to a nucleic acid molecule selected from the group consisting of a nucleic acid sequence consisting or comprising SEQ ID NOs: 3-12, and complements thereof. Nucleic acid hybridization is a technique well known to those of skill in the art of DNA manipulation. The hybridization properties of a nucleic acid molecule are an indication of their similarity or identity. The nucleic acid molecules preferably hybridize, under moderate or high stringency conditions, with a nucleic acid sequence selected from SEQ ID NO: 5 and complements thereof. Fragments of these sequences are also contemplated.

In another aspect, the nucleic acid molecules preferably hybridize, under moderate or high stringency conditions, with a nucleic acid sequence selected from the group consisting of SEQ ID NO: 5 and its complement.

The hybridization conditions typically involve nucleic acid hybridization in about 0.1× to about 10×SSC (diluted from a 20×SSC stock solution containing 3 M sodium chloride and 0.3M sodium citrate, pH 7.0 in distilled water), about 2.5× to about 5×Denhardt's solution (diluted from a 50× stock solution containing 1% (w/v) bovine serum albumin, 1% (w/v) Ficoll® (Amersham Biosciences Inc., Piscataway, N.J.), and 1% (w/v) polyvinylpyrrolidone in distilled water), about 10 mg/ml to about 100 mg/ml salmon sperm DNA, and about 0.02% (w/v) to about 0.1% (w/v) SDS, with an incubation at about 20° C. to about 70° C. for several hours to overnight.

In a preferred aspect, the moderate stringency hybridization conditions are provided by 6×SSC, 5×Denhardt's solution, 100 mg/ml salmon sperm DNA, and 0.1% (w/v) SDS, with an incubation at 55° C. for several hours. The moderate stringency wash conditions are about 0.02% (w/v) SDS, with an incubation at about 55° C. overnight. In a more preferred aspect, the high stringency hybridization conditions are about 2×SSC, about 3×Denhardt's solution, and about 10 mg/ml salmon sperm DNA. The high stringency wash conditions are about 0.05% (w/v) SDS, with an incubation at about 65° C. overnight.

In an embodiment, the nucleic acid molecule comprises a nucleic acid sequence that is greater than 85% identical, and more preferably greater than 86, 87, 88, 89, 90, 91, 92, 93, 94, 95, 96, 97, 98, or 99% identical to a nucleic acid sequence selected from the group consisting of SEQ ID NOs: 3-12, complements thereof, and fragments of any of these sequences.

The percent identity is preferably determined using the "Best Fit" or "Gap" program of the Sequence Analysis Software Package™ (Version 10; Genetics Computer Group, Inc., University of Wisconsin Biotechnology Center, Madison, Wis.). "Gap" utilizes the algorithm of Needleman and Wunsch to find the alignment of two sequences that maximizes the number of matches and minimizes the number of gaps. "BestFit" performs an optimal alignment of the best segment of similarity between two sequences and inserts gaps to maximize the number of matches using the local homology algorithm of Smith and Waterman. The percent identity calculations may also be performed using the Megalign program of the LASERGENE bioinformatics computing suite (default parameters, DNASTAR Inc., Madison, Wis.). The percent identity is most preferably determined using the "Best Fit" program using default parameters.

Fragment nucleic acid molecules can contain significant portions of, or indeed most of, SEQ ID NO: 3. In an embodiment, the fragments are between about 160 and 250 consecutive residues, about 260 and about 350 consecutive residues, about 360 and about 400 consecutive residues, or about 460 and 500 consecutive residues long of a nucleic molecule of the present invention. In another embodiment, the fragment comprises at least 170, 300, 500, or 600 consecutive residues of SEQ ID NO: 3. In a particularly preferred embodiment, a fragment nucleic acid molecule is capable of selectively hybridizing to SEQ ID NO: 3.

In one embodiment, a PTCRE comprises or consists of SEQ ID NO: 3. In another embodiment, a PTCRE comprises or consists of a fragment of SEQ ID NO: 3. In a preferred embodiment, a PTCRE can share identity with between particular mammals, including, but not limited to human, mouse, and rat. In another preferred embodiment, a PTCRE is unique to a human VEGF 5' UTR PTCRE, a non-limiting example of which is SEQ ID NO: 3.

Fragment nucleic acid molecules can contain significant portions of SEQ ID NO: 4. In another embodiment of the present invention, nucleic acid molecules can comprise or consist of significant portions of SEQ ID NO: 4. In an embodiment, the fragments are between about 40 and about 90 consecutive residues, about 100 and about 150 consecutive residues, about 160 and about 250 consecutive residues, or about 260 and 325 consecutive residues long of a nucleic molecule of the present invention. In another embodiment, the fragment comprises at least 90, 150, 250, or 325 consecutive residues of SEQ ID NO: 4. In a preferred embodiment, a fragment nucleic acid molecule is capable of selectively hybridizing to SEQ ID NO: 4.

In one embodiment, a NeRP comprises or consists of SEQ ID NO: 4. In another embodiment, a NeRP comprises or consists of a fragment of SEQ ID NO: 4. In a preferred embodiment, a NeRP can share identity with between particular mammals, including, but not limited to human, mouse, and rat. In another preferred embodiment, a NeRP is unique to a human VEGF 5' UTR NeRP, a non-limiting example of which is SEQ ID NO: 4.

Any of a variety of methods may be used to obtain one or more of the above-described nucleic acid molecules of the present invention. Automated nucleic acid synthesizers may be employed for this purpose. In lieu of such synthesis, the disclosed nucleic acid molecules may be used to define a pair of primers that can be used with the polymerase chain reaction (PCR) to amplify and obtain any desired nucleic acid molecule or fragment.

Short nucleic acid sequences having the ability to specifically hybridize to complementary nucleic acid sequences may be produced and utilized in the present invention, e.g., as probes to identify the presence of a complementary nucleic acid sequence in a given sample. Alternatively, the short nucleic acid sequences may be used as oligonucleotide primers to amplify or mutate a complementary nucleic acid sequence using PCR technology. These primers may also facilitate the amplification of related complementary nucleic acid sequences (e.g., related sequences from other species).

Use of these probes or primers may greatly facilitate the identification of transgenic cells or organisms that contain the presently disclosed structural nucleic acid sequences. Such probes or primers may also, for example, be used to screen cDNA, mRNA, or genomic libraries for additional nucleic acid sequences related to or sharing homology with the presently disclosed promoters and structural nucleic acid sequences. The probes may also be PCR probes, which are nucleic acid molecules capable of initiating a polymerase activity while in a double-stranded structure with another nucleic acid.

A primer or probe is generally complementary to a portion of a nucleic acid sequence that is to be identified, amplified, or mutated and of sufficient length to form a stable and sequence-specific duplex molecule with its complement. The primer or probe preferably is about 10 to about 200 residues long, more preferably is about 10 to about 100 residues long, even more preferably is about 10 to about 50 residues long, and most preferably is about 14 to about 30 residues long.

The primer or probe may, for example without limitation, be prepared by direct chemical synthesis, by PCR (U.S. Pat. Nos. 4,683,195 and 4,683,202), or by excising the nucleic acid specific fragment from a larger nucleic acid molecule. Various methods for determining the sequence of PCR probes and PCR techniques exist in the art. Computer-generated searches using programs such as Primer3 (www-genome.wi.mit. edu/cgi-bin/primer/primer3.cgi), STSPipeline (www-genome.wi.mit.edu/cgi-bin/www-STS_Pipeline), or GeneUp (Pesole et al., *BioTechniques* 25:112-123, 1998), for example, can be used to identify potential PCR primers.

Furthermore, sequence comparisons can be done to find nucleic acid molecules of the present invention based on secondary structure homology. Several methods and programs are available to predict and compare secondary structures of nucleic acid molecules, for example, GeneBee (available on the world wide web at genebee.msu.su/services/rna2_reduced.html); the Vienna RNA Package (available on the world wide web at tbi.univie.ac.at/~ivo/RNA/); Sstruct-View (available on the world wide web at the Stanford Medical Informatics website, under: projects/helix/sstructview/home.html and described in "RNA Secondary Structure as a Reusable Interface to Biological Information Resources." 1997. *Gene* vol. 190GC59-70). For example, comparisons of secondary structure are preformed in Le et al., A common RNA structural motif involved in the internal initiation of translation of cellular mRNAs. 1997. *Nuc. Acid. Res.* vol. 25(2):362-369.

Constructs of the Present Invention

The present invention includes and provides nucleic acid constructs. It is understood that any of the constructs and other nucleic acid agents of the present invention can be either DNA or RNA. In a preferred embodiment, a construct can be a nucleic acid molecule having a UTR, a coding sequence, or both. In another embodiment, a construct is composed of at least one UTR of the present invention, a sequence encoding a reporter polypeptide, and a vector. Moreover, any of the nucleic acid molecules of the present invention can be used in combination with a method of the present invention.

Vectors

Exogenous genetic material may be introduced into a host cell by use of a vector or construct designed for such purpose. Any of the nucleic acid sequences of the present invention can be incorporated into a vector or construct of the present invention. A vector or construct of the present invention includes, without limitation, linear or closed circular plasmids. A vector system may be a single vector or plasmid or two or more vectors or plasmids that together contain the total DNA to be introduced into the genome of the host. In a preferred embodiment, a vector contains a promoter functional in mammalian cells or bacteria or both. Means for preparing vectors or constructs are well known in the art.

Vectors suitable for replication in mammalian cells may include viral replicons, or sequences that insure integration of the appropriate sequences encoding HCV epitopes into the host genome. For example, another vector used to express foreign DNA is vaccinia virus. Such heterologous DNA is generally inserted into a gene that is non-essential to the virus, for example, the thymidine kinase gene (tk), which also provides a selectable marker. Expression of the HCV polypeptide then occurs in cells or animals that are infected with the live recombinant vaccinia virus.

In general, plasmid vectors containing replicon and control sequences that are derived from species compatible with the host cell are used in connection with bacterial hosts. The vector ordinarily carries a replication site, as well as marking sequences that are capable of providing phenotypic selection in transformed cells. For example, *E. coli* is typically transformed using a construct with a backbone derived from a vector, such as pBR322, which contains genes for ampicillin and tetracycline resistance and thus provides easy means for identifying transformed cells. The pBR322 plasmid, or other microbial plasmid or phage, also generally contains, or is modified to contain, promoters that can be used by the microbial organism for expression of the selectable marker genes.

In a preferred embodiment of the present invention, an expression vector can be a high-level mammalian expression vector designed to randomly integrate into the genome, for example, pCMR1. In another preferred embodiment of the present invention, an expression vector can be a high-level mammalian expression vector designed to site-specifically integrate into the genome of cells. For example, pMCP1 can site-specifically integrate into the genome of cells genetically engineered to contain the FRT site-specific recombination site via the Flp recombinase (see, e.g., Craig, 1988, *Ann. Rev. Genet.* 22: 77-105; and Sauer, 1994, *Curr. Opin. Biotechnol.* 5: 521-527).

Promoters

A construct can include a promoter, e.g., a recombinant vector typically comprises, in a 5' to 3' orientation: a promoter to direct the transcription of a nucleic acid molecule of interest.

In a preferred aspect of the present invention, a construct can include a mammalian promoter and can be used to express a nucleic acid molecule of choice. As used herein, a "mammalian promoter" refers to a promoter functional in a mammalian cell derived from a mammalian cell or both. A number of promoters that are active in mammalian cells have been described in the literature. A promoter can be selected on the basis of the cell type into which the vector will be inserted.

A preferred promoter of the present invention is a VEGF promoter. In addition to VEGF promoters described previously, other promoter sequences can be utilized in a construct or other nucleic acid molecule. Suitable promoters include, but are not limited to, those described herein.

Suitable promoters for mammalian cells are known in the art and include viral promoters, such as those from Simian Virus 40 (SV40), Rous sarcoma virus (RSV), adenovirus (ADV), cytomegalovirus (CMV), and bovine papilloma virus (BPV), and the parvovirus B19p6 promoter as well as mammalian cell-derived promoters. A number of viral-based expression systems can be used to express a reporter gene in mammalian host cells. For example, if an adenovirus is used as an expression vector, sequences encoding a reporter gene can be ligated into an adenovirus transcription/translation complex comprising the late promoter and tripartite leader sequence.

Other examples of preferred promoters include tissue-specific promoters and inducible promoters. Other preferred promoters include the hematopoietic stem cell-specific, e.g., CD34, glucose-6-phosphotase, interleukin-1 alpha, CD11c integrin gene, GM-CSF, interleukin-5R alpha, interleukin-2, c-fos, h-ras and DMD gene promoters. Other promoters include the herpes thymidine kinase promoter, and the regulatory sequences of the metallothionein gene.

Inducible promoters suitable for use with bacteria hosts include the β-lactamase and lactose promoter systems, the arabinose promoter system, alkaline phosphatase, a tryptophan (trp) promoter system and hybrid promoters such as the tac promoter. However, other known bacterial inducible promoters are suitable. Promoters for use in bacterial systems also generally contain a Shine-Dalgarno sequence operably linked to the DNA encoding the polypeptide of interest.

A promoter can also be selected on the basis of their regulatory features, e.g., enhancement of transcriptional activity, inducibility, tissue specificity, and developmental stage-specificity. A promoter can work in vitro, for example the T7-promoter. Particularly preferred promoters can also be used to express a nucleic acid molecule of the present invention in a nonhuman mammal. Additional promoters that may be utilized are described, for example, in Bernoist and Chambon, *Nature* 290:304-310 (1981); Yamamoto et al., *Cell* 22:787-797 (1980); Wagner et al., *PNAS* 78:1441-1445 (1981); Brinster et al., *Nature* 296:39-42 (1982).

Reporter Genes

As used herein, a "reporter gene" is any gene whose expression can be measured. In a preferred embodiment, a reporter gene does not have any UTRs. In a more preferred embodiment, a reporter gene is a contiguous open reading frame. In another preferred embodiment, a reporter gene can have a previously determined reference range of detectable expression.

Constructs of the invention can comprise one or more reporter genes fused to one or more UTRs. For example, specific RNA sequences, RNA structural motifs, and/or RNA structural elements that are known or suspected to modulate UTR-dependent expression of a target gene can be fused to the reporter gene. A reporter gene of the present invention encoding a protein, a fragment thereof, or a polypeptide, can also be linked to a propeptide encoding region. A propeptide is an amino acid sequence found at the amino terminus of a proprotein or proenzyme. Cleavage of the propeptide from the proprotein yields a mature biochemically active protein. The resulting polypeptide is known as a propolypeptide or proenzyme (a zymogen in some cases). Propolypeptides are generally inactive and can be converted to mature active polypeptides by catalytic or autocatalytic cleavage of the propeptide from the propolypeptide or proenzyme.

A reporter gene can express a selectable or screenable marker. Selectable markers may also be used to select for organisms or cells that contain exogenous genetic material. Examples of such include, but are not limited to: a neo gene, which codes for kanamycin resistance and can be selected for using kanamycin, GUS, neomycin phosphotransferase II (nptII), or an antibiotic resistance coding sequence. Screenable markers can be used to monitor expression. Exemplary screenable markers include: green fluorescent protein (GFP), luciferase (LUX), a β-glucuronidase or uidA gene (GUS) which encodes an enzyme for which various chromogenic substrates are known; a β-lactamase gene, a gene which encodes an enzyme for which various chromogenic substrates are known (e.g., PADAC, a chromogenic cephalosporin); a luciferase gene; a tyrosinase gene, which encodes an enzyme capable of oxidizing tyrosine to DOPA and dopaquinone which in turn condenses to melanin; and α-galactosidase, which can turn a chromogenic α-galactose substrate.

Included within the terms "selectable or screenable marker genes" are also genes that encode a secretable marker whose secretion can be detected as a means of identifying or selecting for transformed cells. Examples include markers that encode a secretable antigen that can be identified by antibody interaction, or even secretable enzymes, which can be detected utilizing their inherent properties. Secretable proteins fall into a number of classes, including small, diffusible proteins which are detectable, (e.g., by ELISA), or small active enzymes which are detectable in extracellular solution (e.g., α-amylase, β-lactamase, phosphinothricin transferase). Other possible selectable or screenable marker genes, or both, are apparent to those of skill in the art.

A reporter gene can express a fusion protein. As such, the fusion protein can be a fusion of any reporter gene operably linked to another gene, or fragment thereof. For instance, the expressed fusion protein can provide a "tagged" epitope to facilitate detection of the fusion protein, such as GST, GFP, FLAG, or polyHIS. Such fusions preferably encode between 1 and 50 amino acids, more preferably between 5 and 30 additional amino acids, and even more preferably between 5 and 20 amino acids. In one embodiment, a fusion protein can be a fusion protein that includes in whole or in part of a VEGF protein sequence.

Alternatively, the fusion can provide regulatory, enzymatic, cell signaling, or intercellular transport functions. For example, a sequence encoding a signal peptide can be added to direct a fusion protein to a particular organelle within a eukaryotic cell. Such fusion partners preferably encode between 1 and 1000 additional amino acids, more preferably between 5 and 500 additional amino acids, and even more preferably between 10 and 250 amino acids.

The present invention also provides for a reporter gene flanked by one or more untranslated regions (e.g., the 5' UTR, 3' UTR, or both the 5' UTR and 3' UTR of the target gene). In addition, the present invention provides for a reporter gene flanked by one or more UTRs of a target gene, where the UTR contains one or more mutations (e.g., one or more substitutions, deletions and/or additions). In a preferred embodiment, the reporter gene is flanked by both 5' and 3' UTRs so that compounds that interfere with an interaction between the 5' and 3' UTRs can be identified.

In another preferred embodiment, a stable hairpin secondary structure is inserted into the UTR, preferably the 5' UTR of the target gene. For example, in cases where the 5' UTR possesses IRES activity, the addition of a stable hairpin secondary structure in the 5' UTR can be used to separate cap-dependent from cap-independent translation (see, e.g., Muhlrad et al., 1995, *Mol. Cell. Biol.* 15(4):2145-56, the disclosure of which is incorporated by reference in its entirety). In another embodiment, an intron is inserted into a UTR (preferably, the 5' UTR) or at the 5' end of an ORF of a target gene. For example, but not by limitation, in cases where an RNA possesses instability elements, an intron, e.g., the human elongation factor one alpha (EF-1 alpha) first intron, can be cloned into a UTR (preferably, the 5' UTR) or a 5' end of the ORF to increase expression (see, e.g., Kim et al., 2002, *J Biotechnol* 93(2):183-7, the disclosure of which is incorporated by reference in its entirety). In a preferred embodiment, both a stable hairpin secondary structure and an intron are added to the reporter gene construct. In a more preferred embodiment, the stable hairpin secondary structure is cloned into the 5' UTR and the intron is added at the 5' end of the main ORF of the reporter gene.

The reporter gene can be positioned such that the translation of that reporter gene is dependent upon the mode of translation initiation, such as, but not limited to, cap-dependent translation or cap-independent translation (i.e., translation via an internal ribosome entry site). Alternatively, where the UTR contains an upstream open reading frame, the reporter gene can be positioned such that the reporter protein is translated only in the presence of a compound that shifts the reading frame of the UTR so that the formerly untranslated open reading frame is then translated.

The reporter gene constructs can be monocistronic or multicistronic. A multicistronic reporter gene construct may encode 2, 3, 4, 5, 6, 7, 8, 9, 10 or more, or in the range of 2-5, 5-10 or 10-20 reporter genes. For example, a dicistronic reporter gene construct comprising, in the following order going downstream, a promoter, a first reporter gene, a 5' UTR of a target gene, a second reporter gene and optionally, a 3' UTR of a target gene. In such a reporter construct, the transcription of both reporter genes is capable of being driven by the promoter. In this example construct, the present invention includes the translation of the mRNA from the first reporter gene by a cap-dependent scanning mechanism and the translation of the mRNA from the second reporter gene by a cap-independent mechanism, for example by an IRES. In such a case, the IRES-dependent translation of a mRNA of the second reporter gene can be normalized against the cap-dependent translation.

Reporter genes can be expressed in vitro or in vivo. In vivo expression can be in a suitable bacterial or eukaryotic host. Suitable methods for expression are described by Sambrook et al., *Molecular Cloning: A Laboratory Manual*, Second Edition, Cold Spring Harbor Laboratory Press, Cold Spring Harbor, N.Y. (1989); Haymes et al., *Nucleic Acid Hybridization, A Practical Approach*, IRL Press, Washington, D.C. (1985); or similar texts. Fusion protein or peptide molecules of the invention are preferably produced via recombinant means. These proteins and peptide molecules can be derivatized to contain carbohydrate or other moieties (such as keyhole limpet hemocyanin, etc.).

Linked

As used herein, linked means physically linked, operably linked, flanked, or any of these in combination.

As used herein, physically linked means that the physically linked nucleic acid sequences are located on the same nucleic acid molecule, for example a promoter can be physically linked to a reporter gene as part of a construct. A physical linkage can be proximal, and either direct or indirect. In a preferred embodiment, the promoter is operably linked and physically linked to a nucleic acid sequence of the present invention.

A preferred embodiment of the present invention also provides for specific nucleic acid molecules containing a reporter gene flanked by one or more UTRs of a target gene. In this preferred embodiment, the one or more UTRs of a target gene can be physically linked, operably linked, or operably and physically linked to the reporter gene. The present invention also provides for a reporter gene flanked by one or more UTRs of a target gene, where one or more of the UTRs contains one or more mutations (e.g., one or more of each substitution, deletion, addition, or any combination of each). In a more-preferred embodiment of the present invention, a reporter gene is flanked by a 5' UTR of a VEGF gene containing one or more deletions. In a most preferred embodiment, a reporter gene is flanked by and operably linked to a 5' VEGF UTR in the absence of a NeRP.

In a preferred embodiment, the reporter gene is flanked by both 5' and 3' UTRs of one or more target genes so that compounds that interfere with an interaction between the 5' and 3' UTRs can be identified. In a more preferred embodiment, the reporter gene is flanked by a 5' and 3' UTRs of one target gene, and the reporter gene is physically, operably, or physically and operably linked to the UTRs of one target gene. In a most preferred embodiment, a reporter gene is proximally linked, either directly or indirectly, to one or more UTRs of a target gene. If the reporter gene is directly linked to a UTR of a target gene, the last nucleic acid residue of the reporter gene is chemically bonded to the first nucleic acid residue of the UTR of a target gene. If the reporter gene is proximally linked indirectly to a UTR of a target gene, the last nucleic acid residue of the reporter gene is not chemically bonded to the first nucleic acid residue of the UTR of a target gene and the last nucleic acid residue of the reporter gene can be about 3 or greater than 5 but less than 20. If the reporter gene is directly linked to a UTR of a target gene at any time during reporter gene processing, such as after a splicing event, the reporter gene is directly linked to the UTR.

UTRs

Agents and constructs of the invention include nucleic acid molecules with an untranslated region (UTR). In a preferred aspect, a UTR refers to a UTR of an mRNA, i.e. the region of the mRNA that is not translated into protein. In a preferred embodiment, a UTR contains one or more regulatory elements that modulate UTR-dependent regulation of gene expression. In a particularly preferred embodiment, a UTR is a 5' UTR, i.e., upstream of the coding region, or a 3' UTR, i.e., downstream of the coding region. In another particularly preferred embodiment, the 5' UTR includes a VEGF promoter. In a more preferred embodiment, the 5' UTR includes a VEGF promoter and a PTCRE.

As used herein, a "main ORF" is a nucleic acid sequence, including sequence contained in deoxyribonucleic acid and ribonucleic acid molecules, having an open reading frame that can be translated. Examples of a main ORF include a reporter gene, a target gene, and a control gene. As used herein, a "target gene" can be any gene. In a preferred embodiment, a target gene is a gene operatively linked downstream of a VEGF 5' UTR containing an upstream open reading frame ("uORF"). In another embodiment, a target gene can be a VEGF main ORF. In a preferred embodiment, a target gene is a gene containing a uORF. In a particularly preferred embodiment, a target gene is a gene having greater than 50% identity greater than 200 residues with respect to a VEGF gene. As used herein, a "control gene" can be any gene. In a preferred embodiment, a control gene is a gene operatively linked downstream of a VEGF 5' UTR that does not contain a NeRP.

A UTR of the present invention can be operatively, physically, or operatively and physically linked to a reporter gene. In a preferred embodiment of the present invention, a UTR of the present invention is physically linked to a reporter gene. The physical, operable, or physical and operable linkage may be upstream, downstream, or internal to the reporter gene. As used herein, operably linked means that the operably linked nucleic acid sequences exhibit their deserved function. For example, a promoter can be operably linked to a reporter gene.

In a preferred aspect of the present invention, a UTR of the present invention is a VEGF 5' UTR physically linked upstream of a reporter gene. In a particularly preferred embodiment, VEGF 5' UTR contains or consists of SEQ ID NO: 3 and is physically linked downstream of a reporter gene. In another embodiment, a VEGF 5' UTR does not contain or consist of a NeRP and is physically and operatively linked upstream of a reporter gene. In a more particularly preferred embodiment, VEGF 5' UTR does not contain or consist of a NeRP and does contain or consist of a PTCRE and is physically and operatively linked upstream of a reporter gene.

In a preferred embodiment of the present invention, a UTR of the present invention is physically linked upstream to a reporter gene and another UTR is physically linked downstream of the reporter gene. In a particularly preferred embodiment, a UTR of the present invention contains or consists of SEQ ID NO: 3 and is physically and operatively linked upstream of a reporter gene and a VEGF 3' UTR is physically and operatively linked downstream of a reporter gene.

In a preferred embodiment of the present invention, a UTR of the present invention is physically linked to reporter gene containing an intron. In a more preferred embodiment of the present invention, a UTR of the present invention containing SEQ ID NO: 3 is physically linked to a reporter gene containing an intron. In a preferred embodiment of the present invention, a UTR of the present invention is physically linked upstream of a reporter gene and contains an intron internal to the UTR.

In a preferred embodiment of the present invention, a UTR of the present invention is physically linked upstream of a reporter gene and a UTR is physically linked downstream of the reporter gene. In a more preferred embodiment of the present invention, a VEGF 5' UTR of the present invention containing a SEQ ID NO: 3 is physically linked upstream of a reporter gene and a VEGF 3' UTR is physically linked downstream of the reporter gene.

PTCREs and NeRPs

As referred to herein, a PTCRE is a post-transcriptional regulatory element that modulates expression of a target gene. In one aspect, a PTCRE is not a full-length sequence of a target UTR. In a preferred aspect, a PTCRE is not a full-length VEGF 5' UTR. In one embodiment, a PTCRE in one target gene can have primary nucleic acid sequence similarity to a PTCRE in a different target gene. Alternatively, there may not be any primary nucleic acid sequence similarity in PTCREs of similar function. In a preferred embodiment, a PTCRE in one target gene can have a secondary, tertiary, or secondary and tertiary structure similar to a PTCRE in a different target gene. Examples of PTCREs include, but are not limited to, IRES elements, upstream ORFs, and AREs.

In one embodiment, a PTCRE is a nucleic acid sequence in a UTR, which modulates UTR-dependent expression. A PTCRE can be a nucleic acid sequence selected from the group consisting of an iron response element ("IRE"), Internal ribosome entry site ("IRES"), upstream open reading frame ("uORF"), male specific lethal element ("MSL-2"), G quartet element, and 5'-terminal oligopyrimidine tract ("TOP"), AU-rich element ("ARE"), selenocysteine insertion sequence ("SECIS"), histone stem loop, cytoplasmic polyadenylation element ("CPE"), nanos translational control element, amyloid precursor protein element ("APP"), translational regulation element ("TGE")/direct repeat element ("DRE"), Bruno element ("BRE"), or a 15-lipoxygenase differentiation control element ("15-LOX-DICE"). In an alternative embodiment, a PTCRE is not an IRES from VEGF. In another embodiment, PTCRE is not be an IRES. In a preferred embodiment, a PTCRE is SEQ ID NO: 3. In a most preferred embodiment, a PTCRE is not a NeRP and the PTCRE does not contain or consist of a NeRP.

A NeRP is a nucleic acid sequence in a UTR, which modulates PTCRE-dependent expression in a NeRP-dependent mechanism. In one embodiment of the present invention, a NeRP regulates an IRES. In a preferred embodiment, a NeRP suppresses IRES-dependent expression of a gene. In a most preferred embodiment, a NeRP is SEQ ID NO: 4. Alternatively, a NeRP can modulate PTCRE-dependent expression, where the PTCRE suppresses gene expression, so that the NeRP is capable of increasing gene expression by a NeRP-dependent mechanism. In an alternative embodiment of the invention, a NeRP mimics an IRES.

A NeRP of the present invention can differ from any of the residues in SEQ ID NO: 4 in that the nucleic acid sequence has been deleted, substituted, or added in a manner that does not alter the function. In another aspect of the present invention, a NeRP of the present invention consists or comprises SEQ ID NO: 9, and fragments and complements of all. In another aspect of the present invention, a NeRP of the present invention consists or comprises SEQ ID NOs: 10-12, and fragments and complements of all.

While the present invention is directed, in part, to VEGF 5' UTRs, PTCREs of the present invention can be located in any position within a construct and not limited to the 5' UTR region of a construct. A PTCRE of the present invention can be operatively, physically, or operatively and physically linked to a UTR. In an alternative embodiment of the present invention, a PTCRE of the present invention is a UTR of the present invention.

While the present invention is directed, in part, to a NeRP in the VEGF 5' UTR, NeRPs of the present invention can be located in any position within a construct and not limited to the VEGF 5' UTR region of a construct. A NeRP of the present invention can be operatively, physically, or operatively and physically linked to a UTR. In an alternative embodiment of the present invention, a NeRP of the present invention is upstream of a PTCRE of the present invention.

In a preferred embodiment, a PTCRE of the present invention is located between about 1 to about 100 residues upstream from the initiation codon of an open reading frame in a mRNA, between about 150 to about 250 residues upstream from the initiation codon, or between about 300 to about 500 residues upstream from the initiation codon. In a most preferred embodiment, the untranslated region is about 1 residue upstream from the initiation codon.

In a preferred embodiment, a NeRP of the present invention is between about 1000 to about 500 residues upstream from a PTCRE, between about 500 to about 100 residues upstream from a PTCRE, or between about 100 to about 60 residues upstream from a PTCRE. In another embodiment, a PTCRE is within about 1000 residues upstream from the 5' end of a main ORF, about 500 residues upstream from the 5' end of a main ORF, or within about 200 residues upstream from the 5' end of a main ORF, or about 100 residues upstream from the 5' end of a main ORF. In another embodiment, a PTCRE is within the main ORF and between about 1000 to about 500 residues upstream from the 3' end of a main ORF, between about 500 to about 100 residues upstream from the 3' end of a main ORF, or between about 100 to about 60 residues upstream from the 3' end of a main ORF. In a most preferred embodiment, the PTCRE is within 30 residues upstream from the 5' end of a main ORF.

Constructs of the present invention can have more or fewer components than described above. For example, constructs of the present invention can include genetic elements, including but not limited to, 3' transcriptional terminators, 3' polyadenylation signals, other untranslated nucleic acid sequences, transit or targeting sequences, selectable or screenable markers, promoters, enhancers, and operators, as desired. Constructs of the present invention can also contain a promoterless gene that may utilize an endogenous promoter upon insertion into a host cell chromosome.

Alternatively, sequences encoding nucleic acid molecules of the present invention can be cloned into a vector for the production of an mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (for example, Amersham Biosciences Inc., Piscataway, N.J.; and Promega Co, Madison, Wis.).

Modulation of Gene Expression by Nucleic Acid Molecules of the Present Invention Modulation of gene expression can result in more or less gene expression. Many approaches for modulating gene expression using nucleic acid molecules of the present invention are known to one skilled in the art. For example, overexpression of a gene product can be the result from transfection of a construct of the present invention into a mammalian cell. Similarly, down-regulation can be the result from transfection of a construct of the present invention into a mammalian cell. Other non-limiting examples include anti-sense techniques like RNA interference (RNAi), transgenic animals, hybrids, and ribozymes. The following examples are provided by way of illustration, and are not intended to be limiting of the present invention.

Cellular Mechanisms

As used herein, the term "UTR-dependent expression" refers to the regulation of gene expression through UTRs at the level of mRNA expression, i.e., after transcription of the gene has begun until the protein or the RNA product(s) encoded by the gene has degraded. In a preferred embodiment, the term "UTR-dependent expression" refers to the regulation of mRNA stability or translation. In a more preferred embodiment, the term "UTR-dependent expression" refers to the regulation of gene expression through regulatory elements present in an UTR(s). Altering the sequence of a PTCRE within a UTR of target gene may change the amount of UTR-dependent expression observed for that target gene.

As used herein, a "UTR-affected mechanism" is a cellular mechanism that discriminates between UTRs based on their nucleic acid sequence or based on properties that are a function of their sequence such as the secondary, tertiary, or quaternary structure or other associated factors. Modulation of the UTR-dependent expression of a target gene can be due to a change in how a UTR-affected mechanism acts on the target gene. For example, a UTR in a target gene can contain an IRES, which affects target gene expression via a UTR-affected mechanism.

In a preferred embodiment, a UTR-affected mechanism can be a main ORF-independent mechanism. As used herein, a "main ORF-independent mechanism" refers to a cellular pathway or process, wherein at least one step relates to gene expression and is not dependent on the nucleic acid sequence of the main open reading frame. In a preferred embodiment, a UTR-affected mechanism is a main ORF-independent, UTR-affected mechanism.

In order to exclude the possibility that a particular compound is functioning solely by modulating the expression of a target gene in an UTR-independent manner, one or more mutations may be introduced into the UTRs operably linked to a reporter gene and the effect on the expression of the reporter gene in a reporter gene-based assay described herein can be determined. For example, a reporter gene construct comprising the 5' UTR of a target gene may be mutated by deleting a fragment of the 5' UTR of the target gene or substituting a fragment of the 5' UTR of the target gene with a fragment of the 5' UTR of another gene and measuring the expression of the reporter gene in the presence and absence of a compound that has been identified in a screening assays of the present invention or of an assay well known to the skilled artisan. If the deletion of a fragment of the 5' UTR of the target gene or the substitution of a fragment of the 5' UTR of the target gene with a fragment of the 5' UTR of another gene affects the ability of the compound to modulate the expression of the reporter gene, then the fragment of the 5' UTR deleted or substituted plays a role in the regulation of the reporter gene expression and the regulation, at least in part, in an UTR-dependent manner.

Alternatively or in conjunction with tests described above, the possibility that a particular compound is functioning solely by modulating the expression of a target gene in an UTR-independent manner can be determined by changing the vector utilized as a reporter construct. The UTRs flanked by a reporter gene from the first reporter construct in which an effect on reporter gene expression was detected following exposure to a compound may be inserted into a new reporter construct that has, e.g., different transcriptional regulation elements (e.g., a different promoter) and a different selectable marker. The level of reporter gene expression in the presence of the compound can be compared to the level of reporter gene expression in the absence of the compound or in the presence of a control (e.g., PBS). If there is no change in the level of expression of the reporter gene in the presence of the compound relative to the absence of the compound or in the presence of a control, then the compound probably is functioning in an UTR-independent manner.

Compounds, identified in assays of the present invention, that are capable of modulating UTR-dependent expression of a target gene (for convenience referred to herein as a "lead" compound) can be further tested for UTR-dependent binding to the target RNA (which contains at least one UTR, and preferably at least one element of an UTR, for example a PTCRE). Furthermore, by assessing the effect of a compound on target gene expression, cis-acting elements, i.e., specific nucleotide sequences, that are involved in UTR-dependent expression may be identified. RNA binding assays, subtraction assays, and expressed protein concentration and activity assays are examples of methods to determine UTR-dependent expression of a gene.

Hybrids

In one aspect of the present invention, a hybrid of a compound and a PTCRE or a NeRP of the present invention is a hybrid formed between two non-identical molecules. In a preferred aspect, a hybrid can be formed between two nucleic acid molecules. For example, a hybrid can be formed between two ribonucleic acid molecules, between a ribonucleic acid molecule and a deoxyribonucleic acid molecule, or between derivatives of either. In alternative embodiment, a hybrid can be formed between a nucleic acid of the present invention and a non-nucleic acid molecule. In a preferred embodiment, a hybrid can be formed between a nucleic acid molecule and a non-nucleic acid molecule, for example, a polypeptide or a non-peptide therapeutic agent.

Ribozymes

In one aspect of the present invention, the activity or expression of a gene is regulated by designing trans-cleaving catalytic RNAs (ribozymes) specifically directed to a nucleic acid molecule of the present invention, for example, SEQ ID NO: 3 and SEQ ID NOs: 5-8. In an alternate aspect, the activity or expression of a gene is regulated by designing trans-cleaving catalytic RNAs (ribozymes) specifically directed to a nucleic acid molecule of the present invention, for example, SEQ ID NO: 4 and SEQ ID NOs: 9-12.

Ribozymes are RNA molecules possessing endoribonuclease activity. Ribozymes are specifically designed for a particular target, and the target message contains a specific nucleotide sequence. They are engineered to cleave any RNA species site-specifically in the background of cellular RNA. The cleavage event renders the mRNA unstable and prevents protein expression. Importantly, ribozymes can be used to inhibit expression of a gene of unknown function for the purpose of determining its function in an in vitro or in vivo context, by detecting a phenotypic effect.

One commonly used ribozyme motif is the hammerhead, for which the substrate sequence requirements are minimal. Design of the hammerhead ribozyme, and the therapeutic uses of ribozymes, are disclosed in Usman et al., *Current Opin. Strict. Biol.* 6:527-533 (1996). Ribozymes can also be prepared and used as described in Long et al., *FASEB J.* 7:25 (1993); Symons, *Ann. Rev. Biochem.* 61:641 (1992); Perrotta et al., *Biochem.* 31:16-17 (1992); Ojwang et al., *PNAS* 89:10802-10806 (1992); and U.S. Pat. No. 5,254,678.

Ribozyme cleavage of HIV-I RNA, methods of cleaving RNA using ribozymes, methods for increasing the specificity of ribozymes, and the preparation and use of ribozyme fragments in a hammerhead structure are described in U.S. Pat. Nos. 5,144,019; 5,116,742; and 5,225,337 and Koizumi et al., *Nucleic Acid Res.* 17:7059-7071 (1989). Preparation and use of ribozyme fragments in a hairpin structure are described by Chowrira and Burke, *Nucleic Acids Res.* 20:2835 (1992). Ribozymes can also be made by rolling transcription as described in Daubendiek and Kool, *Nat. Biotechnol.* 15(3):273-277 (1997).

The hybridizing region of the ribozyme may be modified or may be prepared as a branched structure as described in Horn and Urdea, *Nucleic Acids Res.* 17:6959-67 (1989). The basic structure of the ribozymes may also be chemically altered in ways familiar to those skilled in the art, and chemically synthesized ribozymes can be administered as synthetic oligonucleotide derivatives modified by monomeric units. In a therapeutic context, liposome mediated delivery of ribozymes improves cellular uptake, as described in Birikh et al., *Eur. J. Biochem.* 245:1-16 (1997).

Ribozymes of the present invention also include RNA endoribonucleases (hereinafter "Cech-type ribozymes") such as the one which occurs naturally in *Tetrahymena thermophila* (known as the IVS, or L-19 IVS RNA) and which has been extensively described by Thomas Cech and collaborators (Zaug et al., *Science* 224:574-578 (1984); Zaug and Cech, *Science* 231:470-475 (1986); Zaug et al., *Nature*, 324:429-433 (1986); WO 88/04300; Been and Cech, *Cell* 47:207-216 (1986)). The Cech-type ribozymes have an eight base pair active site which hybridizes to a target RNA sequence whereafter cleavage of the target RNA takes place. The invention encompasses those Cech-type ribozymes which target eight base-pair active site sequences that are present in a target gene.

Ribozymes can be composed of modified oligonucleotides (e.g., for improved stability, targeting, etc.) and should be delivered to cells which express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous messages and inhibit translation. Because ribozymes, unlike antisense molecules, are catalytic, a lower intracellular concentration is required for efficiency.

Using the nucleic acid sequences of the invention and methods known in the art, ribozymes are designed to specifically bind and cut the corresponding mRNA species. Ribozymes thus provide a means to inhibit the expression of any of the proteins encoded by the disclosed nucleic acids or their full-length genes. The full-length gene need not be known in order to design and use specific inhibitory ribozymes. In the case of a nucleic acid or cDNA of unknown function, ribozymes corresponding to that nucleotide sequence can be tested in vitro for efficacy in cleaving the target transcript. Those ribozymes that effect cleavage in vitro are further tested in vivo. The ribozyme can also be used to generate an animal model for a disease, as described in Birikh et al., *Eur. J. Biochem.* 245:1-16 (1997). An effective ribozyme is used to determine the function of the gene of interest by blocking its transcription and detecting a change in the cell. Where the gene is found to be a mediator in a disease, an effective ribozyme is designed and delivered in a gene therapy for blocking transcription and expression of the gene.

Therapeutic and functional genomic applications of ribozymes begin with knowledge of a portion of the coding sequence of the gene to be inhibited. Thus, for many genes, a partial nucleic acid sequence provides adequate sequence for constructing an effective ribozyme. A target cleavage site is selected in the target sequence, and a ribozyme is constructed based on the 5' and 3' nucleotide sequences that flank the cleavage site. Retroviral vectors are engineered to express monomeric and multimeric hammerhead ribozymes targeting the mRNA of the target coding sequence. These monomeric and multimeric ribozymes are tested in vitro for an ability to cleave the target mRNA. A cell line is stably transduced with the retroviral vectors expressing the ribozymes, and the transduction is confirmed by Northern blot analysis and reverse-transcription polymerase chain reaction (RT-PCR). The cells are screened for inactivation of the target mRNA by such indicators as reduction of expression of disease markers or reduction of the gene product of the target mRNA.

Cells and Organisms

Nucleic acid molecules that may be used in cell transformation or transfection can be any of the nucleic acid molecules of the present invention. Nucleic acid molecules of the present invention can be introduced into a cell or organism. In a preferred aspect, the cell is selected from the group consisting of cells that do not express VEGF, cells that express VEGF, or cells that express VEGF conditionally. In a more preferred aspect, the cell is a cancer cell, more preferably a cancer cell where VEGF is overexpressed relative to a non-transformed cell.

A host cell strain can be chosen for its ability to modulate the expression of the inserted sequences, to process an expressed reporter gene in the desired fashion, or based on the expression levels of an endogenous or heterologous VEGF gene. Mammalian cell lines available as hosts for expression are known in the art and include many immortalized cell lines available from the American Type Culture Collection (ATCC, Manassas, Va.), such as HeLa cells, Chinese hamster ovary (CHO) cells, baby hamster kidney (BHK) cells and a number of other cell lines. Non-limiting examples of suitable mammalian host cell lines include those shown below in Table 1.

TABLE 1

Mammalian Host Cell Lines

| Host Cell | Origin | Source |
|---|---|---|
| HepG-2 | Human Liver Hepatoblastoma | ATCC HB 8065 |
| CV-1 | African Green Monkey Kidney | ATCC CCL 70 |
| LLC-MK$_2$ | Rhesus Monkey Kidney | ATCC CCL 7 |
| 3T3 | Mouse Embryo Fibroblasts | ATCC CCL 92 |
| AV12-664 | Syrian Hamster | ATCC CRL 9595 |
| HeLa | Human Cervix Epitheloid | ATCC CCL 2 |
| RPMI8226 | Human Myeloma | ATCC CCL 155 |
| H4IIEC3 | Rat Hepatoma | ATCC CCL 1600 |
| C127I | Mouse Fibroblast | ATCC CCL 1616 |
| 293 | Human Embryonal Kidney | ATCC CRL 1573 |
| HS-Sultan | Human Plasma Cell Plasmocytoma | ATCC CCL 1484 |
| BHK-21 | Baby Hamster Kidney | ATCC CCL 10 |
| CHO-K1 | Chinese Hamster Ovary | ATCC CCL 61 |

In a preferred aspect, cells of the present invention can be cells of an organism. In a more preferred aspect, the organism is a mammal. In a most preferred aspect, the mammal is a human. In another more preferred aspect, the organism is a non-human mammal, preferably a mouse, rat, or a chimpanzee. In one aspect of the present invention, cells can be pluripotent or differentiated.

A nucleic acid of the present invention can be naturally occurring in the cell or can be introduced using techniques such as those described in the art. There are many methods for introducing transforming DNA segments into cells, but not all are suitable for delivering DNA to eukaryotic cells. Suitable methods include any method by which DNA can be introduced into a cell, such as by direct delivery of DNA, by desiccation/inhibition-mediated DNA uptake, by electroporation, by agitation with silicon carbide fibers, by acceleration of DNA coated particles, by chemical transfection, by lipofection or liposome-mediated transfection, by calcium chloride-mediated DNA uptake, etc. For example, without limitation, Lipofectamine® (Invitrogen Co., Carlsbad, Calif.) and Fugene® (Hoffmann-La Roche Inc., Nutley, N.J.) can be used for transfection of nucleic acid molecules, such as constructs and siRNA, into several mammalian cells. Alternatively, in certain embodiments, acceleration methods are preferred and include, for example, microprojectile bombardment and the like. Within the scope of this invention, the transfected nucleic acids of the present invention may be expressed transciently or stably. Such transfected cells can be in a two- or three-dimensional cell culture system or in an organism.

For example, without limitation, the construct may be an autonomously replicating construct, i.e., a construct that exists as an extrachromosomal entity, the replication of which is independent of chromosomal replication, e.g., a plasmid, an extrachromosomal element, a minichromosome, or an artificial chromosome. The construct may contain any means for assuring self-replication. For autonomous replication, the construct may further comprise an origin of replication enabling the construct to replicate autonomously in the host cell in question. Alternatively, the construct may be one which, when introduced into the cell, is integrated into the genome and replicated together with the chromosome(s) into which it has been integrated. This integration may be the result of homologous or non-homologous recombination.

Integration of a construct or nucleic acid into the genome by homologous recombination, regardless of the host being considered, relies on the nucleic acid sequence of the construct. Typically, the construct contains nucleic acid sequences for directing integration by homologous recombination into the genome of the host. These nucleic acid sequences enable the construct to be integrated into the host cell genome at a precise location or locations in one or more chromosomes. To increase the likelihood of integration at a precise location, there should be preferably two nucleic acid sequences that individually contain a sufficient number of nucleic acids, preferably 400 residues to 1500 residues, more preferably 800 residues to 1000 residues, which are highly homologous with the corresponding host cell target sequence. This enhances the probability of homologous recombination. These nucleic acid sequences may be any sequence that is homologous with a host cell target sequence and, furthermore, may or may not encode proteins.

Stable expression is preferred for long-term, high-yield production of recombinant proteins. For example, cell lines that stably express a reporter gene can be transformed using expression constructs that can contain viral origins of replication and/or endogenous expression elements and a selectable marker gene on the same or on a separate construct. Following the introduction of the construct, cells can be allowed to grow for 1-2 days in an enriched medium before they are switched to a selective medium. The purpose of the selectable marker is to confer resistance to selection, and its presence allows growth and recovery of cells that successfully express the introduced construct. Resistant clones of stably transformed cells can be proliferated using tissue culture techniques appropriate to the cell type. See, for example, *Animal Cell Culture*, R. I. Freshney, ed., 1986.

Any number of selection systems can be used to recover transformed cell lines. These include, but are not limited to, the herpes simplex virus thymidine kinase (Wigler et al., 1977. *Cell* vol. 11:223-32) and adenine phosphoribosyltransferase (Lowy et al., 1980 *Cell* vol. 22:817-23.) genes which can be employed in tk⁻ or apr⁻ (cells, respectively. Also, antimetabolite, antibiotic, or herbicide resistance can be used as the basis for selection. For example, dhfr confers resistance to methotrexate (Wigler et al., 1980. *Proc. Natl. Acad. Sci.* vol. 77:3567-70), npt confers resistance to the aminoglycosides, neomycin and G-418 (Colbere-Garapin et al., 1981. *J. Mol. Biol.* vol. 150: 1-14), and als and pat confer resistance to chlorsulfuron and phosphinotricin acetyltransferase, respectively. Additional selectable genes have been described. For example, trpB allows cells to utilize indole in place of tryptophan, and hisD allows cells to utilize histinol in place of histidine (Hartman & Mulligan, 1988. *Proc. Natl. Acad. Sci.* vol. 85:8047-51). Visible markers such as anthocyanins, β-glucuronidase and its substrate GUS, and luciferase and its substrate luciferin, can be used to identify transformants and to quantify the amount of transient or stable protein expression attributable to a specific construct system (Rhodes et al., 1995. *Methods Mol. Biol.* vol. 55:121-131).

Although the presence of marker gene expression suggests that a reporter gene is also present, its presence and expression may need to be confirmed. For example, if a sequence encoding a reporter gene is inserted within a marker gene sequence, transformed cells containing sequences that encode a reporter gene can be identified by the absence of marker gene function. Alternatively, a marker gene can be placed in tandem with a sequence encoding a reporter gene under the control of a single promoter. Expression of the marker gene in response to induction or selection usually indicates expression of a reporter gene.

Alternatively, host cells which contain a reporter gene and which express a reporter gene e can be identified by a variety of procedures known to those of skill in the art. These procedures include, but are not limited to, DNA-DNA or DNA-RNA hybridizations and protein bioassay or immunoassay techniques that include membrane, solution, or chip-based technologies for the detection and/or quantification of nucleic acid or protein. For example, the presence of a reporter gene can be detected by DNA-DNA or DNA-RNA hybridization or amplification using probes or fragments or fragments of polynucleotides encoding a reporter gene. Nucleic acid amplification-based assays involve the use of oligonucleotides selected from sequences encoding a reporter gene to detect transformants that contain a reporter gene.

Screening Methods of the Present Invention

Compound

The present invention includes methods for screening compounds capable of modulating gene expression. Any compound can be screened in an assay of the present invention.

In an embodiment, a compound includes a nucleic acid or a non-nucleic acid, such as a polypeptide or a non-peptide therapeutic agent. In a preferred embodiment, a nucleic acid can be a polynucleotide, a polynucleotide analog, a nucleotide, or a nucleotide analog. In a more preferred embodiment, a compound can be an antisense oligonucleotide, which are nucleotide sequences complementary to a specific DNA or RNA sequence of the present invention. Preferably, an antisense oligonucleotide is at least 11 nucleotides in length, but can be at least 12, 15, 20, 25, 30, 35, 40, 45, or 50 or more nucleotides long. Longer sequences also can be used. Antisense oligonucleotides can be deoxyribonucleotides, ribonucleotides, or a combination of both.

Nucleic acid molecules, including antisense oligonucleotide molecules, can be provided in a DNA construct and introduced into a cell. Nucleic acid molecules can be antisense or sense and double- or single-stranded. In a preferred embodiment, nucleic acid molecules can be interfering RNA (RNAi) or microRNA (miRNA). In a preferred embodiment, the dsRNA is 20-25 residues in length, termed small interfering RNAs (siRNA).

Oligonucleotides can be synthesized manually or by an automated synthesizer, by covalently linking the 5' end of one nucleotide with the 3' end of another nucleotide with non-phosphodiester internucleotide linkages such alkylphosphonates, phosphorothioates, phosphorodithioates, alkylphosphonothioates, alkylphosphonates, phosphoramidates, phosphate esters, carbamates, acetamidate, carboxymethyl esters, carbonates, and phosphate triesters. See Brown, 1994 *Meth. Mol. Biol.* vol. 20:1-8; Sonveaux, 1994. *Meth. Mol. Biol.* Vol. 26:1-72; and Uhlmann et al., 1990. *Chem. Rev.* vol. 90:543-583. Salts, esters, and other pharmaceutically acceptable forms of such compounds are also encompassed.

In a preferred embodiment, a compound can be a peptide, polypeptide, polypeptide analog, amino acid, or amino acid analog. Such a compound can be synthesized manually or by an automated synthesizer.

A compound can be a member of a library of compounds. In a specific embodiment, the compound is selected from a combinatorial library of compounds comprising peptoids; random biooligomers; diversomers such as hydantoins, benzodiazepines and dipeptides; vinylogous polypeptides; non-peptidal peptidomimetics; oligocarbamates; peptidyl phosphonates; peptide nucleic acid libraries; antibody libraries; carbohydrate libraries; and small organic molecule libraries. In a preferred embodiment, the small organic molecule libraries are libraries of benzodiazepines, isoprenoids, thiazolidinones, metathiazanones, pyrrolidines, morpholino compounds, or diazepindiones.

In another embodiment, a compound can have a molecular weight less than about 10,000 grams per mole, less than about 5,000 grams per mole, less than about 1,000 grams per mole, less than about 500 grams per mole, less than about 100 grams per mole, and salts, esters, and other pharmaceutically acceptable forms of such compounds.

Compounds can be evaluated comprehensively for cytotoxicity. The cytotoxic effects of the compounds can be studied using cell lines, including for example 293 (kidney), HuH7 (liver), and Hela cells over about 4, 10, 16, 24, 36 or 72-hour periods. In addition, a number of primary cells such as normal fibroblasts and peripheral blood mononuclear cells (PBMCs) can be grown in the presence of compounds at various concentrations for about 4 days. Fresh compound can be added every other day to maintain a constant level of exposure with time. The effect of each compound on cell-proliferation can be determined by CellTiter 96® AQueous One Solution Cell Proliferation Assay (Promega Co, Madison, Wis.) and [$^3$H]-Thymidine incorporation. Treatment of some cells with some of the compounds may have cytostatic effects. A selective index (ratios of $CC_{50}$ in cytotoxicity assays to the $EC_{50}$ in ELISA or FACS or the reporter gene assays) for each compound can be calculated for all of the UTR-reporters and protein inhibition assays. Compounds exhibiting substantial selective indices can be of interest and can be analyzed further in the functional assays.

The structure of a compound can be determined by any well-known method such as mass spectroscopy, NMR, vibrational spectroscopy, or X-ray crystallography as part of a method of the present invention.

Compounds can be pharmacologic agents already known in the art or can be compounds previously unknown to have any pharmacological activity. The compounds can be naturally occurring or designed in the laboratory. They can be isolated from microorganisms, animals, or plants, and can be produced recombinantly, or synthesized by chemical methods known in the art. If desired, compounds can be obtained using any of the numerous combinatorial library methods known in the art, including but not limited to, biological libraries, spatially addressable parallel solid phase or solution phase libraries, synthetic library methods requiring deconvolution, the "one-bead one-compound" library method, and synthetic library methods using affinity chromatography selection. Methods for the synthesis of molecular libraries are well known in the art (see, for example, DeWitt et al., Proc. Natl. Acad. Sci. U.S.A. 90, 6909, 1993; Erb et al. Proc. Natl. Acad. Sci. U.S.A. 91, 11422, 1994; Zuckermann et al., J. Med. Chem. 37, 2678, 1994; Cho et al., Science 261, 1303, 1993; Carell et al., Angew. Chem. Int. Ed. Engl. 33, 2059, 1994; Carell et al., Angew. Chem. Int. Ed. Engl. 33, 2061; Gallop et al., J. Med. Chem. 37, 1233, 1994). Libraries of compounds can be presented in solution (see, e.g., Houghten, BioTechniques 13, 412-421, 1992), or on beads (Lam, Nature 354, 82-84, 1991), chips (Fodor, Nature 364, 555-556, 1993), bacteria or spores (Ladner, U.S. Pat. No. 5,223,409), plasmids (Cull et al., Proc. Natl. Acad. Sci. U.S.A. 89, 1865-1869, 1992), or phage (Scott & Smith, Science 249, 386-390, 1990; Devlin, Science 249, 404-406, 1990); Cwirla et al., Proc. Natl. Acad. Sci. 97, 6378-6382, 1990; Felici, J. Mol. Biol. 222, 301-310, 1991; and Ladner, U.S. Pat. No. 5,223,409).

Methods of the present invention for screening compounds can select for compounds capable of modulating gene expression, which are capable of directly binding to a ribonucleic acid molecule transcribed from a target gene. In a preferred embodiment, a compound identified in accordance with the methods of the present invention may be capable of binding to one or more trans-acting factors (such as, but not limited to, proteins) that modulate UTR-dependent expression of a target gene. In another preferred embodiment, a compound identified in accordance with the methods of invention may disrupt an interaction between the 5' UTR and the 3' UTR.

Compounds can be tested using in vitro assays (e.g., cell-free assays) or in vivo assays (e.g., cell-based assays) well known to one of skill in the art or as provided in the present invention. A compound that modulates expression of a target gene can be determined from the methods provided in the present invention. A UTR of the present invention includes UTRs capable of modulating gene expression in the presence, in the absence, or in the presence and absence of a compound. In a preferred embodiment, the effect of a compound on the expression of one or more genes can be determined utilizing assays well known to one of skill in the art or provided by the present invention to assess the specificity of a particular compound's effect on the UTR-dependent expression of a target gene. In a more preferred embodiment, a compound has specificity for a plurality of genes. In another more preferred embodiment, a compound identified utilizing the methods of the present invention is capable of specifically effect the expression of only one gene or, alternatively, a group of genes within the same signaling pathway. Compounds identified in the assays of the present invention can be tested for biological activity using host cells containing or engineered to contain the target RNA element involved in UTR-dependent gene expression coupled to a functional readout system.

Screening Assays

The present invention includes and provides for assays capable of screening for compounds capable of modulating gene expression. In a preferred aspect of the present invention, an assay is an in vitro assay. In another aspect of the present invention, an assay is an in vivo assay. In another preferred aspect of the present invention, an assay measures translation. In a preferred aspect of the present invention, the assay includes a nucleic acid molecule of the present invention or a construct of the present invention. A nucleic acid molecule or construct of the present invention include, without limitation, SEQ ID NOs: 3-12, or a sequence that differs from any of the residues in SEQ ID NOs: 3-12 in that the nucleic acid sequence has been deleted, substituted, or added in a manner that does not alter the function. The present invention also provides fragments and complements of all the nucleic acid molecules of the present invention.

In one embodiment of the present invention, the activity or expression of a reporter gene is modulated. Modulated means increased or decreased during any point before, after, or during translation. In a preferred embodiment, activity or expression of a reporter gene is modulated during translation. For example, inhibition of translation of the reporter gene would modulate expression. In an alternative example, expression level of a reporter gene is modulated if the steady-state level of the expressed protein decreased even though translation was not inhibited. For example, a change in the half-life of a mRNA can modulate expression.

In an alternative embodiment, modulated activity or expression of a reporter gene means increased or decreased during any point before or during translation.

In a more preferred aspect, the activity or expression of a reporter gene or a target gene is modulated by greater than 30%, 40%, 50%, 60%, 70%, 80% or 90% in the presence of a compound. In a highly preferred aspect, more of an effect is observed in VEGF-dependent cancer cells.

In a most preferred aspect, the activity or expression of a reporter gene is modulated without altering the activity of a control gene for general, indiscriminate translation activity. As used herein, indiscriminate translation activity refers to modulation in translation levels or activity that is random or unsystematic. One assay for modulation in general, indiscriminate translation activity uses a general translational inhibitor, for example puromycin, which is an inhibitor that causes release of nascent peptide and mRNA from ribosomes.

Expression of a reporter gene can be detected with, for example, techniques know in the art. Translation or transcription of a reporter gene can be detected in vitro or in vivo. In detection assays, either the compound or the reporter gene can comprise a detectable label, such as a fluorescent, radioisotopic, chemiluminescent, or enzymatic label, such as horseradish peroxidase, alkaline phosphatase, or luciferase.

High-throughput screening can be done by exposing nucleic acid molecules of the present invention to a library of compounds and detecting gene expression with assays known in the art, including, for example without limitation, those described above. In one embodiment of the present invention, cancer cells, such as HeLa cells, expressing a nucleic acid molecule of the present invention are treated with a library of compounds. Percent inhibition of reporter gene activity can be obtained with all the library compounds can be analyzed using, for example without limitation, a scattergram generated by SpotFire® (SpotFire, Inc., Somerville, Mass.). The high-throughput screen can be followed by subsequent selectivity screens. In a preferred embodiment, a subsequent selectivity screen can include detection of reporter gene expression in cells expressing, for example, a reporter gene linked to a PTCRE or flanked by a 5' and 3' UTR of the same gene, either of which contains a PTCRE or a NeRP or both of the present invention. In an alternative preferred embodiment, a subsequent selectivity screen can include detection of reporter gene expression in cells in the presence of a various concentrations of compounds.

Once a compound has been identified to modulate UTR-dependent expression of a target gene and preferably, the structure of the compound has been identified by the methods described in the present invention and well known in the art, the compounds are tested for biological activity in further assays and/or animal models. Further, a lead compound may be used to design congeners or analogs.

A wide variety of labels and conjugation techniques are known by those skilled in the art and can be used in various nucleic acid and amino acid assays. Means for producing labeled hybridization or PCR probes for detecting sequences related to PTCREs or NeRPs of the present invention include oligolabeling, nick translation, end-labeling, or PCR amplification using a labeled nucleotide. Suitable reporter molecules or labels which can be used for ease of detection include radionuclides, enzymes, and fluorescent, chemiluminescent, or chromogenic agents, as well as substrates, cofactors, inhibitors, magnetic particles, and the like.

In Vitro

The present invention includes and provides for assays capable of screening for compounds capable of modulating gene expression. In a preferred aspect of the present invention, an assay is an in vitro assay. In a preferred aspect of the present invention, an in vitro assay that measures translation. In a preferred aspect of the present invention the in vitro assay includes a nucleic acid molecule of the present invention or a construct of the present invention.

In one embodiment, a reporter gene of the present invention can encode a fusion protein or a fusion protein comprising a domain that allows the expressed reporter gene to be bound to a solid support. For example, glutathione-S-transferase fusion proteins can be adsorbed onto glutathione sepharose beads (Sigma Chemical, St. Louis, Mo.) or glutathione derivatized microtiter plates, which are then combined with the compound or the compound and the non-adsorbed expressed reporter gene; the mixture is then incubated under conditions conducive to complex formation (e.g., at physiological conditions for salt and pH). Following incubation, the beads or microtiter plate wells are washed to remove any unbound components. Binding of the interactants can be determined either directly or indirectly, as described above. Alternatively, the complexes can be dissociated from the solid support before binding is determined.

Other techniques for immobilizing an expressed reporter gene or compound on a solid support also can be used in the screening assays of the invention. For example, either an expressed reporter gene or compound can be immobilized utilizing conjugation of biotin and streptavidin. Biotinylated expressed reporter genes or compounds can be prepared from biotin-NHS(N-hydroxysuccinimide) using techniques well known in the art (e.g., biotinylation kit, Pierce Chemicals, Rockford, Ill.) and immobilized in the wells of streptavidin-coated 96 well plates (Pierce Chemicals, Rockford, Ill.). Alternatively, antibodies which specifically bind to an expressed reporter gene or compound, but which do not interfere with a desired binding or catalytic site, can be derivatized to the wells of the plate. Unbound target or protein can be trapped in the wells by antibody conjugation.

Methods for detecting such complexes, in addition to those described above for the GST-immobilized complexes, include immunodetection of complexes using antibodies which specifically bind to an expressed reporter gene or compound, enzyme-linked assays which rely on detecting an activity of an expressed reporter gene, electrophoretic mobility shift assays (EMSA), and SDS gel electrophoresis under reducing or non-reducing conditions.

In one embodiment, translation of a reporter gene in vitro can be detected following the use of a reticulocyte lysate translation system, for example the TNT® Coupled Reticulocyte Lysate System (Promega Co., Madison, Wis.). In this aspect, for example, without limitation, RNA (100 ng) can be translated at 30° C. in reaction mixtures containing 70% reticulocyte lysate, 20 μM amino acids and RNase inhibitor (0.8 units/μl). After 45 minutes of incubation, 20 μl of Luclite can be added and luminescence can be read on the View-Lux. Different concentrations of compounds can be added to the reaction in a final DMSO concentration of 2% and the $EC_{50}$ values calculated. Puromycin can be used as control for general indiscriminate translation inhibition. In vitro transcripts encoding a reporter gene linked to specific UTRs from target genes, including GAPDH, XIAP, TNF-α, and HIF-1α, can also be used.

To study the influence of cell-type specific factors, capped RNA can be translated in translation extracts prepared from specialized cells or cancer cell lines, for example without limitation, HT1080 cells (a human fibrosarcoma cell line). Briefly, the cells can be washed with PBS and swollen in hypotonic buffer (10 mM Hepes, pH 7.4, 15 mM KCl, 1.5 mM $Mg(OAc)_2$, 2 mM DTT and 0.5 mM Pefabloc (Pentapharm Ltd. Co., Switzerland) for 5 minutes on ice. The cells can be lysed using a Dounce homogenizer (100 strokes), and the extracts can be spun for 10 minutes at 10,000×g. These clarified extracts can then be flash-frozen in liquid nitrogen and stored in aliquots at −70° C. The translation reaction can be capped RNA (50 ng) in a reaction mixture containing 60% clarified translation extract, 15 μM total amino acids, 0.2 mg/ml Creatine phosho-kinase, which are all in 1× translation buffer (15 mM Hepes, pH 7.4, 85 mM KOAc, 1.5 mM $Mg(OAc)_2$, 0.5 mM ATP, 0.075 mM GTP, 18 mM creatine diphosphate and 1.5 mM DTT). After incubation of the translation reaction for 90 min at 37° C., activity of the protein encoded by the reporter gene can be detected. For activity of luciferase, encoded by the luciferase gene serving as the reporter gene, addition of 20 μl of LucLite® (Packard Instrument Co., Inc., Meriden, Conn.) can be used.

Capped and uncapped RNAs can be synthesized in vitro using the T7 polymerase transcription kits (Ambion Inc., Austin, Tex.). Capped RNAs from a variety of nucleic acid molecules of the present invention, including without limitation, constructs with VEGF linked to a PTCRE of the present invention, constructs with a reporter gene linked only to a vector, constructs with GAPDH linked to a PTCRE, constructs with a HIF-1α linked to a PTCRE, and constructs with a HIF-1α not linked to a PTCRE, can be used in a similar in vitro system to study the influence of cell-type specific factors on translation.

In Vivo

The present invention includes and provides for assays capable of screening for compounds capable of modulating gene expression. In a preferred aspect of the present invention, an assay is an in vivo assay. A preferred aspect of the present invention is an assay that measures translation. In a preferred embodiment of the present invention, an in vivo assay includes a nucleic acid molecule of the present invention or a construct of the present invention and can include the use of a cell or a cell or tissue within an organism. In a more preferred embodiment, an in vivo assay includes a nucleic acid molecule of the present invention present in a cell or a cell or tissue within an organism.

In another embodiment, in vivo translation of a reporter gene can be detected. In a preferred embodiment, a reporter gene is transfected into a cancer cell obtained from a cell line available at the (American Type Culture Collection (ATCC), Manassas, Va.), for example HeLa, MCF-7, and COS-7, BT474. In a more preferred embodiment, a cancer cell has an altered genome relative to a similarly derived normal, primary cell, and the mammalian cancer cell proliferates under conditions where such a primary cell would not.

Screening for compounds that modulate reporter gene expression can be carried out in an intact cell. Any cell that comprises a reporter gene can be used in a cell-based assay system. A reporter gene can be naturally occurring in the cell or can be introduced using techniques such as those described above (see Cells and Organisms). In one embodiment, a cell line is chosen based on its expression levels of naturally occurring VEGF. Modulation of reporter gene expression by a compound can be determined in vitro as described above or in vivo as described below.

To detect expression of endogenous protein, a variety of protocols for detecting and measuring the expression of a reporter gene are known in the art. For example, Enzyme-Linked Immunosorbent Assays (ELISAs), western blots using either polyclonal or monoclonal antibodies specific for an expressed reporter gene, Fluorescence-Activated Cell Sorter (FACS), electrophoretic mobility shift assays (EMSA), or radioimmunoassay (RIA) can be performed to quantify the level of specific proteins in lysates or media derived from cells treated with the compounds. In a preferred embodiment, a phenotypic or physiological readout can be used to assess UTR-dependent activity of the target RNA in the presence and absence of the lead compound.

A wide variety of labels and conjugation techniques are known by those skilled in the art and can be used in various nucleic acid and amino acid assays. Means for producing labeled hybridization or PCR probes for detecting sequences related to polynucleotides having a PTCRE or a NeRP of the present invention include oligolabeling, nick translation, end-labeling, or PCR amplification using a labeled nucleotide. Alternatively, sequences having a PTCRE or a NeRP of the present invention can be cloned into a vector for the production of a mRNA probe. Such vectors are known in the art, are commercially available, and can be used to synthesize RNA probes in vitro by addition of labeled nucleotides and an appropriate RNA polymerase such as T7, T3, or SP6. These procedures can be conducted using a variety of commercially available kits (Amersham Biosciences Inc., Piscataway, N.J.; and Promega Co, Madison, Wis.). Suitable reporter molecules or labels which can be used for ease of detection include radionucleotides, enzymes, and fluorescent, chemiluminescent, or chromogenic agents, as well as substrates, cofactors, inhibitors, magnetic particles, and the like.

Therapeutic Uses

The present invention also provides for methods for treating, preventing or ameliorating one or more symptoms of a disease or disorder associated with the aberrant expression of a target gene, said method comprising administering to a subject in need thereof a therapeutically or prophylactically effective amount of a compound, or a pharmaceutically acceptable salt thereof, identified according to the methods described herein. In one embodiment of the present invention, a target gene is aberrantly expressed. A target gene can be aberrantly overexpressed or expressed at an aberrantly low level. In particular, the invention provides for a method of treating or preventing a disease or disorder or ameliorating a symptom thereof, said method comprising administering to a subject in need thereof an effective amount of a compound, or a pharmaceutically acceptable salt thereof, identified according to the methods described herein, wherein said effective amount increases the expression of a target gene beneficial in the treatment or prevention of said disease or disorder. The invention also provides for a method of treating or preventing a disease or disorder or ameliorating a symptom thereof, said method comprising administering to a subject in need thereof an effective amount of a compound, or a pharmaceutically acceptable salt thereof, identified according to the methods described herein, wherein said effective amount decreases the expression of a target gene whose expression is associated with or has been linked to the onset, development, progression or severity of said disease or disorder. In a specific embodiment, the disease or disorder is a proliferative disorder, an inflammatory disorder, an infectious disease, a genetic disorder, an autoimmune disorder, a cardiovascular disease, or a central nervous system disorder. In an embodiment wherein the disease or disorder is an infectious disease, the infectious disease can be caused by a fungal infection, a bacterial infection, a viral infection, or an infection caused by another type of pathogen.

In addition, the invention provides pharmaceutical compositions that can be administered to a patient to achieve a therapeutic effect. Pharmaceutical compositions of the invention can comprise, for example, ribozymes or antisense oligonucleotides, antibodies that specifically bind to a PTCRE or NeRP of the present invention, or mimetics, activators, inhibitors of PTCRE or NeRP activity, or a nucleic acid molecule of the present invention. The compositions can be administered alone or in combination with at least one other agent, such as stabilizing compound, which can be administered in any sterile, biocompatible pharmaceutical carrier, including, but not limited to, saline, buffered saline, dextrose, and water. The compositions can be administered to a patient alone, or in combination with other agents, drugs or hormones.

In addition to the active ingredients, these pharmaceutical compositions can contain suitable pharmaceutically-acceptable carriers comprising excipients and auxiliaries which facilitate processing of the active compounds into preparations which can be used pharmaceutically. Pharmaceutical compositions of the invention can be administered by any number of routes including, but not limited to, oral, intravenous, intramuscular, intra-arterial, intramedullary, intrathecal, intraventricular, transdermal, subcutaneous, intraperitoneal, intranasal, parenteral, topical, sublingual, or rectal means. Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers, such as sugars, including lactose, sucrose, mannitol, or sorbitol; starch from corn, wheat, rice, potato, or other plants; cellulose, such as methyl cellulose, hydroxypropylmethyl-cellulose, or sodium carboxymethylcellulose; gums including arabic and tragacanth; and proteins such as gelatin and collagen. If desired, disintegrating or solubilizing agents can be added, such as the cross-linked polyvinyl pyrrolidone, agar, alginic acid, or a salt thereof, such as sodium alginate.

Pharmaceutical preparations that can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds can be dissolved or suspended in suitable liquids, such as fatty oils, liquid, or liquid polyethylene glycol with or without stabilizers.

Pharmaceutical formulations suitable for parenteral administration can be formulated in aqueous solutions, preferably in physiologically compatible buffers such as Hanks' solution, Ringer's solution, or physiologically buffered saline. Aqueous injection suspensions can contain substances that increase the viscosity of the suspension, such as sodium carboxymethyl cellulose, sorbitol, or dextran. Additionally, suspensions of the active compounds can be prepared as appropriate oily injection suspensions. Suitable lipophilic solvents or vehicles include fatty oils such as sesame oil, or synthetic fatty acid esters, such as ethyl oleate or triglycerides, or liposomes. Non-lipid polycationic amino polymers also can be used for delivery. Optionally, the suspension also can contain suitable stabilizers or agents that increase the solubility of the compounds to allow for the preparation of highly concentrated solutions. For topical or nasal administration, penetrants appropriate to the particular barrier to be permeated are used in the formulation. Such penetrants are generally known in the art.

The pharmaceutical compositions of the present invention can be manufactured in a manner that is known in the art, e.g., by means of conventional mixing, dissolving, granulating, dragee-making, levigating, emulsifying, encapsulating, entrapping, or lyophilizing processes. The pharmaceutical composition can be provided as a salt and can be formed with many acids, including but not limited to, hydrochloric, sulfuric, acetic, lactic, tartaric, malic, succinic, etc. Salts tend to be more soluble in aqueous or other protonic solvents than are the corresponding free base forms. In other cases, the preferred preparation can be a lyophilized powder which can contain any or all of the following: 1-50 mM histidine, 0.1%-2% sucrose, and 2-7% mannitol, at a pH range of 4.5 to 5.5, that is combined with buffer prior to use. Further details on techniques for formulation and administration can be found in the latest edition of *Remington's Pharmaceutical Sciences* (Maack Publishing Co., Easton, Pa.). After pharmaceutical compositions have been prepared, they can be placed in an appropriate container and labeled for treatment of an indicated condition. Such labeling would include amount, frequency, and method of administration.

Determination of a Therapeutically Effective Dose

A therapeutically effective dose refers to that amount of active ingredient that increases or decreases reporter gene activity relative to reporter gene activity that occurs in the absence of the therapeutically effective dose. For any compound, the therapeutically effective dose can be estimated initially either in cell culture assays or in animal models, usually mice, rabbits, dog, or pigs. The animal model also can be used to determine the appropriate concentration range and route of administration. Such information can then be used to determine useful doses and routes for administration in humans.

Therapeutic efficacy and toxicity, e.g., $ED_{50}$ (the dose therapeutically effective in 50% of the population) and $LD_{50}$ (the dose lethal to 50% of the population), can be determined by standard pharmaceutical procedures in cell cultures or experimental animals. The dose ratio of toxic to therapeutic effects is the therapeutic index, and it can be expressed as the ratio, $LD_{50}/ED_{50}$.

Pharmaceutical compositions that exhibit large therapeutic indices are preferred. The data obtained from cell culture assays and animal studies is used in formulating a range of dosage for human use. The dosage contained in such compositions is preferably within a range of circulating concentrations that include the $ED_{50}$ with little or no toxicity. The dosage varies within this range depending upon the dosage form employed, sensitivity of the patient, and the route of administration.

The exact dosage will be determined by the practitioner, in light of factors related to the subject that requires treatment. Dosage and administration are adjusted to provide sufficient levels of the active ingredient or to maintain the desired effect. Factors that can be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions can be administered every 3 to 4 days, every week, or once every two weeks depending on the half-life and clearance rate of the particular formulation.

Normal dosage amounts can vary from 0.1 to 100,000 micrograms, up to a total dose of about 1 g, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

If the reagent is a single-chain antibody, polynucleotides encoding the antibody can be constructed and introduced into a cell either ex vivo or in vivo using well-established techniques including, but not limited to, transferrin-polycation-mediated DNA transfer, transfection with naked or encapsulated nucleic acids, liposome-mediated cellular fusion, intracellular transportation of DNA-coated latex beads, protoplast fusion, viral infection, electroporation, "gene gun," and DEAE- or calcium phosphate-mediated transfection.

Effective in vivo dosages of an antibody are in the range of about 5 µg to about 50 µg/kg, about 50 µg to about 5 mg/kg, about 100 µg to about 500 µg/kg of patient body weight, and about 200 to about 250 µg/kg of patient body weight. For administration of polynucleotides encoding single-chain antibodies, effective in vivo dosages are in the range of about 100 ng to about 200 ng, 500 ng to about 50 mg, about 1 µg to about 2 mg, about 5 µg to about 500 µg, and about 20 µg to about 100 µg of DNA.

If the expression product is mRNA, the reagent is preferably an antisense oligonucleotide or a ribozyme. Polynucleotides that express antisense oligonucleotides or ribozymes can be introduced into cells by a variety of methods, as described above.

Preferably, a reagent reduces expression of a reporter gene or the activity of a reporter gene by at least about 10, preferably about 50, more preferably about 75, 90, or 100% relative to the absence of the reagent. The effectiveness of the mechanism chosen to decrease the level of expression of a reporter gene or the activity of a reporter gene can be assessed using methods well known in the art, such as hybridization of nucleotide probes to reporter gene-specific mRNA, quantitative RT-PCR, immunologic detection of an expressed reporter gene, or measurement of activity from an expressed reporter gene.

In any of the embodiments described above, any of the pharmaceutical compositions of the invention can be administered in combination with other appropriate therapeutic agents. Selection of the appropriate agents for use in combination therapy can be made by one of ordinary skill in the art, according to conventional pharmaceutical principles. The combination of therapeutic agents can act synergistically to effect the treatment or prevention of the various disorders described above. Using this approach, one may be able to achieve therapeutic efficacy with lower dosages of each agent, thus reducing the potential for adverse side effects.

Any of the therapeutic methods described above can be applied to any subject in need of such therapy, including, for example, mammals such as dogs, cats, cows, horses, rabbits, monkeys, and most preferably, humans.

Administration of a Therapeutically Effective Dose

A reagent which affects translation can be administered to a human cell, either in vitro or in vivo, to specifically reduce translational activity of a specific gene. In a preferred embodiment, the reagent preferably binds to a 5' UTR of a gene. In an alternate embodiment, the present invention the reagent preferably binds to a PTCRE or NeRP of the present invention. In a preferred embodiment, the reagent is a compound. For treatment of human cells ex vivo, an antibody can be added to a preparation of stem cells which have been removed from the body. The cells can then be replaced in the same or another human body, with or without clonal propagation, as is known in the art.

In one embodiment, the reagent is delivered using a liposome. Preferably, the liposome is stable in the animal into which it has been administered for at least about 30 minutes, more preferably for at least about 1 hour, and even more preferably for at least about 24 hours. A liposome comprises a lipid composition that is capable of targeting a reagent, particularly a polynucleotide, to a particular site in an animal, such as a human. Preferably, the lipid composition of the liposome is capable of targeting to a specific organ of an animal, such as the lung, liver, spleen, heart brain, lymph nodes, and skin.

A liposome useful in the present invention comprises a lipid composition that is capable of fusing with the plasma membrane of the targeted cell to deliver its contents to the cell. Preferably, the transfection efficiency of a liposome is about 0.5 µg of DNA per 16 nmole of liposome delivered to about $10^6$ cells, more preferably about 1.0 µg of DNA per 16 nmole of liposome delivered to about $10^6$ cells, and even more preferably about 2.0 µg of DNA per 16 nmol of liposome delivered to about $10^6$ cells. Preferably, a liposome is between about 100 and 500 nm, more preferably between about 150 and 450 nm, and even more preferably between about 200 and 400 nm in diameter.

Suitable liposomes for use in the present invention include those liposomes standardly used in, for example, gene delivery methods known to those of skill in the art. More preferred liposomes include liposomes having a polycationic lipid composition and/or liposomes having a cholesterol backbone conjugated to polyethylene glycol. Optionally, a liposome comprises a compound capable of targeting the liposome to a particular cell type, such as a cell-specific ligand exposed on the outer surface of the liposome.

Complexing a liposome with a reagent such as an antisense oligonucleotide or ribozyme can be achieved using methods that are standard in the art (see, for example, U.S. Pat. No. 5,705,151). Preferably, from about 0.1 µg to about 10 µg of polynucleotide is combined with about 8 nmol of liposomes, more preferably from about 0.5 µg to about 5 µg of polynucleotides are combined with about 8 nmol liposomes, and even more preferably about 1.0 µg of polynucleotides is combined with about 8 nmol liposomes.

In another embodiment, antibodies can be delivered to specific tissues in vivo using receptor-mediated targeted delivery. Receptor-mediated DNA delivery techniques are taught in, for example, Findeis et al. Trends in Biotechnol. 11, 202-05 (1993); Chiou et al., *Gene Therapeutics: Methods And Applications Of Direct Gene Transfer* (J. A. Wolff, ed.) (1994); Wu & Wu, J. Biol. Chem. 263, 621-24 (1988); Wu et al., J. Biol. Chem. 269, 542-46 (1994); Zenke et al., Proc. Natl. Acad. Sci. U.S.A. 87, 3655-59 (1990); Wu et al., J. Biol. Chem. 266, 338-42 (1991).

Diagnostic Methods

Agents of the present invention can also be used in diagnostic assays for detecting diseases and abnormalities or susceptibility to diseases and abnormalities related to the presence of mutations in the nucleic acid sequences that encode a PTCRE or NeRP of the present invention. For example, differences can be determined between the cDNA or genomic sequence encoding a PTCRE or NeRP in individuals afflicted with a disease and in normal individuals. If a mutation is observed in some or all of the afflicted individuals but not in normal individuals, then the mutation is likely to be the causative agent of the disease.

For example, the direct DNA sequencing method can reveal sequence differences between a reference gene and a gene having mutations. In addition, cloned DNA segments can be employed as probes to detect specific DNA segments. The sensitivity of this method is greatly enhanced when combined with PCR. For example, a sequencing primer can be used with a double-stranded PCR product or a single-stranded template molecule generated by a modified PCR. The sequence determination is performed by conventional procedures using radiolabeled nucleotides or by automatic sequencing procedures using fluorescent tags.

Moreover, for example, genetic testing based on DNA sequence differences can be carried out by detection of alteration in electrophoretic mobility of DNA fragments in gels with or without denaturing agents. Small sequence deletions and insertions can be visualized, for example, by high-resolution gel electrophoresis. DNA fragments of different sequences can be distinguished on denaturing formamide gradient gels in which the mobilities of different DNA fragments are retarded in the gel at different positions according to their specific melting or partial melting temperatures (see, e.g., Myers et al., Science 230, 1242, 1985). Sequence changes at specific locations can also be revealed by nuclease protection assays, such as RNase and S1 protection or the chemical cleavage method (e.g., Cotton et al., Proc. Natl. Acad. Sci. USA 85, 4397-4401, 1985). Thus, the detection of a specific DNA sequence can be performed by methods such as hybridization, RNase protection, chemical cleavage, direct DNA sequencing or the use of restriction enzymes and Southern blotting of genomic DNA. In addition to direct methods such as gel-electrophoresis and DNA sequencing, mutations can also be detected by in situ analysis.

Altered levels of a PTCRE or NeRP of the present invention can also be detected in various tissues. For example, one or more genes having a PTCRE or a NeRP can be detected by assays used to detect levels of particular nucleic acid sequence, such as Southern hybridization, northern hybridization, and PCR. Alternatively, assays can be used to detect levels of a reporter polypeptide regulated by a PTCRE or a NeRP or of a polypeptide encoded by a gene having a PTCRE or a NeRP. Such assays are well known to those of skill in the art and include radioimmunoassays, competitive binding assays, western blot analysis, and ELISA assays. A sample from a subject, such as blood or a tissue biopsy derived from a host, may be the material on which these assays are conducted.

Having now generally described the invention, the same will be more readily understood through reference to the following examples that are provided by way of illustration, and are not intended to be limiting of the present invention, unless specified.

Each periodical, patent, and other document or reference cited herein is herein incorporated by reference in its entirety.

EXAMPLES

Example 1

Identification of Compounds that Specifically Inhibit VEGF Expression Post-Transcriptionally A monocistronic reporter construct (pLuc/vegf5'+3'UTR) is under the transcriptional control of the CMV promoter and contains a VEGF IRES driving the luciferase reporter, which nucleic acid sequences are both upstream of a VEGF 3'-UTR. Stable cell lines are generated by transfecting 293 cells with the pLuc/vegf5'+3'UTR. A stable cell line is cultured under hygromycin B selection to create clonal cell lines consistent with protocols well known in the art. After two weeks of selection, clonal cell lines are screened for luciferase activity. The luciferase activity of several clonal cell lines (hereafter "clones") are compared and normalized against total protein content. Clones are maintained under hygromycin B selection for more than three months with intermittent monitoring of luciferase activity. Clones are stable and maintain a high level of luciferase expression. Many clones, for example, about twenty, may be compared to each other with respect to luciferase activity. In comparison to clones B9, D3, and H6, clone B9 exhibits the highest level of luciferase activity. In addition, semi-quantitative PCR analysis is performed, and the results indicate that multiple copies of the reporter are integrated per cell. Particular parameters for clones are studied prior to selection for use in post-transcriptional, high-throughput screening (PTHTS). Relevant parameters for PTHTS include, but are not limited to, cell number, incubation time, DMSO concentration, and volume of substrate.

Chemical libraries in excess of 150,000 compounds are screened by PTHTS with a clone containing the monocistronic reporter construct, pLuc/vegf5'+3'UTR. Screens are performed in duplicate with each molecule at a single concentration of 7.5 µM. Bright-Glow (Promega Co., Madison, Wis.) is used as a substrate to measure firefly luciferase activity. Active compounds are identified by reporting the average percent inhibition of the duplicate runs followed by rejecting those compounds that did not provide satisfactory reproducibility. The average percent inhibition of compounds that provide satisfactory reproducibility is within a range of about 10%, about 25% or about 35% in duplicate runs. Data is analyzed as a normal distribution, which is apparent from graphical and statistical analysis of skewness and kurtosis. Hits are then reported at about a 99% confidence level, usually representing a selection of 3 standard deviations from the mean, or a hit lower limit of observed inhibition about equal to 50%. These selection criteria result in a hit rate of about 1%.

Certain compounds that are identified through the PTHTS-screening tier by screening with clone B9 modulate hypoxia-inducible endogenous VEGF expression. Endogenous VEGF protein levels are monitored by an ELISA assay (R&D Systems, Minneapolis, Minn.). HeLa cells are used to evaluate hypoxia-inducible expression. HeLa cells demonstrate about a three- to five-fold hypoxia-inducible window as compared to normoxic conditions (about 1000-about 1500 pg/ml under hypoxia compared to about 200-about 400 pg/ml under normoxia). Cells are cultured overnight under hypoxic conditions (about 1% $O_2$, about 5% $CO_2$, and balanced with nitrogen) in the presence or absence of compounds. The conditioned media is assayed by ELISA. The concentration of VEGF is calculated from the standard ELISA curve of each assay. The assays are performed in duplicate at a compound concentration of about 7 µM. A threshold of about 50% inhibition for a compound is selected as a criterion for further investigation. Further evaluation of about 100 to about 150 compounds is conducted from about 700 to about 800 initial PTHTS hits. The activity of the identified compounds is confirmed by repeating the experiments described above. The identified compounds are then acquired as dry powders and analyzed further. The purity and molecular weight of the identified compounds are confirmed by LC-MS.

A dose-response analysis is performed using an ELISA assay and using conditions essentially as described above. A series of seven different concentrations are analyzed. In parallel, a dose-response cytotoxicity assay is performed under the same conditions as the ELISA to ensure that the inhibition of VEGF expression is not due to cytotoxicity as measured by CellTiter-Glo® (Promega, Inc., Madison, Wis.). Dose-response curves are plotted using percentage inhibition versus concentration of the compound.

For each compound, the maximal inhibition is set as 100% and the minimal inhibition is set as 0% to generate $EC_{50}$ and $CC_{50}$ values. A compound from PTHTS shows a sigmoidal curve over a compound concentration range from about $10^{-1}$ nM to about $10^4$ nM when plotted against the percent inhibition of VEGF expression on the y-axis (see FIG. 2). The same compound from PTHTS shows a convex curve over the same compound concentration range plotted against the percent of cytotoxicity. The ELISA $EC_{50}$ (50% inhibition of VEGF expression) for this particular compound is about 7 nM, while its $CC_{50}$ (50% cytotoxicity) is greater than about 2000 nM. Subsets of compounds that show similar efficacy/cytotoxicity windows are also identified.

Figure 3:
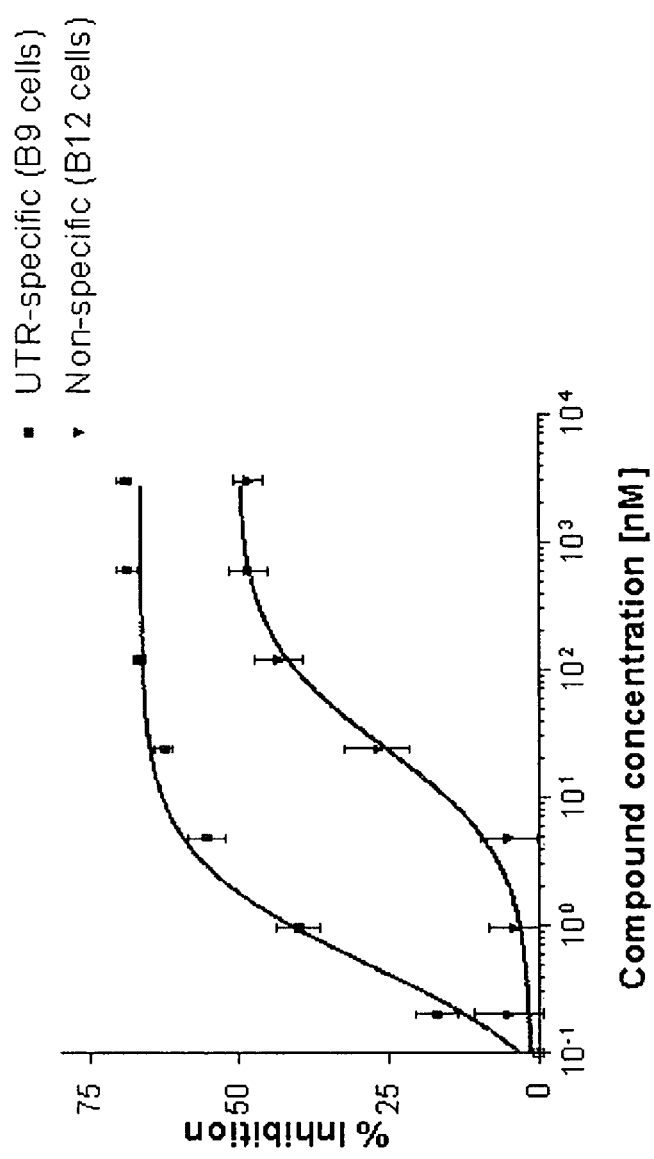
FIG. 3 sets forth an example of UTR-dependent inhibition of VEGF expression, where VEGF expression is dependent on one or more VEGF UTRs.

The B9 cell line harbors the firefly luciferase reporter driven by the CMV promoter and flanked by the 5'- and 3'-UTRs of VEGF transcripts. Use of the B9 cell line with the PTHTS identifies compounds that specifically target the function of VEGF UTRs to modulate expression. Cell line B12 harbors the luciferase reporter in the absence of operably linked VEGF UTRs. Compounds that inhibit luciferase activity in both the B9 and B12 cell lines are general transcription or general translation inhibitors or luciferase enzyme inhibitors. Several UTR specific compounds are identified in experiments with PTHTS identified compounds as described above. The dose-response curves of an identified compound show a concave curve in B9 cells and a sigmoidal curve in B12 cells when the percent luciferase inhibition of each is plotted over a compound concentration range from about $10^{-1}$ nM to about $10^4$ nM on the x-axis (see FIG. 3). The difference between the two cell lines (B9 and B12) shows that inhibition of VEGF production by this compound is through the VEGF UTRs, i.e., by a post-transcriptional control mechanism. A control experiment is performed with a general translation inhibitor, puromycin. Puromycin treatment does not change the difference of inhibition in luciferase expression in these two cell lines.

Example 2

Characteristics of UTR-Specific VEGF Inhibitors

All identified compounds are re-synthesized and shown by LC/MS and combustion analysis to be greater than 95% pure. Subsequently, the re-synthesized compounds are tested in the dose-response VEGF ELISA and luciferase assays that are used to initially assess UTR specificity. All identified compounds retain UTR specificity and are bonafide inhibitors of VEGF expression.

PTHTS using B9 cells identified compounds that specifically inhibit hypoxia inducible VEGF expression for the treatment of ocular neovascular diseases. Compounds that target multiple angiogenesis factors (including VEGF) for the treatment of cancers are also identifiable. Several targets are used for these purposes, including TNF-α, FGF-2, G-CSF, IGF-1, PDGF, and HIF-1α.

ELISA assays analyze levels of expression of these factors using commercially available kits from R&D Systems (Minneapolis, Minn.). UTR-specific PTHTS identified compounds are tested for their ability to inhibit the expression of a subset of these proteins, including G-CSF, TNFα, FGF-2, and IGF-1. Identified compounds that are very potent inhibitors of VEGF production as assayed in HeLa cells have $EC_{50}$ values ranging from low nM to high nM. Treatment with a general translation inhibitor (puromycin) results in similar inhibition for all these cytokines, with $EC_{50}$ values ranging from about 0.2 to about 2 µM.

Lead compounds are further characterized and optimized. Analogs are synthesized and identified compounds exhibit excellent potency in the VEGF ELISA assay ($EC_{50}$ values ranging from 0.5 nM to 50 nM). In another embodiment, an analog exhibits low nM potency. In an additional embodiment, several analogs are synthesized and a subset of identified compounds are very active ($EC_{50}$ values ranging from 1 to 50 nM) in the VEGF ELISA assay. Activity of a very potent analog is improved about 500-fold compared to its parent ($EC_{50}$ of 1 nM vs. 500 nM). Further characterization and optimization for selectivity and pharmaceutical properties (ADMET) of the most active compounds will develop a drug candidate(s) for clinical trials.

Example 3

Identified Compounds are Active as Inhibitors of Hypoxia-Inducible VEGF Production in Retinal Pigment Epithelial Cells and Macrophage Cells PTHTS identified compounds are VEGF-specific inhibitors for the treatment of ocular neovascular disorders. The effect of the identified compounds on retinal pigment epithelial cells and macrophage cells are tested in two cell lines: ARPE-19, a human retinal pigment epithelial cell line, and RAW264, a mouse macrophage cell line. Both cell lines produce high levels of VEGF under hypoxic conditions. A subset of identified compounds is active in these two cell lines. Compound 1 inhibits VEGF production in both macrophage (a non-limiting example of which is RAW264.7) and retinal pigment epithelial cells (a non-limiting example of which is ARPE-19). In selectivity studies, as shown in Table 2, Compound 1 specifically inhibits VEGF expression relative to that of other factors (FGF-2, IGF-1, GCSF, TNFα).

TABLE 2

Selectivity studies

| | | Compound 1 | Compound 2 | Compound 3 |
|---|---|---|---|---|
| ELISA ($EC_{50\,g}$ μM) | VEGF | 0.007–0.02 | 0.1–0.5 | 0.2–1 |
| | TNFα | >30 | >30 | >30 |
| | G-CSF | >30 | >30 | >30 |
| | FGF-2 | 0.29 | >30 | >30 |
| | IGF-1 | >30 | >30 | >30 |

Example 4

Identified Compounds are Active in Inhibition of VEGF Expression and Tumor Growth In Vivo A pharmacodynamic model assesses intratumor VEGF levels and selects compounds for in vivo efficacy. Preliminary data demonstrates that several of our compounds effectively inhibit VEGF production in tumor tissues (see FIG. 4A). Briefly, HT1080 cells (a human fibrosarcoma cell line) are implanted subcutaneously in nude mice. After seven days, mice are administrated compounds orally at 20 mg/kg/day for two weeks. The tumors are then excised from the mice and homogenized in Tris-HCl buffer containing proteinase inhibitors (Moulder, S. L., et al., *Cancer Res*. 61(24):8887-95, 2001). Intratumor VEGF levels are subsequently measured using a human VEGF ELISA kit (R&D System, Minneapolis, Minn.). Protein concentrations of the homogenates are measured with a Bio-Rad™ Protein assay kit and intratumor VEGF levels are normalized to the protein concentrations. Treatment with the identified compounds significantly reduces intratumor VEGF protein levels compared to the vehicle control. In addition, treatment with the identified compound for two weeks inhibits tumor growth as compared to the vehicle-treated control groups (see FIG. 4B).

Example 5

Mapping of Functional Domains in a 5' VEGF UTR

Figure 5:
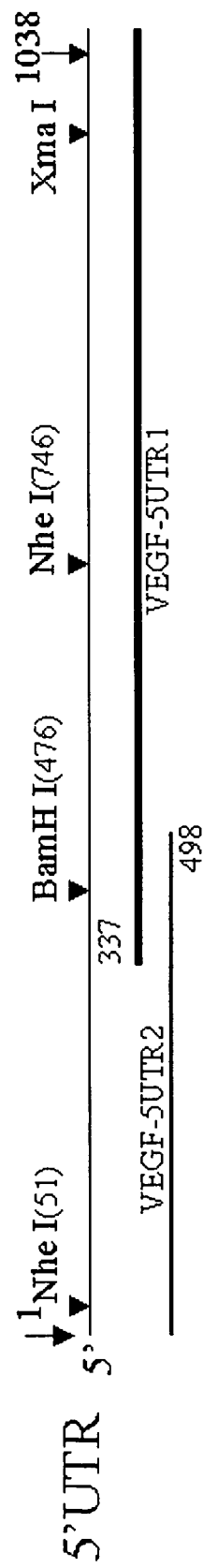
FIG. 5 sets forth a schematic of a 5' VEGF UTR and restriction sites therein. VEGF 5' UTR is amplified from human genomic DNA by two separate PCR reactions. In the overlap region of 5' UTR1 and 5' UTR2, a unique enzyme site BamHI is used to assemble the full-length 5' UTR in subsequent cloning.
Figure 6:
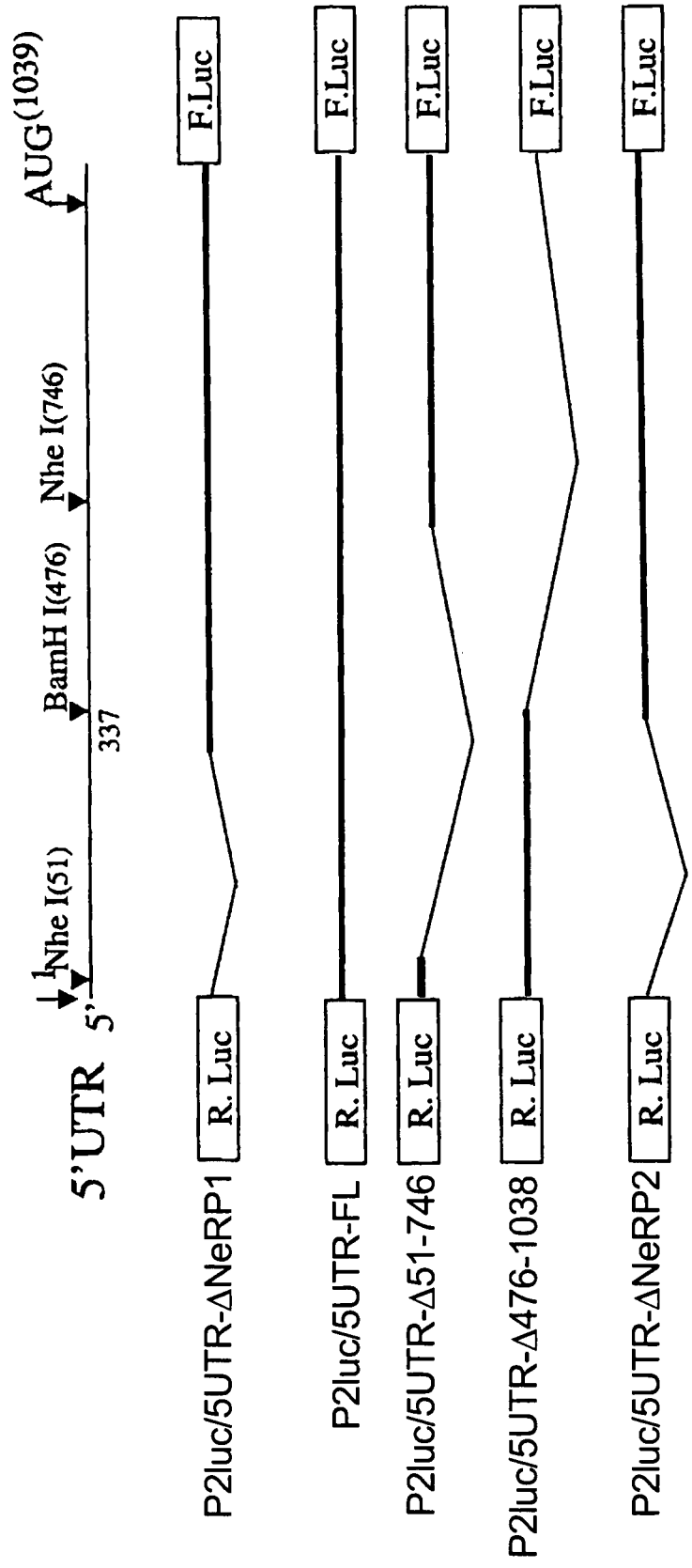
FIG. 6 sets forth a schematic representation of dicistronic plasmids that can be used for transfection experiments. P2luc/5UTR-ΔNeRP1 is a dicistronic plasmid containing VEGF 5' UTR1, in which nucleotides 337 to 1083 of the VEGF cDNA are fused to the firefly luciferase coding sequence; P2luc/5UTR-FL is generated by subcloning VEGF 5'UTR2 into the plasmid p2luc/vegf5utr1 between SalI and BamHI; plasmid p2luc/5UTR-Δ51-476 is derived from p2luc/5UTR-FL by removing the NheI fragment (nt 51 to 746); plasmid p2luc/5UTR-Δ476-1038 is derived from p2luc/vegf5utr-fl by removing the sequence from BamHI site to the 3'end of 5' UTR; plasmid p2luc/5UTR-Δ1-476 is derived from p2luc/5UTR-FL by removing the sequence from BamHI to the 5'end of 5'UTR. P2luc-e can be used as a negative control in this study.
Figure 7:
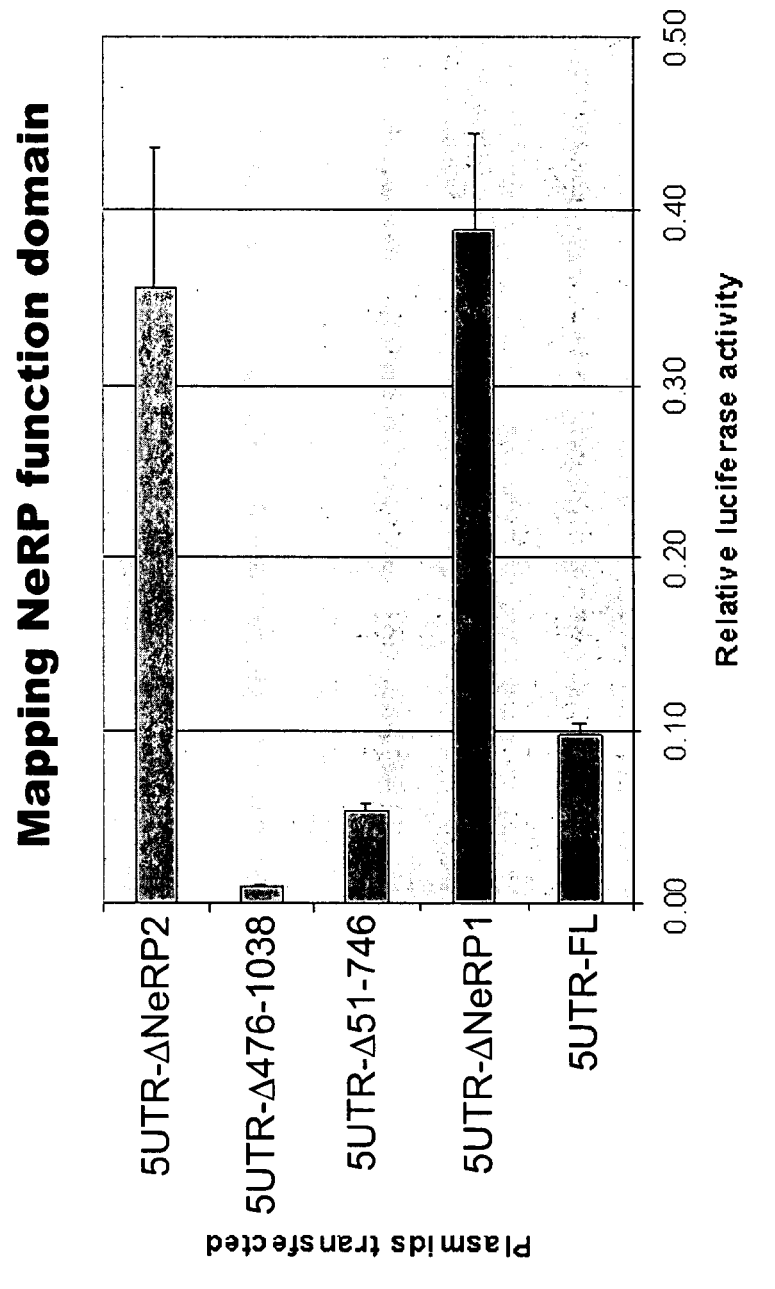
FIG. 7 sets forth results identifying the presence of a VEGF IRES domain (a PTCRE) and a NeRP in the VEGF mRNA 5'UTR. Reporter gene expression is analyzed by monitoring luciferase activity.

VEGF-5UTR1 and 5UTR2 are amplified from human genomic DNA. The full-length 5' UTR is generated by ligation of the two fragments (see FIG. 5). P2luc/VEGF5UTR-FL is generated by inserting the full-length 5' UTR into a dicistronic plasmid (p2luc) between SalI and SmaII sites. Other vectors are derived from p2luc/VEGF5UTR-FL by deleting relevant sequences. All these plasmids are tested in 293 cells by transient transfection. FIG. 6 shows the relative fire-fly luciferase activity (normalized against *Renilla luciferase*) for each of the VEGF 5' UTR fragments. Similar results are obtained from repeating such experiments.

What is claimed:

1. A method for screening candidate compounds for a compound that modulates human vascular endothelial growth factor (VEGF) mRNA translation that is regulated by the untranslated regions of human VEGF mRNA, comprising:
    a. contacting a compound with a cell engineered to stably express a reporter protein encoded by an mRNA transcript comprising a reporter gene coding sequence operably linked to a fragment of a human VEGF 5' UTR encoded by the sequence of SEQ ID NO:3 and a human VEGF 3' UTR, wherein the fragment of the human VEGF 5' UTR is upstream of the reporter gene coding sequence and the human VEGF 3' UTR is downstream of the reporter gene coding sequence, and wherein the mRNA transcript does not comprise SEQ ID NO:4 or a fragment thereof; and
    b. detecting the amount or activity of the reporter protein, wherein a change in the amount or activity of the reporter protein in the presence of the compound relative to the amount or activity of the reporter protein in the absence of the compound indicates that the compound modulates human VEGF mRNA translation that is regulated by the untranslated regions of human VEGF mRNA.

2. A method for screening candidate compounds for a compound that modulates human vascular endothelial growth factor (VEGF) mRNA translation that is regulated by the untranslated regions of human VEGF mRNA, comprising:
    a. contacting a compound with a composition comprising a lysate or translation extract and an mRNA transcript comprising a reporter gene coding sequence operably linked to a fragment of a human VEGF 5' UTR encoded by the sequence of SEQ ID NO:3 and a human VEGF 3' UTR, wherein the fragment of the human VEGF 5' UTR is upstream of the reporter gene coding sequence and the human VEGF 3' UTR is downstream of the reporter gene coding sequence, and wherein the mRNA transcript does not comprise SEQ ID NO:4 or a fragment thereof; and
    b. detecting the amount or activity of the reporter protein encoded by the nucleic acid molecule, wherein a change in the amount or activity of the reporter protein in the presence of the compound relative to the amount or activity of the reporter protein in the absence of the compound indicates that the compound modulates human VEGF mRNA translation that is regulated by the untranslated regions of human VEGF mRNA.

3. The method of claim 1, wherein the reporter gene coding sequence is for green fluorescent protein, luciferase, β-glucuronidase or β-lactamase.

4. The method of claim 2, wherein the reporter gene coding sequence is for green fluorescent protein, luciferase, β-glucuronidase or β-lactamase.

5. The method of claim 1, wherein the cell is a human cell.

6. The method of claim 5, wherein the cell is exposed to hypoxic conditions.

7. The method of claim 5, wherein the cell expresses human VEGF.

8. The method of claim 1, wherein the cell is a cancer cell.

9. The method of claim 2, wherein the translation extract is a cancer cell extract.

10. The method of claim 1, further comprising measuring the effect of the compound on the level of expression of the human VEGF protein.

11. The method of claim 2, further comprising measuring the effect of the compound on the level of expression of the human VEGF protein.

12. A method for screening candidate compounds for a compound that modulates human vascular endothelial growth factor (VEGF) mRNA translation that is regulated by the untranslated regions of human VEGF, comprising:
    (a) contacting a compound with a first cell engineered to stably express a first reporter protein encoded by an mRNA transcript comprising a reporter gene coding sequence operably linked to a fragment of a human VEGF 5' UTR encoded by the sequence of SEQ ID NO:3 and a human VEGF 3' UTR, wherein the fragment of the human VEGF 5' UTR is upstream of the reporter gene coding sequence and the human VEGF 3' UTR is downstream of the reporter gene coding sequence, and wherein the mRNA transcript does not comprise SEQ ID NO:4 or a fragment thereof; and (b) contacting the compound with a second cell engineered to stably express a second reporter protein encoded by an mRNA transcript comprising a second reporter gene coding sequence operably linked to a 5' UTR and a 3'UTR different than a fragment of a human VEGF 5' UTR encoded by the sequence of SEQ ID NO:3 and a human VEGF 3' UTR, wherein the 5' UTR is upstream of the second reporter gene coding sequence and the 3' UTR is downstream of the second reporter gene coding sequence, and wherein the mRNA transcript does not comprise SEQ ID NO:4 or a fragment thereof; and (c) detecting the level of expression of the first and second reporter proteins, wherein an alteration in the level of expression of the first reporter protein in the presence of the compound relative to the level of expression of the first reporter protein in the absence of the compound or the presence of a control, and an alteration in the level of expression of the second reporter protein in the presence of the compound relative to the level of expression of the second reporter protein in the absence of the compound or the presence of a control, indicates that the compound modulates VEGF mRNA translation that is regulated by the untranslated regions of human VEGF mRNA.

13. A method for screening candidate compounds for a compound that modulates human vascular endothelial growth factor (VEGF) mRNA translation that is regulated by the untranslated regions of human VEGF, comprising:

(a) contacting a compound with a composition comprising a lysate or translation extract and an mRNA transcript comprising a reporter gene coding sequence operably linked a fragment of a human VEGF 5' UTR encoded by the sequence of SEQ ID NO:3 and a human VEGF 3' UTR, wherein the nucleotide sequence encoding the fragment of the human VEGF 5' UTR is upstream of the reporter gene coding sequence and the human VEGF 3' UTR is downstream of the reporter gene coding sequence, and wherein the mRNA transcript does not comprise SEQ ID NO:4 or a, fragment thereof (b) contacting the compound with a composition comprising a lysate or translation extract and an mRNA transcript comprising a second reporter gene coding sequence operably linked to a 5' UTR and a 3'UTR different than a fragment of a human VEGF 5' UTR encoded by the sequence of SEQ ID NO:3 and a human VEGF 3' UTR, wherein the 5' UTR is upstream of the second reporter gene coding sequence and the 3' UTR is downstream of the second reporter gene coding sequence, and wherein the mRNA transcript does not comprise SEQ ID NO:4 or a fragment thereof, and (c) detecting the level of expression of the first and second reporter proteins, wherein an alteration in the level of expression of the first reporter protein in the presence of the compound relative to the level of expression of the first reporter protein in the absence of the compound or the presence of a control, and an alteration in the level of expression of the second reporter protein in the presence of the compound relative to the level of expression of the second reporter protein in the absence of the compound or the presence of a control, indicates that the compound modulates VEGF mRNA translation that is regulated by the untranslated regions of human VEGF mRNA.

14. The method of claim 12, further comprising measuring the effect of the compound on the level of expression of the human VEGF protein.

15. The method of claim 13, further comprising measuring the effect of the compound on the level of expression of the human VEGF protein.

16. The method of claim 1, wherein the reporter gene coding sequence is an enzyme.

17. The method of claim 2, wherein the reporter gene coding sequence is an enzyme.

18. The method of claim 12, wherein the first reporter gene coding sequence is an enzyme.

19. The method of claim 13, wherein the first reporter gene coding sequence is an enzyme.

20. The method of claim 12, wherein the second reporter gene coding sequence is an enzyme.

21. The method of claim 13, wherein the second reporter gene coding sequence is an enzyme.

22. The method of claim 12, wherein the reporter gene coding sequence is for green fluorescent protein, luciferase, β-glucuronidase or β-lactamase.

23. The method of claim 13, wherein the reporter gene coding sequence is for green fluorescent protein, luciferase, β-glucuronidase or β-lactamase.

* * * * *

SEQUENCE LISTING

```
<160> NUMBER OF SEQ ID NOS: 26

<210> SEQ ID NO 1
<211> LENGTH: 1038
<212> TYPE: DNA
<213> ORGANISM: Artificial
<220> FEATURE:
<223> OTHER INFORMATION: Synthetic Construct

<400> SEQUENCE: 1
tcgcggaggc ttggggcagc cgggtagctc ggaggtcgtg gcgctggggg ctagcaccag        60
cgctctgtcg ggaggcgcag cggttaggtg gaccggtcag cggactcacc ggccagggcg       120
ctcggtgctg gaatttgata ttcattgatc cgggttttat ccctcttctt ttttcttaaa       180
catttttttt taaaactgta ttgtttctcg ttttaattta tttttgcttg ccattcccca       240
cttgaatcgg gccgacggct tggggagatt gctctacttc cccaaatcac tgtggatttt       300
```

-continued

```
ggaaaccagc agaaagagga aagaggtagc aagagctcca gagagaagtc gaggaagaga      360
gagacggggt cagagagagc gcgcgggcgt gcgagcagcg aaagcgacag gggcaaagtg      420
agtgacctgc ttttgggggt gaccgccgga gcgcggcgtg agccctcccc cttgggatcc      480
cgcagctgac cagtcgcgct gacgacagac agacagacag ccgcccccag ccccagctac      540
cacctcctcc ccggccggcg gcggacagtg gacgcggcgg cgagccgcgg gcaggggccg      600
gagcccgcgc ccggaggcgg ggtggagggg gtcgggctcg gcggcgtcgc actgaaactt      660
ttcgtccaac ttctgggctg ttctcgcttc ggaggagccg tggtccgcgc ggggaagcc      720 gagccgagcg gagccgcgag aagtgctagc tcgggccggg aggagccgca gccggaggag      780
ggggaggagg aagaagagaa ggaagaggag aggggccgc agtggcgact cggcgctcgg      840
aagccgggct catggacggg tgaggcgcg gtgtgcgcag acagtgctcc agccgcgcgc      900
gctccccagg ccctggcccg ggcctcgggc cggggaggaa gagtagctcg ccgaggcgcc      960
gaggagagcg ggccgcccca cagcccgagc cggagaggga gcgcgagccg cgccggcccc     1020
ggtcgggcct ccgaaacc                                                   1038
```

<210> SEQ ID NO 2
<211> LENGTH: 576
<212> TYPE: DNA
<213> ORGANISM: Artificial
<220> FEATURE:
<223> OTHER INFORMATION: Synthetic Construct

<400> SEQUENCE: 2

```
atgaactttc tgctgtcttg ggtgcattgg agccttgcct tgctgctcta cctccaccat       60
gccaagtggt cccaggctgc acccatggca gaaggaggag ggcagaatca tcacgaagtg      120
gtgaagttca tggatgtcta tcagcgcagc tactgccatc caatcgagac cctggtggac      180
atcttccagg agtaccctga tgagatcgag tacatcttca gccatcctg tgtgcccctg      240 atgcgatgcg ggggctgctg caatgacgag ggcctggagt gtgtgcccac tgaggagtcc      300
aacatcacca tgcagattat gcggatcaaa cctcaccaag gccagcacat aggagagatg      360
agcttcctac agcacaacaa atgtgaatgc agaccaaaga aagatagagc aagacaagaa      420
aatccctgtg gccttgctc agagcggaga aagcatttgt ttgtacaaga tccgcagacg      480
tgtaaatgtt cctgcaaaaa cacagactcg cgttgcaagg cgaggcagct tgagttaaac      540
gaacgtactt gcagatgtga caagccgagg cggtga                              576
```

<210> SEQ ID NO 3
<211> LENGTH: 702
<212> TYPE: DNA
<213> ORGANISM: Artificial
<220> FEATURE:
<223> OTHER INFORMATION: Synthetic Construct

<400> SEQUENCE: 3

```
tccagagaga agtcgaggaa gagagagacg gggtcagaga gagcgcgcgg gcgtgcgagc       60
agcgaaagcg acaggggcaa agtgagtgac ctgcttttgg gggtgaccgc cggagcgcgg      120
cgtgagccct ccccccttggg atcccgcagc tgaccagtcg cgctgacgga cagacagaca      180
gacaccgccc ccagcccag ctaccacctc tcccccggcc ggcggcggac agtggacgcg      240
gcggcgagcc gcgggcaggg gccggagccc gcgcccggag gcggggtgga ggggggtcggg      300 gctcgcggc tcgcactgaa actttttcgtc caacttctgg gctgttctcg cttcggagga      360
gccgtggtcc gcgcggggga agccgagccg agcggagccg cgagaagtgc tagctcgggc      420
```

```
cgggaggagc cgcagccgga ggaggggagg gaggaagaag agaaggaaga ggagaggggg      480
ccgcagtggc gactcggcgc tcggaagccg ggctcatgga cgggtgaggc ggcggtgtgc      540
gcagacagtg ctccagccgc gcgcgctccc caggccctgg cccgggcctc gggccgggga      600
ggaagagtag ctcgccgagg cgccgaggag agcgggccgc cccacagccc gagccggaga      660
gggagcgcga ccgcgccgg ccccggtcgg gcctccgaaa cc                          702

<210> SEQ ID NO 4
<211> LENGTH: 336
<212> TYPE: DNA
<213> ORGANISM: Artificial
<220> FEATURE:
<223> OTHER INFORMATION: Synthetic Construct

<400> SEQUENCE: 4
tcgcggaggc ttggggcagc cgggtagctc ggaggtcgtg gcgctggggg ctagcaccag       60
cgctctgtcg ggaggcgcag cggttaggtg gaccggtcag cggactcacc ggccagggcg      120
ctcggtgctg gaatttgata ttcattgatc cgggttttat ccctcttctt ttttcttaaa     180
catttttttt taaaactgta ttgtttctcg ttttaattta tttttgcttg ccattccca      240 cttgaatcgg gccgacggct tggggagatt gctctacttc cccaaatcac tgtggatttt     300
ggaaaccagc agaaagagga aagaggtagc aagagc                                336

<210> SEQ ID NO 5
<211> LENGTH: 485
<212> TYPE: DNA
<213> ORGANISM: Artificial
<220> FEATURE:
<223> OTHER INFORMATION: Synthetic Construct

<400> SEQUENCE: 5
gccggcggcg gacagtggac gcggcggcga ccgcgggca ggggccggag cccgcgcccg       60
gaggcggggt ggaggggggtc ggggctcgcg gcgtcgcact gaaacttttc gtccaacttc    120
tgggctgttc tcgcttcgga ggagccgtg tccgcgcggg ggaagccgag ccgagcggag      180
ccgcgagaag tgctagctcg ggccgggagg agccgcagcc ggaggagggg gaggaggaag    240
aagagaagga agaggagagg gggccgcagt ggcgactcgg cgctcggaag ccgggctcat     300
ggacgggtga ggcggcggtg tgcgcagaca gtgctccagc cgcgcgcgct ccccaggccc     360
tggcccgggc ctcgggccgg ggaggaagag tagctcgccg aggcgccgag gagagcgggc    420
cgccccacag cccgagccgg agaggagcg cgagccgcgc cggccccggt cgggcctccg      480
aaacc                                                                    485

<210> SEQ ID NO 6
<211> LENGTH: 556
<212> TYPE: DNA
<213> ORGANISM: Artificial
<220> FEATURE:
<223> OTHER INFORMATION: Synthetic Construct

<400> SEQUENCE: 6
cagctgacca gtcgcgctga cggacagaca gacagacacc gccccagcc ccagctacca       60 cctcctcccc ggccggcggc ggacagtgga cgcggcggcg agccgcgggc aggggccgga    120
gcccgcgccc ggaggcgggg tggaggggt cggggctcgc ggcgtcgcac tgaaactttt     180
cgtccaactt ctgggctgtt ctcgcttcgg aggagccgtg gtccgcgcgg gggaagccga    240
gccgagcgga gccgcgagaa gtgctagctc gggccgggag gagccgcagc cggaggaggg    300
```

```
ggaggaggaa gaagagaagg aagaggagag ggggccgcag tggcgactcg gcgctcggaa    360
gccgggctca tggacgggtg aggcggcggt gtgcgcagac agtgctccag ccgcgcgcgc    420
tccccaggcc ctggcccggg cctcgggccg ggaggaaga gtagctcgcc gaggcgccga     480
ggagagcggg ccgccccaca gcccgagccg gagagggagc gcgagccgcg ccggccccgg    540
tcgggcctcc gaaacc                                                    556
```

```
<210> SEQ ID NO 7
<211> LENGTH: 294
<212> TYPE: DNA
<213> ORGANISM: Artificial
<220> FEATURE:
<223> OTHER INFORMATION: Synthetic Construct

<400> SEQUENCE: 7
gctagctcgg gccgggagga gccgcagccg gaggagggg aggaggaaga agagaaggaa      60
gaggagaggg ggccgcagtg gcgactcggc gctcggaagc cgggctcatg gacgggtgag    120
gcggcggtgt gcgcagacag tgctccagcc gcgcgcgctc cccaggccct ggcccgggcc    180
tcgggccggg gaggaagagt agctcgccga ggcgccgagg agagcgggcc gccccacagc    240
ccgagccgga gagggagcgc gagccgcgcc ggccccggtc gggcctccga aacc          294
```

```
<210> SEQ ID NO 8
<211> LENGTH: 194
<212> TYPE: DNA
<213> ORGANISM: Artificial
<220> FEATURE:
<223> OTHER INFORMATION: Synthetic Construct

<400> SEQUENCE: 8
cgggctcatg gacgggtgag gcggcggtgt gcgcagacag tgctccagcc gcgcgcgctc     60
cccaggccct ggcccgggcc tcgggccggg gaggaagagt agctcgccga ggcgccgagg    120
agagcgggcc gccccacagc ccgagccgga gagggagcgc gagccgcgcc ggccccggtc    180
gggcctccga aacc                                                      194
```

```
<210> SEQ ID NO 9
<211> LENGTH: 476
<212> TYPE: DNA
<213> ORGANISM: Artificial
<220> FEATURE:
<223> OTHER INFORMATION: Synthetic Construct

<400> SEQUENCE: 9
tcgcggaggc ttggggcagc cgggtagctc ggaggtcgtg gcgctggggg ctagcaccag     60
cgctctgtcg ggaggcgcag cggttaggtg accggtcag cggactcacc ggccagggcg    120
ctcggtgctg gaatttgata ttcattgatc cgggttttat ccctcttctt ttttcttaaa    180 cattttttt taaaactgta ttgtttctcg ttttaattta ttttgcttg ccattcccca     240 cttgaatcgg gccgacggct tggggagatt gctctacttc cccaaatcac tgtggatttt    300
ggaaaccagc agaaagagga aagaggtagc aagagctcca gagagaagtc gaggaagaga    360
gagacggggt cagagagagc gcgcgggcgt gcgagcagcg aaagcgacag gggcaaagtg    420
agtgacctgc ttttgggggt gaccgccgga gcgcggcgtg agccctcccc cttggg       476
```

```
<210> SEQ ID NO 10
<211> LENGTH: 554
<212> TYPE: DNA
<213> ORGANISM: Artificial
<220> FEATURE:
```

<223> OTHER INFORMATION: Synthetic Construct

<400> SEQUENCE: 10

| | |
|---|---|
| tcgcggaggc ttggggcagc cgggtagctc ggaggtcgtg gcgctggggg ctagcaccag | 60 |
| cgctctgtcg ggaggcgcag cggttaggtg gaccggtcag cggactcacc ggccagggcg | 120 |
| ctcggtgctg gaatttgata ttcattgatc cgggttttat ccctcttctt ttttcttaaa | 180 |
| catttttttt taaaactgta ttgtttctcg ttttaattta tttttgcttg ccattcccca | 240 |
| cttgaatcgg gccgacggct tggggagatt gctctacttc cccaaatcac tgtggatttt | 300 |
| ggaaaccagc agaaagagga aagaggtagc aagagctcca gagagaagtc gaggaagaga | 360 |
| gagacggggt cagagagagc gcgcgggcgt gcgagcagcg aaagcgacag ggcaaagtg | 420 |
| agtgacctgc ttttgggggt gaccgccgga gcgcggcgtg agccctcccc cttgggatcc | 480 |
| cgcagctgac cagtcgcgct gacggacaga cagacagaca ccgccccag ccccagctac | 540 |
| cacctcctcc ccgg | 554 |

<210> SEQ ID NO 11
<211> LENGTH: 51
<212> TYPE: DNA
<213> ORGANISM: Artificial
<220> FEATURE:
<223> OTHER INFORMATION: Synthetic Construct

<400> SEQUENCE: 11

| | |
|---|---|
| tcgcggaggc ttggggcagc cgggtagctc ggaggtcgtg gcgctggggg c | 51 |

<210> SEQ ID NO 12
<211> LENGTH: 91
<212> TYPE: DNA
<213> ORGANISM: Artificial
<220> FEATURE:
<223> OTHER INFORMATION: Synthetic construct

<400> SEQUENCE: 12

| | |
|---|---|
| tcgcggaggc ttggggcagc cgggtagctc ggaggtcgtg gcgctggggg ctagcaccag | 60 |
| cgctctgtcg ggaggcgcag cggttaggtg g | 91 |

<210> SEQ ID NO 13
<211> LENGTH: 335
<212> TYPE: DNA
<213> ORGANISM: Artificial
<220> FEATURE:
<223> OTHER INFORMATION: Synthetic Construct

<400> SEQUENCE: 13

| | |
|---|---|
| tcgcggaggc ttggggcagc cgggtagctc ggaggtcgtg gcgctggggg ctagcaccag | 60 |
| cgctctgtcg ggaggcgcag cggttaggtg gaccggtcag cggactcacc ggccagggcg | 120 |
| ctcggtgctg gaatttgata ttcattgatc cgggttttat ccctcttctt ttttcttaaa | 180 |
| catttttttt taaaactgta ttgtttctcg ttttaattta tttttgcttg ccattcccca | 240 |
| cttgaatcgg gccgacggct tggggagatt gctctacttc cccaaatcac tgtggatttt | 300 |
| ggaaaccagc agaaagagga aagaggtagc aagag | 335 |

<210> SEQ ID NO 14
<211> LENGTH: 332
<212> TYPE: DNA
<213> ORGANISM: Artificial
<220> FEATURE:
<223> OTHER INFORMATION: Synthetic Construct

```
<400> SEQUENCE: 14
tcgcggaggc ttggggcagc cgggtagctc ggaggcgtgg cgctgggggc tagcaccagc      60
gctctgtcgg gaggcgcagc ggttaggtgg accggtcagc ggactcaccg gccagggcgc     120
tcggtgctgg aatttgatat tcattgatcc gggttttatc cctcttcttt tttcttaaac     180
attttttttt aaaactgttt gtttctcgtt ttaatttatt tttgcttgcc attccccact     240
tgaatcgggc cgacggcttg gggagattgc tctacttccc caaatcactg tggattttgg     300
aaaccagcag aaagaggaaa gagagcaaga gc                                    332

<210> SEQ ID NO 15
<211> LENGTH: 331
<212> TYPE: DNA
<213> ORGANISM: Artificial
<220> FEATURE:
<223> OTHER INFORMATION: Synthetic Construct

<400> SEQUENCE: 15
tcgcggaggc ttggggcagc cgggtagctc ggagtcgtgg cgctgggggc tagcaccagc      60
gctctgtcgg gaggcgcagc ggttaggtgg accgtcagcg gactcaccgg ccagggcgct     120
cggtgctgga atttgatatt cattgatccg ggtttatccc tcttcttttt tcttaaacat     180 tttttttaa aactgtattg tttctcgttt taattatttt tgcttgccat tccccacttg      240
aatcgggccg acggcttggg gagattgctc tactccccaa atcactgtgg attttggaaa     300
ccagcagaaa gaggaaagag gtagcaagag c                                     331

<210> SEQ ID NO 16
<211> LENGTH: 330
<212> TYPE: DNA
<213> ORGANISM: Artificial
<220> FEATURE:
<223> OTHER INFORMATION: Synthetic Construct

<400> SEQUENCE: 16
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg     120
ctcggtgctg gaatttgata ttcattgatc cgggttttat ccctcttctt ttttcttaaa     180 cattttttt taaaactgta ttgtttctcg ttttaattta ttttgcttg ccattcccca      240 cttgaatcgg gccgacggct tggggagatt gctctacttc cccaaatcac tgtggatttt     300
ggaaaccagc agaaagagga aagaggtagc                                       330

<210> SEQ ID NO 17
<211> LENGTH: 329
<212> TYPE: DNA
<213> ORGANISM: Artificial
<220> FEATURE:
<223> OTHER INFORMATION: Synthetic Construct

<400> SEQUENCE: 17
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg     120
ctcggtgctg gaattttcat tgatccgggt ttatccctc ttcttttttc ttaaacattt     180 tttttaact gtattgtttc tcgttttaat ttattttgc ttgccattcc ccacttgaat      240
cgggccgacg gcttgggag attgctctac ttccccaaat cactgtggat tttggaaacc      300
agcagaaaga ggaaagaggt agcaagagc                                        329
```

```
<210> SEQ ID NO 18
<211> LENGTH: 328
<212> TYPE: DNA
<213> ORGANISM: Artificial
<220> FEATURE:
<223> OTHER INFORMATION: Synthetic Construct

<400> SEQUENCE: 18
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg     120
ctcggtgctg gaatttgata ttcattgatc cgggttttat ccctcttctt ttttcttaaa     180 cattttttt taaaactgta ttgtttctcg ttttaattta tttttgcttg ccattcccca      240
cttgaatcgg gccgacggct tggctctact tccccaaatc actgtggatt ttggaaacca     300
gcagaaagag gaaagaggta gcaagagc                                        328

<210> SEQ ID NO 19
<211> LENGTH: 326
<212> TYPE: DNA
<213> ORGANISM: Artificial
<220> FEATURE:
<223> OTHER INFORMATION: Synthetic Construct

<400> SEQUENCE: 19
tcgcggaggc ttggggcagc ggaggtcgtg gcgctggggg ctagcaccag cgctctgtcg      60
ggaggcgcag cggttaggtg gaccggtcag cggactcacc ggccagggcg ctcggtgctg     120
gaatttgata ttcattgatc cgggttttat ccctcttctt ttttcttaaa cattttttt     180 taaaactgta ttgtttctcg ttttaattta tttttgcttg ccattcccca cttgaatcgg     240
gccgacggct tggggagatt gctctacttc cccaaatcac tgtggatttt ggaaaccagc     300
agaaagagga aagaggtagc aagagc                                          326

<210> SEQ ID NO 20
<211> LENGTH: 326
<212> TYPE: DNA
<213> ORGANISM: Artificial
<220> FEATURE:
<223> OTHER INFORMATION: Synthetic Construct

<400> SEQUENCE: 20
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg     120
ctcggtgctg gaatttgata ttcattgatc cgggttttat ccctcttctt ttttcttaaa     180 cattttttt taaaactgta ttgtttctcg ttttaattta tttttgcttg ccattcccca      240
cttgaatcgg gccgacggct tggggagatt gctctacttc cccaaatcac tgtggatttt     300
ggaaaccagc agaaagagga aagagg                                          326

<210> SEQ ID NO 21
<211> LENGTH: 316
<212> TYPE: DNA
<213> ORGANISM: Artificial
<220> FEATURE:
<223> OTHER INFORMATION: Synthetic Construct

<400> SEQUENCE: 21
tcgcggaggc ttggggcagc cgggtagctc ggaggtcgtg gcgctggggg ctagcaccag      60
cgctctgtcg ggaggcgcag cggttaggtg gaccggtcag cggactcacc ggccagggcg     120
```

```
ctcggtgctg gaatttgata ttcattgatc cgggttttat ccctcttctt ttttcttaaa    180 cattttttt taaaactgta ttgtttctcg ttttaattta ttttgcttg ccattcccca      240 cttgaatcgg gccgacggct tggggagatt gctctacttc cccaaatcac tgtggatttt    300
ggaaaccagc agaaag                                                    316
```

<210> SEQ ID NO 22
<211> LENGTH: 306
<212> TYPE: DNA
<213> ORGANISM: Artificial
<220> FEATURE:
<223> OTHER INFORMATION: Synthetic Construct

<400> SEQUENCE: 22

```
ttggggcagc cgggtagctc ggaggtcgtg gcgctggggg ctagcaccag cgctctgtcg    60
ggaggcgcag cggttaggtg gaccggtcag cggactcacc ggccagggcg ctcggtgctg   120
gaatttgata ttcattgatc cgggttttat ccctcttctt ttttcttaaa cattttttt    180 taaaactgta ttgtttctcg ttttaattta ttttgcttg ccattcccca cttgaatcgg    240
gccgacggct tggggagatt gctctacttc cccaaatcac tgtggatttt ggaaaccagc   300
agaaag                                                              306
```

<210> SEQ ID NO 23
<211> LENGTH: 296
<212> TYPE: DNA
<213> ORGANISM: Artificial
<220> FEATURE:
<223> OTHER INFORMATION: Synthetic Construct

<400> SEQUENCE: 23

```
cgggtagctc ggaggtcgtg gcgctggggg ctagcaccag cgctctgtcg ggaggcgcag    60
cggttaggtg gaccggtcag cggactcacc ggccagggcg ctcggtgctg gaatttgata   120
ttcattgatc cgggttttat ccctcttctt ttttcttaaa cattttttt taaaactgta    180 ttgtttctcg ttttaattta ttttgcttg ccattcccca cttgaatcgg gccgacggct    240
tggggagatt gctctacttc cccaaatcac tgtggatttt ggaaaccagc agaaag       296
```

<210> SEQ ID NO 24
<211> LENGTH: 286
<212> TYPE: DNA
<213> ORGANISM: Artificial
<220> FEATURE:
<223> OTHER INFORMATION: Synthetic Construct

<400> SEQUENCE: 24

```
cgggtagctc ggaggtcgtg gcgctggggg ctagcaccag cgctctgtcg ggaggcgcag    60
cggttaggtg gaccggtcag cggactcacc ggccagggcg ctcggtgctg gaatttgata   120
ccctcttctt ttttcttaaa cattttttt taaaactgta ttgtttctcg ttttaattta    180 ttttgcttg ccattcccca cttgaatcgg gccgacggct gctctacttc cccaaatcac   240
tgtggatttt ggaaaccagc agaaagagga aagaggtagc aagagc                  286
```

<210> SEQ ID NO 25
<211> LENGTH: 276
<212> TYPE: DNA
<213> ORGANISM: Artificial
<220> FEATURE:
<223> OTHER INFORMATION: Synthetic Construct

<400> SEQUENCE: 25

-continued

```
gcgctggggg ctagcaccag cgctctgtcg ggaggcgcag cggttaggtg gaccggtcag    60
cggactcacc ggccagggcg ctcggtgctg gaatttgata ttcattgatc cgggttttat   120
ccctcttctt ttttcttaaa catttttttt taaaactgta ttgtttctcg ttttaattta   180
tttttgcttg ccattcccca cttgaatcgg gccgacggct tggggagatt gctctacttc   240
cccaaatcac tgtggatttt ggaaaccagc agaaag                             276

<210> SEQ ID NO 26
<211> LENGTH: 266
<212> TYPE: DNA
<213> ORGANISM: Artificial
<220> FEATURE:
<223> OTHER INFORMATION: Synthetic Construct

<400> SEQUENCE: 26
ggaggtcgtg gcgctggggg ctagcaccag cgctctgtcg ggaggcgcag cggttaggtg    60
gaccggtcag cggactcacc ggccagggcg ctcggtgctg gaatttgata ccctcttctt   120
ttttcttaaa catttttttt taaaactgta ttgtttctcg ccattcccca cttgaatcgg   180
gccgacggct tggggagatt gctctacttc cccaaatcac tgtggatttt ggaaaccagc   240
agaaagagga aagaggtagc aagagc                                        266
```